US007998480B2

(12) United States Patent
Brophy et al.

(10) Patent No.: US 7,998,480 B2
(45) Date of Patent: Aug. 16, 2011

(54) HUMAN BNP IMMUNOSPECIFIC ANTIBODIES

(75) Inventors: Susan E. Brophy, Lindenhurst, IL (US); Joan D. Tyner, Beach Park, IL (US); Lowell J. Tyner, legal representative, Chicago, IL (US); Bailin X. Tu, Lake Bluff, IL (US); Mary S. Pinkus, Chicago, IL (US); Jessie W. Shih, Lake Forest, IL (US); Bryan C. Tieman, Elmhurst, IL (US)

(73) Assignee: Abbott Laboratories, Abbott Park, IL (US)

( * ) Notice: Subject to any disclaimer, the term of this patent is extended or adjusted under 35 U.S.C. 154(b) by 546 days.

(21) Appl. No.: 12/189,232

(22) Filed: Aug. 11, 2008

(65) Prior Publication Data

US 2009/0123473 A1 May 14, 2009

Related U.S. Application Data

(63) Continuation of application No. 11/595,625, filed on Nov. 9, 2006, now abandoned.

(60) Provisional application No. 60/734,964, filed on Nov. 9, 2005.

(51) Int. Cl.
*A61K 39/395* (2006.01)
*C12N 5/10* (2006.01)
*G01N 33/53* (2006.01)

(52) U.S. Cl. ............... 424/133.1; 424/135.1; 424/139.1; 424/141.1; 424/142.1; 424/145.1; 435/328; 435/331; 435/336; 435/358; 435/975

(58) Field of Classification Search ........................ None
See application file for complete search history.

(56) References Cited

U.S. PATENT DOCUMENTS

| | | | |
|---|---|---|---|
| 4,399,216 A | 8/1983 | Axel et al. |
| 4,510,245 A | 4/1985 | Cousens et al. |
| 4,607,023 A | 8/1986 | Thibault et al. |
| 4,634,665 A | 1/1987 | Axel et al. |
| 4,816,397 A | 3/1989 | Boss et al. |
| 4,816,567 A | 3/1989 | Cabilly et al. |
| 4,968,615 A | 11/1990 | Koszinowski et al. |
| 5,114,923 A | 5/1992 | Seilhamer et al. |
| 5,168,062 A | 12/1992 | Stinski |
| 5,179,017 A | 1/1993 | Axel et al. |
| 5,468,646 A | 11/1995 | Mattingly et al. |
| 5,545,806 A | 8/1996 | Lonberg et al. |
| 5,674,710 A | 10/1997 | Seilhamer et al. |
| 6,090,382 A | 7/2000 | Salfeld et al. |
| 6,117,644 A | 9/2000 | DeBold |
| 6,124,430 A | 9/2000 | Mischak et al. |
| 6,162,902 A | 12/2000 | Mischak et al. |
| 6,376,207 B1 | 4/2002 | Mischak et al. |
| 6,461,828 B1 | 10/2002 | Stanton et al. |
| 6,677,124 B2 | 1/2004 | Tsuji et al. |
| 6,770,740 B1 | 8/2004 | Rice et al. |
| 7,341,838 B2 | 3/2008 | Buechler et al. |
| 7,351,586 B2 | 4/2008 | Friese et al. |
| 2003/0022235 A1 | 1/2003 | Dahlen et al. |
| 2003/0162710 A1 | 8/2003 | Sudoh et al. |
| 2003/0199000 A1 | 10/2003 | Valkirs et al. |
| 2003/0229207 A1* | 12/2003 | Studnicka .................. 530/387.1 |
| 2004/0132013 A1 | 7/2004 | De Bold |
| 2004/0175379 A1 | 9/2004 | DeVries et al. |
| 2004/0180396 A1 | 9/2004 | Bergmann et al. |
| 2004/0209307 A1 | 10/2004 | Valkirs et al. |
| 2004/0219509 A1 | 11/2004 | Valkirs et al. |
| 2004/0243010 A1 | 12/2004 | Zoghbi et al. |
| 2004/0253655 A1 | 12/2004 | Tsuji et al. |
| 2004/0265926 A1 | 12/2004 | Ng |
| 2005/0014287 A1 | 1/2005 | Friese et al. |
| 2005/0064511 A1 | 3/2005 | Buechler et al. |
| 2006/0121042 A1 | 6/2006 | Dall'Acqua et al. |
| 2006/0121242 A1 | 6/2006 | Pesovic et al. |
| 2006/0183154 A1 | 8/2006 | Shih et al. |
| 2007/0207152 A1 | 9/2007 | Brophy et al. |

FOREIGN PATENT DOCUMENTS

| | | |
|---|---|---|
| EP | 0 384 176 | 8/1990 |
| EP | 0 418 308 | 3/1991 |
| EP | 0 542 255 | 5/1993 |
| EP | 0 914 344 | 5/1999 |
| EP | 1 016 867 | 7/2000 |
| EP | 1 030 177 | 8/2000 |
| JP | 3297392 | 12/1991 |
| JP | 2676114 | 11/1997 |
| WO | 2004/094460 | 11/2004 |
| WO | 2007056507 A1 | 5/2007 |

OTHER PUBLICATIONS

Colucci, et al., "Intravenous nesiritide, a natriuretic peptide, in the treatment of decompensated congestive heart failure", N. Engl. Med., 2000, 343 (34), pp. 246-253.

PCT International Application No. PCT/US2006/0043608; Transmittal of the International Search Report and the Written Opinion of the International Searching Authority, mailed Mar. 27, 2007 (13 pages).

Thorpe, et al., "Enhanced Chemiluminescent Reactions Catalyzed by Horseradish Peroxidase," Methods in Enzymology, 1986, 133, pp. 333-353.

Tsutamoto, et al., "Attenuation of Compensation of Endogenous Cardiac Natriuretic Peptide System in Chronic Heart Failure," 1997, 96, pp. 509-516.

(Continued)

*Primary Examiner* — Jeffrey Stucker
*Assistant Examiner* — Stephen Gucker
(74) *Attorney, Agent, or Firm* — Lisa V. Mueller; Polsinelli Shughart; Audrey L Bartnicki

(57) ABSTRACT

The present invention relates to antibodies that immunospecifically bind to human brain natriuretic peptide or a human brain natriuretic peptide fragment with a high binding affinity, methods for producing and selecting said antibodies, immunoassays for human brain natriuretic peptide or a human brain natriuretic peptide fragment that employ said antibodies and therapeutic compositions containing said antibodies.

20 Claims, 32 Drawing Sheets

OTHER PUBLICATIONS

PCT International Application No. PCT/US2008/062973, Transmittal of the International Search Report and the Written Opinion of the International Searching Authority, mailed Sep. 2, 2008.

Abbott AXYSM® System, BNP package insert, REF 8G82-20 Abbott Diagnostics Division, Feb. 2004.

Apple, et al., "Quality Specifications for B-Type Natriuretic Peptide Assays," *Clin. Chem.*, 51(3):486-493 (2005).

Ausubel, et al., *Curr. Protocols in Molec. Biol.*, Section 2.10 (Terry Brown) and Section 6.3 (William W. Strauss) (1997).

Belenky, et al., "The effect of class-specific protease inhibitors on the stabilization of B-type natriuretic peptide in human plasma," *Clinica Chimica Acta*, 340:163-172 (2004).

Benjamini, et al., S., *Immunology, A Short Course*, Immunogens and Antigens, $2^{nd}$ Ed., pp. 37-40 (1991).

Berzofsky, et al., "Antigen-Antibody Interactions and Monoclonal Antibodies," *Fund. Immunol.*, 2:315-336 (1989).

Bird, et al., "Single-Chain Antigen-Binding Proteins," *Science*, 242:423-426 (1988).

Bluestein, "Comparing BNP ASSAYS, Factors Impacting Analytical Method Comparison," *Bayer Healthcare Diagnostics Division Publ.*, (2004).

Boder, et al., "Directed evolution of antibody fragments with monovalent femtomolar antigen-binding affinity," *PNAS*, 97(20): 10701-10705, (2000).

Boder, et al., "Optimal Screening of Surface-Displayed Polypeptide Libraries," *Biotechnol. Prog.*, 14:55-62 (1998).

Boder, et al., "Yeast Surface Display for Directed Evolution of Protein Expression, Affinity, and Stability," *Meth. in Enzymol.*, 328:430-444 (2000).

Boder, et al., "Yeast surface display for screening combinatorial polypeptide libraries," *Nature Biotech.*, 15(6):553-557 (1997).

Bogan, et al., "Anatomy of Hot Spots in Protein Interfaces," *J. Mol. Biol.*, 280:1-9 (1998).

Boss, et al., "Genetically engineered antibodies," *Imunol. Today*, 6(1):12-13 (1985).

Brandt, et al., "Dipeptidyl-Peptidase IV Converts Intact B- Type Natriuretic Peptide into Its *des*-SerPro Form," *Clin. Chem.*, 52(1):82-87 (2006).

Buckley, et al., "Cardiac peptide stability, aprotinin and room temperature: importance for assessing cardiac function in clinical practice," *Clin. Sci.*, 97:689-695 (1999).

Cataliotti, et al., "Circulating Natriuretic Peptide Concentrations in Patients with End-Stage Renal Disease: Role of Brain Natriuretic Peptide as a Biomarker for Ventricular Remodeling," *Mayo Clin. Proc.*, 76:1111-1119 (2001).

Davidson, et al., "Brain natriuretic peptide," *J. of Hypertension*, 12:329-336 (1994).

Diagnostic Automation/Cortez Diagnostics, Inc., "Nt-proBNP ELISA Quantitative dertermination of Nt-proBNP in biological fluids," (Cat. No. 2852-7), pp. 1-8 (1997).

Galfre, et al., "Antibodies to major histocompatibility antigens produced by hybrid cell lines," *Nature*, 266:550-552 (1977).

Gutkowska, et al., "Atrial Natriuretic Factor in Human Plasma," *Biochem. & Biophys. Res. Comm.*, 139(1):287-295 (1986).

Holmes, et al., "Renal, Endocrine, and Hemodynamic Effects of Human Brain Natriuretic Peptide in Normal Man," *J. of Clin. Endocrin. & Metab.*, 76(1):91-96 (1993).

Huston, et al., "Protein engineering of antibody binding sites: Recovery of specific activity in an anti-digoxin single-chain Fv analogue produced in *Escherichia coli*," *PNAS*, 85:5879-5883 (1988).

Itoh, et al., "Preparation of Monoclonal Antibodies against Brain Natriuretic Peptide and Their Application to Radioimmunoassay and Passive Immunization," *Endocrinology*, 127(3):1292-1300 (1990).

Kabat, et al., "Sequences of Proteins of Immun. Interest," *U.S. Dept. of Health & Human Serv., NIH Publ. 91/3242*, $5^{th}$:Tb1 of Cont., (1991).

Kaufman, et al, "Amplification and Expression of Sequences cotransfected with a Modular Dihydrofolate Reductase Complementary DNA Gene," *J. Mol. Biol.*, 159:601-621 (1982).

Kenny, et al., "Hydrolysis of human and pig brain natriuretic peptides, urodilatin, C-type natriuretic peptide and some C-receptor ligands by endopeptidase-24.11," *Biochem. J.*, 291:83-88 (1993).

Ma, et al., "Protein-protein interactions: Structurally conserved residues distinguish between binding sites and exposed protein surfaces," *PNAS*, 100(10):5772-5777 (2003).

McCafferty, et al., "Phage antibodies: filamentous phage displaying antibody variable domains," *Nature*, 348:552-554 (1990).

Mizushima, et al., "pEF-BOS, a powerful mammalian expression vector," *Nucl. Acids Res.*, 18(17):5322 (1990).

Morrison, et al., "Chimeric human antibody molecules: Mouse antigen-binding domains with human constant region domains," *PNAS*, 81:6851-6855 (1984).

Motwani, et al., "Plasma brain natriuretic peptide as an indicator for angiotensin-converting—enzyme inhibition after myocardial infarction," *The Lancet*, 341:1109-1113 (1993).

Mukoyama, et al., "Brain Natriuretic Peptide as a Novel Cardiac Hormone in Humans," *J. Clin. Invest.*, 87:1402-1412 (1991).

Murdoch, et al., "Brain natriuretic peptide is stable in whole blood and can be measured using a simple rapid assay: implications for clinical practice," *Heart*, 78:594-597 (1997).

Nordin, et al., "Kinetic studies of small molecule interactions with protein kinases using biosensor technology," *Analytical Biochem.*, 340:359-368 (2005).

PCT International Application No. PCT/US2006/0043608, Transmittal of The International Search Report and The Written Opinion of The International Searching Authority, Mailed Mar. 23, 2007.

Rajpal, et al., "A general method for greatly improving the affinity of antibodies by using combinatorial libraries," *PNAS*, 102(24):8466-8471 (2005).

Sanz, et al., "Comparison of BNP and NT-proBNP Assays in the Approach to the Emergency Diagnosis of Actue Dyspnea," *J. of Clin. Lab. Analysis*, 20:227-232 (2006).

Schiestl, et al., "High efficiency transformation of intact yeast cells using single stranded nucleic acids as a carrier," *Curr. Genet.*, 16:339-346 (1989).

Shimizu, et al., "Degradation of human brain natriuretic peptide (BNP) by contact activation of blood coagulation system," *Clinica Chimica Acta*, 305:181-186 (2001).

Shimizu, et al., "Molecular forms of human brain natriuretic peptide in plasma," *Clinica Chimica Acta*, 316:129-135 (2002).

Tetin, et al., "Interactions of Two Monclonal Antibodies with BNP: High Resolution Epitope Mapping Using Fluorescence Correlation Spectroscopy," *Biochem.*, 45:14155-14165 (2006).

Thorpe, et al., "Clonal Analysis of a Human Antimouse Antibody (HAMA) Response," *Scandinavian J. of Immunol.*, 57:85-92 (2003).

Urlaub, et al., "Isolation of Chinese hamster cell mutants deficient in dihydrofolate reductase activity," *PNAS.*, 77(7):4216-4220 (1980).

Valli, et al., "Review of 10 years of the clinical use of brain natriuretic peptide in cardiology," *J. Lab. Clin. Med.*, 134(5):437-444 (1999).

Von Mehren, et al., "Monoclonal antibody-based therapy," *Current Opinion in Oncology*, 8:493-498, 1996.

Walther, et al., "Biochemical analysis of netural endopeptidase activity reveals independent catabolism of atrial and brain natriuretic peptide," *Biol. Chem.*, 385:179-184 (2004).

Watanabe, et al., "Prognostic Value of Plasma Brain Natriuretic Peptide Combined With Left Ventricular Dimensions in Predicting Sudden Death of Patients With Chronic Heart Failure," *J. of Cardiac Failure*, 11(1):50-55 (2005).

Yandle, "Biochemistry of natriuretic peptides," *J. of Int. Med.*, 235:561-576 (1994).

Yoshibayashi, et al., "Increased Plasma Levels of Brain Natriuretic Peptide in Hypertrophic Cardiomyopathy," *The New England J. of Med.*, 329(6):433-434 (1993).

Zahnd, et al., "Directed in Vitro Evolution and Crystallographic Analysis of a Peptide-binding Single Chain Antibody Fragment (scFv) with Low Picomolar Affinity," *J. of Biol. Chem.*, 279(18):18870-18877 (2004).

Fuchs, H., et al., "The result of equilibrium-constant calculations strongly depends on the evaluation method used and on the type of experimental errors," Biochemical Journal 20011015 Portland Press, Ltd., vol. 359, No. 2, Oct. 15, 2001, pp. 411-418.

Supplementary European Search Report for European Application No. EP 08747818, dated Feb. 11, 2011.

\* cited by examiner

FIGURE 3A

```
1    ACGGATTAGAAG CCGCCGAGCGGG TGACAGCCCTCC
37   GAAGGAAGACTC TCCTCCGTGCGT CCTCGTCCTCAC
73   CGGTCGCGTTCC TGAAACGCAGAT GTGCCTCGCGCC
109  GCACTGCTCCGA ACAATAAAGATT CTACAATACTAG
145  CTTTTATGGTTA TGAAGAGGAAAA ATTGGCAGTAAC
181  CTGGCCCCACAA ACCTTCAAATGA ACGAATCAAATT
217  AACAACCATAGG ATGATAATGCGA TTAGTTTTTTAG
253  CCTTATTTCTGG GGTAATTAATCA GCGAAGCGATGA
289  TTTTTGATCTAT TAACAGATATAT AAATGCAAAAAC
325  TGCATTAACCAC TTTAACTAATAC TTTCAACATTTT
361  CGGTTTGTATTA CTTCTTATTCAA ATGTAATAAAAG
397  TATCAACAAAAA ATTGTTAATATA CCTCTATACTTT
433  AACGTCAAGGAG AAAAAACCCCGG ATCGGACTACTA
469  GCAGCTGTAATA CGACTCACTATA GGGAATATTAAG
                                      AGA2
505  CTAATTCTACTT CATACATTTTCA ATTAAGATGCAG
     ------------------AGA2------------------
541  TTACTTCGCTGT TTTTCAATATTT TCTGTTATTGCT
     ------------------AGA2------------------
577  TCAGTTTTAGCA CAGGAACTGACA ACTATATGCGAG
     ------------------AGA2------------------
613  CAAATCCCCTCA CCAACTTTAGAA TCGACGCCGTAC
     ------------------AGA2------------------
649  TCTTTGTCAACG ACTACTATTTTG GCCAACGGGAAG
     ------------------AGA2------------------
685  GCAATGCAAGGA GTTTTTGAATAT TACAAATCAGTA
     ------------------AGA2------------------
721  ACGTTTGTCAGT AATTGCGGTTCT CACCCCTCAACA
     ------------------AGA2------------------
757  ACTAGCAAAGGC AGCCCCATAAAC ACACAGTATGTT
     ---             Tether 41-------
793  TTTAAGCTTCTG CAGGCTAGTGGT GAGAACAAGGTG
     -------------------------Tether41
829  GAGTACGCGCCG GCGTTGATGGCC TTGTCTGCTAGC
865  ATGACTGGTGGA CAGCAAATGGGT CGGGATCTGTAC
901  GACGATGACGAT AAGGTACCAGGA TCCAGTGTGGTG
                                      106.3
937  GAATTCGCGGCC CAGCCGGCCATG GCCCAGATCCAG
     variable heavy----------------------
973  TTGGTGCAGTCT GGACCTGAGCTG AGGAAGCCTGGA
     ----------------------------------------
1009 GAGACAGTCAAG ATCTCCTGCAAG GGTTCTGGATAT
     ----------------------------------------
```

FIGURE 3B

```
1045  ACCTTCACACAC TATGGAATAAAC TGGGTGAAGCAG
      ------------------------------------
1081  ACTCCAAGAAAG GATTTAAAGTGG ATGGGCTGGATA
      ------------------------------------
1117  AACACCCATACT GGAGAGCCAATA TATGCTGATGAC
      ------------------------------------
1153  TTCAAGGGACGG TTTGCCTTCTCT TTGGAAACCTCT
      ------------------------------------
1189  GCCAACACTGCC TATTTGCAAATC AACAACCTCAAC
      ------------------------------------
1225  AATGGAGACATG GTACATATTTC TGTACAAGAAGT
      ------------------------------------
1261  CACCGGTTTGGT TTGGACTACTGG GGTCAAGGTACC
      -------------VH end-Linker 40---------
1297  TCAGTCACCGTC TCGTCAGGTCCC GCCAAGGAGTTG
      --------------------------------106.3 ---
1333  ACGCCCCTGAAG GAGGCGAAGGTC TCTGACAATGTG
      Variable light-----------------------
1369  CTGACCCAATCT CCACCTTCTTTG GCTGTGTCTCTA
      ------------------------------------
1405  GGGCAGAGGGCC ACCATCTCCTGC AAGGCCAGCCAA
      ------------------------------------
1441  AGTGTTGATTAT AATGGTGATAGT TATCTGAACTGG
      ------------------------------------
1477  TACCAACAGAAG CCAGGACAGCCA CCCAAATTCCTC
      ------------------------------------
1513  ATCTATGCTGCA TCCAATCTAGAA TCTGGGATCCCA
      ------------------------------------
1549  GCCAGGTTTAGT GGCAGTGGGTCT GGGACAGACTTC
      ------------------------------------
1585  AACCTCAACATC CATCCTGTGGAG GAGGAGGATGCT
      ------------------------------------
1621  GCAACCTATTAC TGTCAGCAAAGT AATGAGGATCCA
      ------------------------------------
1657  TTCACGTTCGGC TCGGGGACAAAG TTGGAAATAAAA
      end
1693  CGGGCGGCCGCC CTCGAGTCTAGA GGGCCCTTCGAA
      V5 Epitope--------------------------
1729  GGTAAGCCTATC CCTAACCCTCTC CTCGGTCTCGAT
      ------        Six HIS tag-------STOP
1765  TCTACGCGTACC GGTCATCATCAC CATCACCATTGA
1801  GTTTAAACCCGC TGATCTGATAAC AACAGTGTAGAT
1837  GTAACAAAATCG ACTTTGTTCCCA CTGTACTTTTAG
```

FIGURE 3C

```
1873  CTCGTACAAAAT ACAATATACTTT TCATTTCTCCGT
1909  AAACAACATGTT TTCCCATGTAAT ATCCTTTTCTAT
1945  TTTTCGTTCCGT TACCAACTTTAC ACATACTTTATA
1981  TAGCTATTCACT TCTATACACTAA AAAACTAAGACA
2017  ATTTTAATTTTG CTGCCTGCCATA TTTCAATTTGTT
2053  ATAAATTCCTAT AATTTATCCTAT TAGTAGCTAAAA
2089  AAAGATGAATGT GAATCGAATCCT AAGAGAATTGGG
2125  CAAGTGCACAAA CAATACTTAAAT AAATACTACTCA
                       end TRP1 ORF
2161  GTAATAACCTAT TTCTTAGCATTT TTGACGAAATT
2197  GCTATTTTGTTA GAGTCTTTTACA CCATTTGTCTCC
2233  ACACCTCCGCTT ACATCAACACCA ATAACGCCATTT
2269  AATCTAAGCGCA TCACCAACATTT TCTGGCGTCAGT
2305  CCACCAGCTAAC ATAAAATGTAAG CTCTCGGGGCTC
2341  TCTTGCCTTCCA ACCCAGTCAGAA ATCGAGTTCCAA
2377  TCCAAAAGTTCA CCTGTCCCACCT GCTTCTGAATCA
2413  AACAAGGGAATA AACGAATGAGGT TTCTGTGAAGCT
2449  GCACTGAGTAGT ATGTTGCAGTCT TTTGGAAATACG
2485  AGTCTTTTAATA ACTGGCAAACCG AGGAACTCTTGG
2521  TATTCTTGCCAC GACTCATCTCCG TGCAGTTGGACG
2557  ATATCAATGCCG TAATCATTGACC AGAGCCAAAACA
2593  TCCTCCTTAGGT TGATTACGAAAC ACGCCAACCAAG
2629  TATTTCGGAGTG CCTGAACTATTT TTATATGCTTTT
2665  ACAAGACTTGAA ATTTTCCTTGCA ATAACCGGGTCA
2701  ATTGTTCTCTTT CTATTGGGCACA CATATAATACCC
2737  AGCAAGTCAGCA TCGGAATCTAGA GCACATTCTGCG
2773  GCCTCTGTGCTC TGCAAGCCGCAA ACTTTCACCAAT
2809  GGACCAGAACTA CCTGTGAAATTA ATAACAGACATA
                                    TRP1 ORF
2845  CTCCAAGCTGCC TTTGTGTGCTTA ATCACGTATACT
2881  CACGTGCTCAAT AGTCACCAATGC CCTCCCTCTTGG
2917  CCCTCTCCTTTT CTTTTTTCGACC GAATTTCTTGAA
2953  GACGAAAGGGCC TCGTGATACGCC TATTTTTATAGG
2989  TTAATGTCATGA TAATAATGGTTT CTTAGGACGGAT
3025  CGCTTGCCTGTA ACTTACACGCGC CTCGTATCTTTT
3061  AATGATGGAATA ATTTGGGAATTT ACTCTGTGTTTA
3097  TTTATTTTATG TTTTGTATTTGG ATTTTAGAAAGT
3133  AAATAAGAAGG TAGAAGAGTTAC GGAATGAAGAAA
3169  AAAAAATAAACA AAGGTTTAAAAA ATTTCAACAAAA
3205  AGCGTACTTTAC ATATATATTTAT TAGACAAGAAAA
3241  GCAGATTAAATA GATATACATTCG ATTAACGATAAG
3277  TAAAATGTAAAA TCACAGGATTTT CGTGTGTGGTCT
3313  TCTACACAGACA AGATGAAACAAT TCGGCATTAATA
3349  CCTGAGAGCAGG AAGAGCAAGATA AAAGGTAGTATT
3385  TGTTGGCGATCC CCCTAGAGTCTT TTACATCTTCGG
3421  AAAACAAAAACT ATTTTTTCTTTA ATTTCTTTTTT
3457  ACTTCTATTTT TAATTTATATAT TTATATTAAAAA
3493  ATTTAAATTATA ATTATTTTTATA GCACGTGATGAA
```

FIGURE 3D

```
3529  AAGGACCCAGGT  GGCACTTTTCGG  GGAAATGTGCGC
3565  GGAACCCCTATT  TGTTTATTTTTC  TAAATACATTCA
3601  AATATGTATCCG  CTCATGAGACAA  TAACCCTGATAA
              Amp Res---
3637  ATGCTTCAATAA  TATTGAAAAAGG  AAGAGTATGAGT
3673  ATTCAACATTTC  CGTGTCGCCCTT  ATTCCCTTTTTT
3709  GCGGCATTTTGC  CTTCCTGTTTTT  GCTCACCCAGAA
3745  ACGCTGGTGAAA  GTAAAAGATGCT  GAAGATCAGTTG
3781  GGTGCACGAGTG  GGTTACATCGAA  CTGGATCTCAAC
3817  AGCGGTAAGATC  CTTGAGAGTTTT  CGCCCCGAAGAA
3853  CGTTTTCCAATG  ATGAGCACTTTT  AAAGTTCTGCTA
3889  TGTGGCGCGGTA  TTATCCCGTGTT  GACGCCGGGCAA
3925  GAGCAACTCGGT  CGCCGCATACAC  TATTCTCAGAAT
3961  GACTTGGTTGAG  TACTCACCAGTC  ACAGAAAGCAT
3997  CTTACGGATGGC  ATGACAGTAAGA  GAATTATGCAGT
4033  GCTGCCATAACC  ATGAGTGATAAC  ACTGCGGCCAAC
4069  TTACTTCTGACA  ACGATCGGAGGA  CCGAAGGAGCTA
4105  ACCGCTTTTTG   CACAACATGGGG  GATCATGTAACT
4141  CGCCTTGATCGT  TGGGAACCGGAG  CTGAATGAAGCC
4177  ATACCAAACGAC  GAGCGTGACACC  ACGATGCCTGTA
4213  GCAATGGCAACA  ACGTTGCGCAAA  CTATTAACTGGC
4249  GAACTACTTACT  CTAGCTTCCCGG  CAACAATTAATA
4285  GACTGGATGGAG  GCGGATAAAGTT  GCAGGACCACTT
4321  CTGCGCTCGGCC  CTTCCGGCTGGC  TGGTTTATTGCT
4357  GATAAATCTGGA  GCCGGTGAGCGT  GGGTCTCGCGGT
4393  ATCATTGCAGCA  CTGGGGCCAGAT  GGTAAGCCCTCC
4429  CGTATCGTAGTT  ATCTACACGACG  GGCAGTCAGGCA
4465  ACTATGGATGAA  CGAAATAGACAG  ATCGCTGAGATA
              Amp Res end
4501  GGTGCCTCACTG  ATTAAGCATTGG  TAACTGTCAGAC
4537  CAAGTTTACTCA  TATATACTTTAG  ATTGATTTAAAA
4573  CTTCATTTTTAA  TTTAAAAGGATC  TAGGTGAAGATC
4609  CTTTTTGATAAT  CTCATGACCAAA  ATCCCTTAACGT
4645  GAGTTTTCGTTC  CACTGAGCGTCA  GACCCCGTAGAA
4681  AAGATCAAAGGA  TCTTCTTGAGAT  CCTTTTTTTCTG
4717  CGCGTAATCTGC  TGCTTGCAAACA  AAAAAACCACCG
4753  CTACCAGCGGTG  GTTTGTTTGCCG  GATCAAGAGCTA
4789  CCAACTCTTTTT  CCGAAGGTAACT  GGCTTCAGCAGA
4825  GCGCAGATACCA  AATACTGTCCTT  CTAGTGTAGCCG
4861  TAGTTAGGCCAC  CACTTCAAGAAC  TCTGTAGCACCG
4897  CCTACATACCTC  GCTCTGCTAATC  CTGTTACCAGTG
4933  GCTGCTGCCAGT  GGCGATAAGTCG  TGTCTTACCGGG
4969  TTGGACTCAAGA  CGATAGTTACCG  GATAAGGCGCAG
5005  CGGTCGGGCTGA  ACGGGGGGTTCG  TGCACACAGCCC
5041  AGCTTGGAGCGA  ACGACCTACACC  GAACTGAGATAC
5077  CTACAGCGTGAG  CATTGAGAAAGC  GCCACGCTTCCC
5113  GAAGGGAGAAAG  GCGGACAGGTAT  CCGGTAAGCGGC
```

FIGURE 3E

```
5149    AGGGTCGGAACA  GGAGAGCGCACG  AGGGAGCTTCCA
5185    GGGGGGAACGCC  TGGTATCTTTAT  AGTCCTGTCGGG
5221    TTTCGCCACCTC  TGACTTGAGCGT  CGATTTTTGTGA
5257    TGCTCGTCAGGG  GGGCCGAGCCTA  TGGAAAAACGCC
5293    AGCAACGCGGCC  TTTTTACGGTTC  CTGGCCTTTTGC
5329    TGGCCTTTTGCT  CACATGTTCTTT  CCTGCGTTATCC
5365    CCTGATTCTGTG  GATAACCGTATT  ACCGCCTTTGAG
5401    TGAGCTGATACC  GCTCGCCGCAGC  CGAACGACCGAG
5437    CGCAGCGAGTCA  GTGAGCGAGGAA  GCGGAAGAGCGC
5473    CCAATACGCAAA  CCGCCTCTCCCC  GCGCGTTGGCCG
5509    ATTCATTAATGC  AGCTGGCACGAC  AGGTTTCCCGAC
5545    TGGAAAGCGGGC  AGTGAGCGCAAC  GCAATTAATGTG
5581    AGTTACCTCACT  CATTAGGCACCC  CAGGCTTTACAC
5617    TTTATGCTTCCG  GCTCCTATGTTG  TGTGGAATTGTG
5653    AGCGGATAACAA  TTTCACACAGGA  AACAGCTATGAC
5689    CATGATTACGCC  AAGCTCGGAATT  AACCCTCACTAA
5725    AGGGAACAAAAG  CTGGCTAGT
```

FIGURE 5

QLVQSGPELR KPGETVKISC KGSGYTFTHY GINWVKQTPR KDLKWMGWIN

THTGEPIYAD DFKGRFAFSL ETSANTAYLQ INNLNNGDMG TYFCTRSHRF

GLDYWGQGTS VTVSSGPAKE LTPLKEAKVS DNVLTQSPPS LAVSLGQRAT

ISCKASQSVD YNGDSYLNWY QQKPGQPPKF LIYAASNLES GIPARFSGSG

SGTDFNLNIH PVEEEDAATY YCQQSNEDPF TFGSGTKLEI KRAAALESRG

PFEGKPIPNP LLGLDSTRTG HHHHHH*

FIGURE 6A

```
                        106.3 Variable heavy
946                     CAGATCCAG TTGGTGCAG TCTGGACCT
                        GTCTAGGTC AACCACGTC AGACCTGGA 106.3 Variable heavy
991   GAGCTGAGG AAGCCTGGA GAGACAGTC AAGATCTCC TGCAAGGGT
      CTCGACTCC TTCGGACCT CTCTGTCAG TTCTAGAGG ACGTTCCCA CDR H1----------------------(10)
                      106.3 Variable heavy
1036  TCTGGATAT ACCTTCACA CACTATGGA ATAAACTGG GTGAAGCAG
      AGACCTATA TGGAAGTGT GTGATACCT TATTTGACC CACTTCGTC CDR H2----------
                  106.3 Variable heavy
1081  ACTCCAAGA AAGGATTTA AAGTGGATG GGCTGGATA AACACCCAT
      TGAGGTTCT TTCCTAAAT TTCACCTAC CCGACCTAT TTGTGGGTA H2------------------------------------(17)
                      106.3 Variable heavy
1126  ACTGGAGAG CCAATATAT GCTGATGAC TTCAAGGGA CGGTTTGCC
      TGACCTCTC GGTTATATA CGACTACTG AAGTTCCCT GCCAAACGG 106.3 Variable heavy
1171  TTCTCTTTG GAAACCTCT GCCAACACT GCCTATTTG CAAATCAAC
      AAGAGAAAC CTTTGGAGA CGGTTGTGA CGGATAAAC GTTTAGTTG CDR H3
                   106.3 Variable heavy
1216  AACCTCAAC AATGGAGAC ATGGGTACA TATTTCTGT ACAAGAAGT
      TTGGAGTTG TTACCTCTG TACCCATGT ATAAAGACA TGTTCTTCA H3------------------(8)
                   106.3 Variable heavy
1261  CACCGGTTT GGTTTGGAC TACTGGGGT CAAGGTACC TCAGTCACC
      GTGGCCAAA CCAAACCTG ATGACCCCA GTTCCATGG AGTCAGTGG 106.3 Vh
              Linker 40--------------------------------
1306  GTCTCGTCA GGTCCCGCC AAGGAGTTG ACGCCCCTG AAGGAGGCG
      CAGAGCAGT CCAGGGCGG TTCCTCAAC TGCGGGGAC TTCCTCCGC 106.3 Variable light
      Linker 40
1351  AAGGTCTCT GACAATGTG CTGACCCAA TCTCCACCT TCTTTGGCT
      TTCCAGAGA CTGTTACAC GACTGGGTT AGAGGTGGA AGAAACCGA CDR L1-------
                   106.3 Variable light
1396  GTGTCTCTA GGGCAGAGG GCCACCATC TCCTGCAAG GCCAGCCAA
      CACAGAGAT CCCGTCTCC CGGTGGTAG AGGACGTTC CGGTCGGTT CDR L1--------------------------(15)
                   106.3 Variable light
1441  AGTGTTGAT TATAATGGT GATAGTTAT CTGAACTGG TACCAACAG
      TCACAACTA ATATTACCA CTATCAATA GACTTGACC ATGGTTGTC
```

FIGURE 6B

```
                                              CDR L2-------
              106.3 Variable light
1486   AAGCCAGGA CAGCCACCC AAATTCCTC ATCTATGCT GCATCCAAT
       TTCGGTCCT GTCGGTGGG TTTAAGGAG TAGATACGA CGTAGGTTA ------(7)
              106.3 Variable light
1531   CTAGAATCT GGGATCCCA GCCAGGTTT AGTGGCAGT GGGTCTGGG
       GATCTTAGA CCCTAGGGT CGGTCCAAA TCACCGTCA CCCAGACCC 106.3 Variable light
1576   ACAGACTTC AACCTCAAC ATCCATCCT GTGGAGGAG GAGGATGCT
       TGTCTGAAG TTGGAGTTG TAGGTAGGA CACCTCCTC CTCCTACGA CDR L3--------------------(9)
              106.3 Variable light
1621   GCAACCTAT TACTGTCAG CAAAGTAAT GAGGATCCA TTCACGTTC
       CGTTGGATA ATGACAGTC GTTTCATTA CTCCTAGGT AAGTGCAAG 106.3 Variable light
                                  end    NotI
1666   GGCTCGGGG ACAAAGTTG GAAATAAAA CGGGCGGCC GCCCTCGAG
       CCGAGCCCC TGTTTCAAC CTTTATTTT GCCCGCCGG CGGGAGCTC V5 Epitope
1711   TCTAGAGGG CCCTTCGAA GGTAAGCCT ATCCCTAAC CCTCTCCTC
       AGATCTCCC GGGAAGCTT CCATTCGGA TAGGGATTG GGAGAGGAG V5 Epitope                          poly HIS
1756   GGTCTCGAT TCTACGCGT ACCGGTCAT CATCACCAT CACCATTGA
       CCAGAGCTA AGATGCGCA TGGCCAGTA GTAGTGGTA GTGGTAACT
```

FIGURE 11

| Name | $k_{off}$ (sec$^{-1}$) | Fold Improvement |
|---|---|---|
| 106.3 wt | 8.4E-05 | ----- |
| H2 288 | 3.7E-05 | 2.3 |
| L1 B4 | 7.3E-06 | 11.5 |
| L1 B9 | 3.1E-05 | 2.7 |
| L1 9b | 1.3E-05 | 6.4 |
| L1 B12 | 7.6E-06 | 11.0 |
| L1 B15 | 8.6E-06 | 9.7 |
| L1 16 | 8.7E-06 | 9.6 |
| L1 B24 | 6.7E-06 | 12.5 |
| L2 6 | 3.2E-05 | 2.7 |
| L2 21 | 4.0E-05 | 2.1 |

FIGURE 12A

| Name | CDR H2 Pos 56 | CDR H2 Pos 57 | CDR H2 Pos 58 |
|---|---|---|---|
| 106.3 wt | Glu (GAG) | Pro (CCA) | Ile (ATA) |
| H2 288 | Glu (GAG) | Ala (GCG) | Tyr (TAC) |

FIGURE 12B

| Name | CDR L1 Pos 26 | CDR L1 Pos 27 | CDR L1 Pos 27A | Other Mutations |
|---|---|---|---|---|
| 106.3 wt | Ser (AGC) | Gln (CAA) | Ser (AGT) | |
| L1 B4 | Gln (CAG) | Phe (TTC) | Ala (GCG) | |
| L1 B9 | Tyr (TAC) | Ala (GCG) | Ser (AGT) | |
| L1 9b | Gln (CAG) | Trp (TGG) | Gly (GGC) | R42S |
| L1 B12 | Thr (ACC) | Trp (TGG) | Asp (GAC) | |
| L1 B15 | Arg (AGG) | Trp (TGG) | Pro (CCG) | |
| L1 16 | Ala (GCG) | Tyr (TAC) | Gly (GGC) | |
| L1 B24 | Asn (AAC) | Trp (TGG) | Pro (CCC) | R42S |

FIGURE 12C

| Name | CDR L2 Pos 53 | CDR L2 Pos 54 | CDR L2 Pos 55 |
|---|---|---|---|
| 106.3 wt | Asn (AAT) | Leu (CTA) | Glu (GAA) |
| L2 6 | Cys (TGC) | Gly (GGG) | Trp (TGG) |
| L2 21 | Cys (TGC) | Ala (GCG) | Pro (CCG) |

FIGURE 13

| Clone Name | Antibody Type | $k_{on}$ ($M^{-1}sec^{-1}$) | $k_{off}$ ($sec^{-1}$) | $K_D$ (pM) |
|---|---|---|---|---|
| 106.3 wt | Mouse IgG1 | 1.2E+07 | 2.2E-04 | 18 |
| 106.3 wt | Mouse-Human IgG1 | 7.8E+06 | 1.5E-04 | 19 |
| 106.3 AM1 | Mouse-Human IgG1 | 1.3E+07 | 2.4E-05 | 1.9 |

FIGURE 14A

Degenerate Oligonucleotides:
N= A, G, C, T; S = G, C

CDR H3 Degenerate Oligonucleotides

| System | Code | CDR | Library name | Length(ntd) |
|---|---|---|---|---|
| 106.3 | Oligo1 | H3 | H3-1 | 105 |
| 106.3 | Oligo 2 | H3 | H3-2 | 105 |
| 106.3 | Oligo 3 | H3 | H3-3 | 105 |
| 106.3 | Oligo 4 | H3 | H3-4 | 105 |
| 106.3 | Oligo 5 | H3 | H3-5 | 105 |
| 106.3 | Oligo 6 | H3 | H3-6 | 99 |

Oligo1
   AAC CTC AAC AAT GGA GAC ATG GGT ACA TAT TTC TGT ACA AGA NNS NNS NNS TTT GGT TTG GAC TAC TGG GGT CAA GGT ACC TCA GTC ACC GTC TCG TCA GGT CCC Oligo2
   AAC CTC AAC AAT GGA GAC ATG GGT ACA TAT TTC TGT ACA AGA AGT NNS NNS NNS GGT TTG GAC TAC TGG GGT CAA GGT ACC TCA GTC ACC GTC TCG TCA GGT CCC Oligo3
   AAC CTC AAC AAT GGA GAC ATG GGT ACA TAT TTC TGT ACA AGA AGT CAC NNS NNS NNS TTG GAC TAC TGG GGT CAA GGT ACC TCA GTC ACC GTC TCG TCA GGT CCC Oligo 4
   AAC CTC AAC AAT GGA GAC ATG GGT ACA TAT TTC TGT ACA AGA AGT CAC CGG NNS NNS NNS GAC TAC TGG GGT CAA GGT ACC TCA GTC ACC GTC TCG TCA GGT CCC Oligo 5
   AAC CTC AAC AAT GGA GAC ATG GGT ACA TAT TTC TGT ACA AGA AGT CAC CGG TTT NNS NNS NNS TAC TGG GGT CAA GGT ACC TCA GTC ACC GTC TCG TCA GGT CCC Oligo 6
   GAC ATG GGT ACA TAT TTC TGT ACA AGA AGT CAC CGG TTT GGT NNS NNS NNS TGG GGT CAA GGT ACC TCA GTC ACC GTC TCG TCA GGT CCC GCC GCC AAG

FIGURE 14B

H2 Degenerate Oligonucleotides

| System | Code | CDR | Library name | Length(ntd) |
|---|---|---|---|---|
| 106.3 | Oligo 7 | H2 | H2-1 | 105 |
| 106.3 | Oligo 8 | H2 | H2-2 | 105 |
| 106.3 | Oligo 9 | H2 | H2-3 | 105 |
| 106.3 | Oligo10 | H2 | H2-4 | 105 |
| 106.3 | Oligo11 | H2 | H2-5 | 105 |
| 106.3 | Oligo12 | H2 | H2-6 | 105 |
| 106.3 | Oligo 13 | H2 | H2-7 | 105 |
| 106.3 | Oligo 14 | H2 | H2-8 | 105 |
| 106.3 | Oligo 15 | H2 | H2-9 | 105 |
| 106.3 | Oligo 16 | H2 | H2-10 | 105 |
| 106.3 | Oligo 17 | H2 | H2-11 | 105 |
| 106.3 | Oligo 18 | H2 | H2-12 | 105 |
| 106.3 | Oligo 19 | H2 | H2-13 | 105 |
| 106.3 | Oligo 20 | H2 | H2-14 | 105 |
| 106.3 | Oligo 21 | H2 | H2-15 | 105 |

Oligo 7
　TGG GTG AAG CAG ACT CCA AGA AAG GAT TTA AAG TGG ATG GGC NNS NNS NNS ACC CAT ACT GGA GAG CCA ATA TAT GCT GAT GAC TTC AAG GGA CGG TTT GCC TTC Oligo 8
　TGG GTG AAG CAG ACT CCA AGA AAG GAT TTA AAG TGG ATG GGC TGG NNS NNS NNS CAT ACT GGA GAG CCA ATA TAT GCT GAT GAC TTC AAG GGA CGG TTT GCC TTC Oligo 9
　TGG GTG AAG CAG ACT CCA AGA AAG GAT TTA AAG TGG ATG GGC TGG ATA NNS NNS NNS ACT GGA GAG CCA ATA TAT GCT GAT GAC TTC AAG GGA CGG TTT GCC TTC Oligo 10
　TGG GTG AAG CAG ACT CCA AGA AAG GAT TTA AAG TGG ATG GGC TGG ATA AAC NNS NNS NNS GGA GAG CCA ATA TAT GCT GAT GAC TTC AAG GGA CGG TTT GCC TTC Oligo 11
　TGG GTG AAG CAG ACT CCA AGA AAG GAT TTA AAG TGG ATG GGC TGG ATA AAC ACC NNS NNS NNS GAG CCA ATA TAT GCT GAT GAC TTC AAG GGA CGG TTT GCC TTC Oligo 12
　CCA AGA AAG GAT TTA AAG TGG ATG GGC TGG ATA AAC ACC CAT NNS NNS NNS CCA ATA TAT GCT GAT GAC TTC AAG GGA CGG TTT GCC TTC TCT TTG GAA ACC TCT

FIGURE 14C

Oligo 13
  CCA AGA AAG GAT TTA AAG TGG ATG GGC **TGG ATA AAC ACC CAT ACT
  NNS NNS NNS ATA TAT GCT GAT GAC TTC AAG GGA** CGG TTT GCC TTC
  TCT TTG GAA ACC TCT Oligo 14
  CCA AGA AAG GAT TTA AAG TGG ATG GGC **TGG ATA AAC ACC CAT ACT
  GGA NNS NNS NNS TAT GCT GAT GAC TTC AAG GGA** CGG TTT GCC TTC
  TCT TTG GAA ACC TCT Oligo15
  CCA AGA AAG GAT TTA AAG TGG ATG GGC **TGG ATA AAC ACC CAT ACT
  GGA GAG NNS NNS NNS GCT GAT GAC TTC AAG GGA** CGG TTT GCC TTC
  TCT TTG GAA ACC TCT Oligo16
  CCA AGA AAG GAT TTA AAG TGG ATG GGC **TGG ATA AAC ACC CAT ACT
  GGA GAG CCA NNS NNS NNS GAT GAC TTC AAG GGA** CGG TTT GCC TTC
  TCT TTG GAA ACC TCT Oligo17
  AAG TGG ATG GGC **TGG ATA AAC ACC CAT ACT GGA GAG CCA ATA NNS
  NNS NNS GAC TTC AAG GGA** CGG TTT GCC TTC TCT TTG GAA ACC TCT
  GCC AAC ACT GCC TAT Oligo18
  AAG TGG ATG GGC **TGG ATA AAC ACC CAT ACT GGA GAG CCA ATA TAT
  NNS NNS NNS TTC AAG GGA** CGG TTT GCC TTC TCT TTG GAA ACC TCT
  GCC AAC ACT GCC TAT Oligo19
  AAG TGG ATG GGC **TGG ATA AAC ACC CAT ACT GGA GAG CCA ATA TAT
  GCT NNS NNS NNS AAG GGA** CGG TTT GCC TTC TCT TTG GAA ACC TCT
  GCC AAC ACT GCC TAT Oligo20
  AAG TGG ATG GGC **TGG ATA AAC ACC CAT ACT GGA GAG CCA ATA TAT
  GCT GAT NNS NNS NNS GGA** CGG TTT GCC TTC TCT TTG GAA ACC TCT
  GCC AAC ACT GCC TAT Oligo21
  AAG TGG ATG GGC **TGG ATA AAC ACC CAT ACT GGA GAG CCA ATA TAT
  GCT GAT GAC NNS NNS NNS** CGG TTT GCC TTC TCT TTG GAA ACC TCT
  GCC AAC ACT GCC TAT

FIGURE 14D

CDR H1 Degenerate Oligonucleotides

| System | Code | CDR | Library name | Length(ntd) |
|---|---|---|---|---|
| 106.3 | Oligo22 | H1 | H1-1 | 105 |
| 106.3 | Oligo23 | H1 | H1-2 | 105 |
| 106.3 | Oligo24 | H1 | H1-3 | 105 |
| 106.3 | Oligo25 | H1 | H1-4 | 105 |
| 106.3 | Oligo26 | H1 | H1-5 | 105 |
| 106.3 | Oligo27 | H1 | H1-6 | 99 |
| 106.3 | Oligo28 | H1 | H1-7 | 99 |
| 106.3 | Oligo29 | H1 | H1-8 | 99 |

Oligo22
   AGG AAG CCT GGA GAG ACA GTC AAG ATC TCC TGC AAG GGT TCT NNS NNS NNS TTC ACA CAC TAT GGA ATA AAC TGG GTG AAG CAG ACT CCA AGA AAG GAT TTA AAG Oligo23
   AGG AAG CCT GGA GAG ACA GTC AAG ATC TCC TGC AAG GGT TCT GGA NNS NNS NNS ACA CAC TAT GGA ATA AAC TGG GTG AAG CAG ACT CCA AGA AAG GAT TTA AAG Oligo24
   AGG AAG CCT GGA GAG ACA GTC AAG ATC TCC TGC AAG GGT TCT GGA TAT NNS NNS NNS CAC TAT GGA ATA AAC TGG GTG AAG CAG ACT CCA AGA AAG GAT TTA AAG Oligo25
   AGG AAG CCT GGA GAG ACA GTC AAG ATC TCC TGC AAG GGT TCT GGA TAT ACC NNS NNS NNS TAT GGA ATA AAC TGG GTG AAG CAG ACT CCA AGA AAG GAT TTA AAG Oligo26
   AGG AAG CCT GGA GAG ACA GTC AAG ATC TCC TGC AAG GGT TCT GGA TAT ACC TTC NNS NNS NNS GGA ATA AAC TGG GTG AAG CAG ACT CCA AGA AAG GAT TTA AAG Oligo27
   ACA GTC AAG ATC TCC TGC AAG GGT TCT GGA TAT ACC TTC ACA NNS NNS NNS ATA AAC TGG GTG AAG CAG ACT CCA AGA AAG GAT TTA AAG TGG ATG GGC Oligo28
   ACA GTC AAG ATC TCC TGC AAG GGT TCT GGA TAT ACC TTC ACA CAC NNS NNS NNS AAC TGG GTG AAG CAG ACT CCA AGA AAG GAT TTA AAG TGG ATG GGC Oligo29
   ACA GTC AAG ATC TCC TGC AAG GGT TCT GGA TAT ACC TTC ACA CAC TAT NNS NNS NNS TGG GTG AAG CAG ACT CCA AGA AAG GAT TTA AAG TGG ATG GGC

FIGURE 14E

CDR L1 Degenerate Oligonucleotides (13)

| System | Code | CDR | Library name | Length(ntd) |
|---|---|---|---|---|
| 106.3 | Oligo30 | L1 | L1-1 | 99 |
| 106.3 | Oligo31 | L1 | L1-2 | 99 |
| 106.3 | Oligo32 | L1 | L1-3 | 99 |
| 106.3 | Oligo33 | L1 | L1-4 | 99 |
| 106.3 | Oligo34 | L1 | L1-5 | 99 |
| 106.3 | Oligo35 | L1 | L1-6 | 99 |
| 106.3 | Oligo36 | L1 | L1-7 | 99 |
| 106.3 | Oligo37 | L1 | L1-8 | 99 |
| 106.3 | Oligo38 | L1 | L1-9 | 99 |
| 106.3 | Oligo39 | L1 | L1-10 | 99 |
| 106.3 | Oligo40 | L1 | L1-11 | 99 |
| 106.3 | Oligo41 | L1 | L1-12 | 93 |
| 106.3 | Oligo42 | L1 | L1-13 | 93 |

Oligo 30
  TTG GCT GTG TCT CTA GGG CAG AGG GCC ACC ATC TCC TGC NNS NNS NNS CAA AGT GTT GAT TAT AAT GGT GAT AGT TAT CTG AAC TGG TAC CAA CAG AAG Oligo 31
  TTG GCT GTG TCT CTA GGG CAG AGG GCC ACC ATC TCC TGC AAG NNS NNS NNS AGT GTT GAT TAT AAT GGT GAT AGT TAT CTG AAC TGG TAC CAA CAG AAG Oligo 32
  TTG GCT GTG TCT CTA GGG CAG AGG GCC ACC ATC TCC TGC AAG GCC NNS NNS NNS GTT GAT TAT AAT GGT GAT AGT TAT CTG AAC TGG TAC CAA CAG AAG Oligo 33
  TTG GCT GTG TCT CTA GGG CAG AGG GCC ACC ATC TCC TGC AAG GCC AGC NNS NNS NNS GAT TAT AAT GGT GAT AGT TAT CTG AAC TGG TAC CAA CAG AAG Oligo 34
  TTG GCT GTG TCT CTA GGG CAG AGG GCC ACC ATC TCC TGC AAG GCC AGC CAA NNS NNS NNS TAT AAT GGT GAT AGT TAT CTG AAC TGG TAC CAA CAG AAG Oligo 35
  GGG CAG AGG GCC ACC ATC TCC TGC AAG GCC AGC CAA AGT NNS NNS NNS AAT GGT GAT AGT TAT CTG AAC TGG TAC CAA CAG AAG CCA GGA CAG CCA CCC

FIGURE 14F

Oligo 36
  GGG CAG AGG GCC ACC ATC TCC TGC **AAG GCC AGC CAA AGT GTT NNS
NNS NNS GGT GAT AGT TAT CTG AAC** TGG TAC CAA CAG AAG CCA GGA
CAG CCA CCC Oligo 37
  GGG CAG AGG GCC ACC ATC TCC TGC **AAG GCC AGC CAA AGT GTT GAT
NNS NNS NNS GAT AGT TAT CTG AAC** TGG TAC CAA CAG AAG CCA GGA
CAG CCA CCC Oligo38
  GGG CAG AGG GCC ACC ATC TCC TGC **AAG GCC AGC CAA AGT GTT GAT
TAT NNS NNS NNS AGT TAT CTG AAC** TGG TAC CAA CAG AAG CCA GGA
CAG CCA CCC Oligo39
  GGG CAG AGG GCC ACC ATC TCC TGC **AAG GCC AGC CAA AGT GTT GAT
TAT AAT NNS NNS NNS TAT CTG AAC** TGG TAC CAA CAG AAG CCA GGA
CAG CCA CCC Oligo40
  ATC TCC TGC **AAG GCC AGC CAA AGT GTT GAT TAT AAT GGT NNS NNS
NNS CTG AAC** TGG TAC CAA CAG AAG CCA GGA CAG CCA CCC AAA TTC
CTC Oligo41
  ATC TCC TGC **AAG GCC AGC CAA AGT GTT GAT TAT AAT GGT GAT NNS
NNS NNS AAC** TGG TAC CAA CAG AAG CCA GGA CAG CCA CCC AAA TTC
CTC Oligo42
  ATC TCC TGC **AAG GCC AGC CAA AGT GTT GAT TAT AAT GGT GAT AGT
NNS NNS NNS** TGG TAC CAA CAG AAG CCA GGA CAG CCA CCC AAA TTC
CTC

CDR L2 Degenerate Oligonucleotides (5)

| System | Code | CDR | Library name | Length(ntd) |
|---|---|---|---|---|
| 106.3 | Oligo43 | L2 | L2-1 | 99 |
| 106.3 | Oligo44 | L2 | L2-2 | 99 |
| 106.3 | Oligo45 | L2 | L2-3 | 99 |
| 106.3 | Oligo46 | L2 | L2-4 | 99 |
| 106.3 | Oligo47 | L2 | L2-5 | 99 |

Oligo43
  CAA CAG AAG CCA GGA CAG CCA CCC AAA TTC CTC ATC TAT **NNS NNS
NNS AAT CTA GAA TCT** GGG ATC CCA GCC AGG TTT AGT GGC AGT GGG
TCT GGG ACA Oligo44
  CAA CAG AAG CCA GGA CAG CCA CCC AAA TTC CTC ATC TAT **GCT NNS
NNS NNS CTA GAA TCT** GGG ATC CCA GCC AGG TTT AGT GGC AGT GGG
TCT GGG ACA

FIGURE 14G

Oligo45
   CAA CAG AAG CCA GGA CAG CCA CCC AAA TTC CTC ATC TAT **GCT GCA
   NNS NNS NNS GAA TCT** GGG ATC CCA GCC AGG TTT AGT GGC AGT GGG
   TCT GGG ACA Oligo46
   CAA CAG AAG CCA GGA CAG CCA CCC AAA TTC CTC ATC TAT **GCT GCA
   TCC NNS NNS NNS TCT** GGG ATC CCA GCC AGG TTT AGT GGC AGT GGG
   TCT GGG ACA Oligo47
   CAA CAG AAG CCA GGA CAG CCA CCC AAA TTC CTC ATC TAT **GCT GCA
   TCC AAT NNS NNS NNS** GGG ATC CCA GCC AGG TTT AGT GGC AGT GGG
   TCT GGG ACA

CDR L3 Degenerate Oligonucleotides (7)

| System | Code | CDR | Library name | Length(ntd) |
|---|---|---|---|---|
| 106.3 | Oligo48 | L3 | L3-1 | 99 |
| 106.3 | Oligo49 | L3 | L3-2 | 99 |
| 106.3 | Oligo50 | L3 | L3-3 | 99 |
| 106.3 | Oligo51 | L3 | L3-4 | 99 |
| 106.3 | Oligo52 | L3 | L3-5 | 99 |
| 106.3 | Oligo53 | L3 | L3-6 | 93 |
| 106.3 | Oligo54 | L3 | L3-7 | 93 |

Oligo48
   CAT CCT GTG GAG GAG GAG GAT GCT GCA ACC TAT TAC TGT **NNS NNS NNS
   AAT GAG GAT CCA TTC ACG** TTC GGC TCG GGG ACA AAG TTG GAA ATA
   AAA CGG Oligo49
   CAT CCT GTG GAG GAG GAG GAT GCT GCA ACC TAT TAC TGT **CAG NNS
   NNS NNS GAG GAT CCA TTC ACG** TTC GGC TCG GGG ACA AAG TTG GAA
   ATA AAA CGG Oligo50
   CAT CCT GTG GAG GAG GAG GAT GCT GCA ACC TAT TAC TGT **CAG CAA
   NNS NNS NNS GAT CCA TTC ACG** TTC GGC TCG GGG ACA AAG TTG GAA
   ATA AAA CGG Oligo51
   CAT CCT GTG GAG GAG GAG GAT GCT GCA ACC TAT TAC TGT **CAG CAA
   AGT NNS NNS NNS CCA TTC ACG** TTC GGC TCG GGG ACA AAG TTG GAA
   ATA AAA CGG Oligo52
   CAT CCT GTG GAG GAG GAG GAT GCT GCA ACC TAT TAC TGT **CAG CAA
   AGT AAT NNS NNS NNS TTC ACG** TTC GGC TCG GGG ACA AAG TTG GAA
   ATA AAA CGG

FIGURE 14H

Oligo53
    GAG GAT GCT GCA ACC TAT TAC TGT CAG CAA AGT AAT GAG NNS NNS NNS ACG TTC GGC TCG GGG ACA AAG TTG GAA ATA AAA CGG GCG GCC GCC Oligo54
    GAG GAT GCT GCA ACC TAT TAC TGT CAG CAA AGT AAT GAG GAT NNS NNS NNS TTC GGC TCG GGG ACA AAG TTG GAA ATA AAA CGG GCG GCC GCC

SEQUENCE LISTING

<160> NUMBER OF SEQ ID NOS: 82

<210> SEQ ID NO 1
<211> LENGTH: 5745
<212> TYPE: DNA
<213> ORGANISM: Artificial Sequence
<220> FEATURE:
<223> OTHER INFORMATION: Immunoglobulin variable heavy and variable
      light chain

<400> SEQUENCE: 1

```
acggattaga agccgccgag cgggtgacag ccctccgaag gaagactctc ctccgtgcgt      60
cctcgtcctc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcatt aaccacttta actaatactt tcaacatttt     360
cggtttgtat tacttcttat tcaaatgtaa taaaagtatc aacaaaaaat tgttaatata     420
cctctatact ttaacgtcaa ggagaaaaaa ccccggatcg gactactagc agctgtaata     480
cgactcacta tagggaatat taagctaatt ctacttcata cattttcaat taagatgcag     540
ttacttcgct gttttcaat attttctgtt attgcttcag ttttagcaca ggaactgaca     600
actatatgcg agcaaatccc ctcaccaact ttagaatcga cgccgtactc tttgtcaacg     660
actactattt tggccaacgg gaaggcaatg caaggagttt ttgaatatta caaatcagta     720
acgtttgtca gtaattgcgg ttctcacccc tcaacaacta gcaaaggcag ccccataaac     780
acacagtatg ttttaagct tctgcaggct agtggtgaga caaggtgga gtacgcgccg     840 gcgttgatgg ccttgtctgc tagcatgact ggtggacagc aaatgggtcg gatctgtac     900 gacgatgacg ataaggtacc aggatccagt gtggtggaat tcgcggccca gccggccatg     960
gcccagatcc agttggtgca gtctggacct gagctgagga agcctggaga gacagtcaag    1020
atctcctgca agggttctgg atataccttc acacactatg gaataaactg ggtgaagcag    1080
actccaagaa aggatttaaa gtggatgggc tggataaaca cccatactgg agagccaata    1140
tatgctgatg acttcaaggg acggtttgcc ttctcttttgg aaacctctgc caacactgcc    1200
tatttgcaaa tcaacaacct caacaatgga gacatgggta catatttctg tacaagaagt    1260
caccggtttg gtttggacta ctggggtcaa ggtacctcag tcaccgtctc gtcaggtccc    1320
gccaaggagt tgacgcccct gaaggaggcg aaggtctctg acaatgtgct gacccaatct    1380
ccaccttctt tggctgtgtc tctagggcag agggccacca tctcctgcaa ggccagccaa    1440
agtgttgatt ataatggtga tagttatctg aactggtacc aacagaagcc aggacagcca    1500
cccaaattcc tcatctatgc tgcatccaat ctagaatctg ggatcccagc caggtttagt    1560
ggcagtgggt ctgggacaga cttcaacctc aacatccatc ctgtggagga ggaggatgct    1620
gcaacctatt actgtcagca aagtaatgag gatccattca cgttcggctc ggggacaaag    1680
ttggaaataa aacgggcggc cgccctcgag tctagagggc ccttcgaagg taagcctatc    1740
cctaaccctc tcctcggtct cgattctacg cgtaccggtc atcatcacca tcaccattga    1800
gtttaaaccc gctgatctga taacaacagt gtagatgtaa caaaatcgac tttgttccca    1860
ctgtactttt agctcgtaca aaatacaata tacttttcat ttctccgtaa caacatgtt    1920 ttcccatgta atatcctttt ctattttcg ttccgttacc aactttacac atactttata    1980
```

```
tagctattca cttctataca ctaaaaaact aagacaattt taattttgct gcctgccata   2040
tttcaatttg ttataaattc ctataattta tcctattagt agctaaaaaa agatgaatgt   2100
gaatcgaatc ctaagagaat tgggcaagtg cacaaacaat acttaaataa atactactca   2160 gtaataaccct atttcttagc attttttgacg aaatttgcta ttttgttaga gtcttttaca  2220
ccatttgtct ccacacctcc gcttacatca acaccaataa cgccatttaa tctaagcgca   2280
tcaccaacat tttctggcgt cagtccacca gctaacataa aatgtaagct ctcggggctc   2340
tcttgccttc caacccagtc agaaatcgag ttccaatcca aaagttcacc tgtcccacct   2400
gcttctgaat caaacaaggg aataaacgaa tgaggtttct gtgaagctgc actgagtagt   2460
atgttgcagt cttttggaaa tacgagtctt ttaataactg gcaaaccgag gaactcttgg   2520
tattcttgcc acgactcatc tccgtgcagt tggacgatat caatgccgta atcattgacc   2580
agagccaaaa catcctcctt aggttgatta cgaaacacgc caaccaagta tttcggagtg   2640
cctgaactat ttttatatgc ttttacaaga cttgaaattt tccttgcaat aaccgggtca   2700
attgttctct ttctattggg cacacatata atacccagca agtcagcatc ggaatctaga   2760
gcacattctg cggcctctgt gctctgcaag ccgcaaaactt tcaccaatgg accagaacta   2820
cctgtgaaat aataacaga catactccaa gctgcctttg tgtgcttaat cacgtatact   2880
cacgtgctca atagtcacca atgccctccc tcttggccct ctcctttttct tttttcgacc   2940 gaatttcttg aagacgaaag ggcctcgtga tacgcctatt tttataggtt aatgtcatga   3000
taataatggt tcttaggac ggatcgcttg cctgtaactt acacgcgcct cgtatctttt   3060
aatgatggaa taatttggga atttactctg tgtttatttta tttttatgtt ttgtatttgg   3120
attttagaaa gtaaataaag aaggtagaag agttacggaa tgaagaaaaa aaaataaaca   3180
aaggtttaaa aaatttcaac aaaaagcgta ctttacatat atatttatta gacaagaaaa   3240
gcagattaaa tagatataca ttcgattaac gataagtaaa atgtaaaatc acaggatttt   3300
cgtgtgtggt cttctacaca gacaagatga aacaattcgg cattaatacc tgagagcagg   3360
aagagcaaga taaaggtag tatttgttgg cgatcccct agagtctttt acatcttcgg   3420
aaaacaaaaa ctattttttc tttaatttct ttttttactt tctattttta atttatatat   3480
ttatattaaa aaatttaaat tataattatt tttatagcac gtgatgaaaa ggacccaggt   3540 ggcactttc ggggaaatgt gcgcggaacc cctatttgtt tattttttcta aatacattca   3600 aatatgtatc cgctcatgag acaataaccc tgataaatgc ttcaataata ttgaaaaagg   3660
aagagtatga gtattcaaca tttccgtgtc gcccttattc ccttttttgc ggcattttgc   3720
cttcctgttt ttgctcaccc agaaacgctg gtgaaagtaa aagatgctga agatcagttg   3780
ggtgcacgag tgggttacat cgaactggat ctcaacagcg gtaagatcct tgagagtttt   3840
cgccccgaag aacgttttcc aatgatgagc acttttaaag ttctgctatg tggcgcggta   3900
ttatcccgtg ttgacgccgg gcaagagcaa ctcggtcgcc gcatacacta ttctcagaat   3960
gacttggttg agtactcacc agtcacagaa aagcatctta cggatggcat gacagtaaga   4020
gaattatgca gtgctgccat aaccatgagt gataacactg cggccaactt acttctgaca   4080
acgatcggag gaccgaagga gctaaccgct ttttttgcaca acatggggga tcatgtaact   4140
cgccttgatc gttgggaacc ggagctgaat gaagccatac caaacgacga gcgtgacacc   4200
acgatgcctg tagcaatggc aacaacgttg cgcaaactat taactggcga actacttact   4260
ctagcttccc ggcaacaatt aatagactgg atggaggcgg ataaagttgc aggaccactt   4320
ctgcgctcgg cccttccggc tggctggttt attgctgata aatctggagc cggtgagcgt   4380
```

```
gggtctcgcg gtatcattgc agcactgggg ccagatggta agccctcccg tatcgtagtt    4440
atctacacga cgggcagtca ggcaactatg gatgaacgaa atagacagat cgctgagata    4500
ggtgcctcac tgattaagca ttggtaactg tcagaccaag tttactcata tatactttag    4560
attgatttaa aacttcattt ttaatttaaa aggatctagg tgaagatcct ttttgataat    4620
ctcatgacca aaatccctta acgtgagttt tcgttccact gagcgtcaga ccccgtagaa    4680
aagatcaaag gatcttcttg agatcctttt tttctgcgcg taatctgctg cttgcaaaca    4740
aaaaaaccac cgctaccagc ggtggtttgt ttgccggatc aagagctacc aactctttt    4800 ccgaaggtaa ctggcttcag cagagcgcag ataccaaata ctgtccttct agtgtagccg    4860
tagttaggcc accacttcaa gaactctgta gcaccgccta catacctcgc tctgctaatc    4920
ctgttaccag tggctgctgc cagtggcgat aagtcgtgtc ttaccgggtt ggactcaaga    4980
cgatagttac cggataaggc gcagcggtcg ggctgaacgg ggggttcgtg cacacagccc    5040
agcttggagc gaacgaccta caccgaactg agatacctac agcgtgagca ttgagaaagc    5100
gccacgcttc ccgaagggag aaaggcggac aggtatccgg taagcggcag gtcggaaca    5160 ggagagcgca cgagggagct tccagggggg aacgcctggt atctttatag tcctgtcggg    5220
tttcgccacc tctgacttga gcgtcgattt ttgtgatgct cgtcaggggg gcggagccta    5280
tggaaaaacg ccagcaacgc ggccttttta cggttcctgg ccttttgctg gccttttgct    5340
cacatgttct ttcctgcgtt atcccctgat tctgtggata accgtattac cgcctttgag    5400
tgagctgata ccgctcgccg cagccgaacg accgagcgca gcgagtcagt gagcgaggaa    5460
gcggaagagc gcccaatacg caaaccgcct ctccccgcgc gttggccgat tcattaatgc    5520
agctggcacg acaggtttcc cgactggaaa gcgggcagtg agcgcaacgc aattaatgtg    5580
agttacctca ctcattaggc accccaggct ttacacttta tgcttccggc tcctatgttg    5640
tgtggaattg tgagcggata acaatttcac acaggaaaca gctatgacca tgattacgcc    5700
aagctcggaa ttaaccctca ctaaagggaa caaaagctgg ctagt              5745
```

<210> SEQ ID NO 2
<211> LENGTH: 837
<212> TYPE: DNA
<213> ORGANISM: Artificial Sequence
<220> FEATURE:
<223> OTHER INFORMATION: 106.3 scFv

<400> SEQUENCE: 2

```
gtctaggtca accacgtcag acctggactc gactccttcg gacctctctg tcagttctag     60
aggacgttcc caagacctat atggaagtgt gtgataccct atttgaccca cttcgtctga    120
ggttctttcc taaatttcac ctacccgacc tatttgtggg tatgacctct cggttatata    180
cgactactga agttccctgc caaacggaag agaaaccttt ggagacggtt gtgacggata    240
aacgtttagt tgttggagtt gttacctctg tacccatgta taaagacatg ttcttcagtg    300
gccaaaccaa acctgatgac cccagttcca tggagtcagt ggcagagcag tccagggcgg    360
ttcctcaact gcggggactt cctccgcttc cagagactgt tacacgactg ggttagaggt    420
ggaagaaacc gacacagaga tcccgtctcc cggtggtaga ggacgttccg gtcggtttca    480
caactaatat taccactatc aatagacttg accatggttc tcttcggtcc tgtcggtggg    540
tttaaggagt agatacgacg taggttagat cttagaccct agggtcggtc caaatcaccg    600
tcacccagac cctgtctgaa gttggagttg taggtaggac acctcctcct cctacgacgt    660
tggataatga cagtcgtttc attactccta ggtaagtgca agccgagccc ctgtttcaac    720
```

```
ctttattttg cccgccggcg ggagctcaga tctcccggga agcttccatt cggatagga    780 ttgggagagg agccagagct aagatgcgca tggccagtag tagtggtagt ggtaact      837
```

<210> SEQ ID NO 3
<211> LENGTH: 276
<212> TYPE: PRT
<213> ORGANISM: Artificial Sequence
<220> FEATURE:
<223> OTHER INFORMATION: 106.3 scFV

<400> SEQUENCE: 3

```
Gln Leu Val Gln Ser Gly Pro Glu Leu Arg Lys Pro Gly Glu Thr Val
 1               5                  10                  15

Lys Ile Ser Cys Lys Gly Ser Gly Tyr Thr Phe Thr His Tyr Gly Ile
            20                  25                  30

Asn Trp Val Lys Gln Thr Pro Arg Lys Asp Leu Lys Trp Met Gly Trp
        35                  40                  45

Ile Asn Thr His Thr Gly Glu Pro Ile Tyr Ala Asp Asp Phe Lys Gly
    50                  55                  60

Arg Phe Ala Phe Ser Leu Glu Thr Ser Ala Asn Thr Ala Tyr Leu Gln
65                  70                  75                  80

Ile Asn Asn Leu Asn Asn Gly Asp Met Gly Thr Tyr Phe Cys Thr Arg
                85                  90                  95

Ser His Arg Phe Gly Leu Asp Tyr Trp Gly Gln Gly Thr Ser Val Thr
            100                 105                 110

Val Ser Ser Gly Pro Ala Lys Glu Leu Thr Pro Leu Lys Glu Ala Lys
        115                 120                 125

Val Ser Asp Asn Val Leu Thr Gln Ser Pro Pro Ser Leu Ala Val Ser
    130                 135                 140

Leu Gly Gln Arg Ala Thr Ile Ser Cys Lys Ala Ser Gln Ser Val Asp
145                 150                 155                 160

Tyr Asn Gly Asp Ser Tyr Leu Asn Trp Tyr Gln Gln Lys Pro Gly Gln
                165                 170                 175

Pro Pro Lys Phe Leu Ile Tyr Ala Ala Ser Asn Leu Glu Ser Gly Ile
            180                 185                 190

Pro Ala Arg Phe Ser Gly Ser Gly Ser Gly Thr Asp Phe Asn Leu Asn
        195                 200                 205

Ile His Pro Val Glu Glu Asp Ala Ala Thr Tyr Tyr Cys Gln Gln
    210                 215                 220

Ser Asn Glu Asp Pro Phe Thr Phe Gly Ser Gly Thr Lys Leu Glu Ile
225                 230                 235                 240

Lys Arg Ala Ala Ala Leu Glu Ser Arg Gly Pro Phe Glu Gly Lys Pro
                245                 250                 255

Ile Pro Asn Pro Leu Leu Gly Leu Asp Ser Thr Arg Thr Gly His His
            260                 265                 270

His His His His
        275
```

<210> SEQ ID NO 4
<211> LENGTH: 15
<212> TYPE: PRT
<213> ORGANISM: Artificial Sequence
<220> FEATURE:
<223> OTHER INFORMATION: Flexible linker

<400> SEQUENCE: 4

```
Gly Pro Ala Lys Glu Leu Thr Pro Leu Lys Glu Ala Lys Val Ser
```

<210> SEQ ID NO 5
<211> LENGTH: 32
<212> TYPE: PRT
<213> ORGANISM: Homo sapiens

<400> SEQUENCE: 5

Ser Pro Lys Met Val Gln Gly Ser Gly Cys Phe Gly Arg Lys Met Asp
1               5                   10                  15

Arg Ile Ser Ser Ser Gly Leu Gly Cys Lys Val Leu Arg Arg His
            20                  25                  30

<210> SEQ ID NO 6
<211> LENGTH: 10
<212> TYPE: PRT
<213> ORGANISM: Artificial Sequence
<220> FEATURE:
<223> OTHER INFORMATION: Heavy Chain CDR

<400> SEQUENCE: 6

Gly Tyr Thr Phe Thr His Tyr Gly Ile Asn
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Heavy chain CDR 2

<400> SEQUENCE: 7

Trp Ile Asn Thr His Thr Gly Glu Pro Ile Tyr Ala Asp Asp Phe Lys
1               5                   10                  15

Gly

<210> SEQ ID NO 8
<211> LENGTH: 8
<212> TYPE: PRT
<213> ORGANISM: Artificial Sequence
<220> FEATURE:
<223> OTHER INFORMATION: Heavy Chain CDR 3

<400> SEQUENCE: 8

Ser His Arg Phe Gly Leu Asp Tyr
1               5

<210> SEQ ID NO 9
<211> LENGTH: 15
<212> TYPE: PRT
<213> ORGANISM: Artificial Sequence
<220> FEATURE:
<223> OTHER INFORMATION: Light chain CDR 1

<400> SEQUENCE: 9

Lys Ala Ser Gln Ser Val Asp Tyr Asn Gly Asp Ser Tyr Leu Asn
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: Light chain CDR 2

<400> SEQUENCE: 10

```
Ala Ala Ser Asn Leu Glu Ser
  1               5

<210> SEQ ID NO 11
<211> LENGTH: 9
<212> TYPE: PRT
<213> ORGANISM: Artificial Sequence
<220> FEATURE:
<223> OTHER INFORMATION: Light Chain CDR 3

<400> SEQUENCE: 11

Gln Gln Ser Asn Glu Asp Pro Phe Thr
  1               5

<210> SEQ ID NO 12
<211> LENGTH: 17
<212> TYPE: PRT
<213> ORGANISM: Artificial Sequence
<220> FEATURE:
<221> NAME/KEY: VARIANT
<222> LOCATION: (9)...(10)
<223> OTHER INFORMATION: Xaa1 = Pro, Ala and Xaa2 = Ile or Tyr; Heavy
      chain CDR 2

<400> SEQUENCE: 12

Trp Ile Asn Thr His Thr Gly Glu Xaa Xaa Tyr Ala Asp Asp Phe Lys
  1               5                  10                  15

Gly

<210> SEQ ID NO 13
<211> LENGTH: 15
<212> TYPE: PRT
<213> ORGANISM: Artificial Sequence
<220> FEATURE:
<221> NAME/KEY: VARIANT
<222> LOCATION: (3)...(5)
<223> OTHER INFORMATION: Xaa3 = Ser, Ala, Asn, Gln, Tyr, Thr or Arg;
      Xaa4 = Gln, Tyr, Trp, Ala or Phe; Xaa5 = Ser, Gly, Pro,
      Ala or Asp; light chain CDR 1

<400> SEQUENCE: 13

Lys Ala Xaa Xaa Xaa Val Asp Tyr Asn Gly Asp Ser Tyr Leu Asn
  1               5                  10                  15

<210> SEQ ID NO 14
<211> LENGTH: 7
<212> TYPE: PRT
<213> ORGANISM: Artificial Sequence
<220> FEATURE:
<221> NAME/KEY: VARIANT
<222> LOCATION: (4)...(6)
<223> OTHER INFORMATION: Xaa6 = Asp or Cys; Xaa7 = Leu, Gly or Ala;
      Xaa8 = Glu, Trp or Pro; light chain CDR 2

<400> SEQUENCE: 14

Ala Ala Ser Xaa Xaa Xaa Ser
  1               5

<210> SEQ ID NO 15
<211> LENGTH: 17
<212> TYPE: PRT
<213> ORGANISM: Artificial Sequence
<220> FEATURE:
<223> OTHER INFORMATION: CDR H2 Mutation 57 P with A and Mutation 58 I
      with Y

<400> SEQUENCE: 15

Trp Ile Asn Thr His Thr Gly Glu Ala Tyr Tyr Ala Asp Asp Phe Lys
  1               5                  10                  15
```

Gly

<210> SEQ ID NO 16
<211> LENGTH: 15
<212> TYPE: PRT
<213> ORGANISM: Artificial Sequence
<220> FEATURE:
<223> OTHER INFORMATION: CDR L1 Mutation 26 S with Q and Mutation 27 Q
      with F and 27A with Ser to A

<400> SEQUENCE: 16

Lys Ala Gln Phe Ala Val Asp Tyr Asn Gly Asp Ser Tyr Leu Asn
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: CDR L1 Mutation 26 S with Y and Mutation 27 Q
      with A

<400> SEQUENCE: 17

Lys Ala Tyr Ala Ser Val Asp Tyr Asn Gly Asp Ser Tyr Leu Asn
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: CDR L1 Mutation 26 S with Q and Mutation 27 Q
      with W and 27A with Ser to G

<400> SEQUENCE: 18

Lys Ala Gln Trp Gly Val Asp Tyr Asn Gly Asp Ser Tyr Leu Asn
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Mutation 26 S with T and Mutation 27 Q with W
      and 27A with Ser to D

<400> SEQUENCE: 19

Lys Ala Thr Trp Asp Val Asp Tyr Asn Gly Asp Ser Tyr Leu Asn
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: CDR L1 Mutation 26 S with R and Mutation 27 Q
      with W and 27A with Ser to P

<400> SEQUENCE: 20

Lys Ala Arg Trp Pro Val Asp Tyr Asn Gly Asp Ser Tyr Leu Asn
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: CDR L1 Mutation 26 S with A and Mutation 27 Q with Y and 27A with Ser to G

<400> SEQUENCE: 21

Lys Ala Ala Tyr Gly Val Asp Tyr Asn Gly Asp Ser Tyr Leu Asn
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: CDR L1 Mutation 26 S with N and Mutation 27 Q
      with W and 27A with Ser to P

<400> SEQUENCE: 22

Lys Ala Asn Trp Pro Val Asp Tyr Asn Gly Asp Ser Tyr Leu Asn
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: CDR L2 Mutation 53 N with C, Mutation 54 L with
      G and Mutation 55 E with W

<400> SEQUENCE: 23

Ala Ala Ser Cys Gly Trp Ser
1               5

<210> SEQ ID NO 24
<211> LENGTH: 7
<212> TYPE: PRT
<213> ORGANISM: Artificial Sequence
<220> FEATURE:
<223> OTHER INFORMATION: CDR L2 Mutation 53 N with C, Mutation 54 L with
      A and Mutation 55 E with P

<400> SEQUENCE: 24

Ala Ala Ser Cys Ala Pro Ser
1               5

<210> SEQ ID NO 25
<211> LENGTH: 105
<212> TYPE: DNA
<213> ORGANISM: Artificial Sequence
<220> FEATURE:
<221> NAME/KEY: variation
<222> LOCATION: (43)...(51)
<223> OTHER INFORMATION: N= A, G, C, T; S = G, C ; Degenerate
      Oligonucleotides

<400> SEQUENCE: 25
aacctcaaca atggagacat gggtacatat ttctgtacaa gannsnnsnn stttggtttg      60
gactactggg gtcaaggtac ctcagtcacc gtctcgtcag gtccc                    105

<210> SEQ ID NO 26
<211> LENGTH: 105
<212> TYPE: DNA
<213> ORGANISM: Artificial Sequence
<220> FEATURE:
<221> NAME/KEY: variation
<222> LOCATION: (46)...(54)
<223> OTHER INFORMATION: N= A, G, C, T; S = G, C; Degenerate
      Oligonucleotides

<400> SEQUENCE: 26
aacctcaaca atggagacat gggtacatat ttctgtacaa gaagtnnsnn snnsggtttg      60

```
gactactggg gtcaaggtac ctcagtcacc gtctcgtcag gtccc              105

<210> SEQ ID NO 27
<211> LENGTH: 105
<212> TYPE: DNA
<213> ORGANISM: Artificial Sequence
<220> FEATURE:
<221> NAME/KEY: variation
<222> LOCATION: (49)...(57)
<223> OTHER INFORMATION: N= A, G, C, T; S = G, C; Degenerate
      Oligonucleotides

<400> SEQUENCE: 27
aacctcaaca atggagacat gggtacatat ttctgtacaa gaagtcacnn snnsnnsttg    60
gactactggg gtcaaggtac ctcagtcacc gtctcgtcag gtccc                  105

<210> SEQ ID NO 28
<211> LENGTH: 105
<212> TYPE: DNA
<213> ORGANISM: Artificial Sequence
<220> FEATURE:
<221> NAME/KEY: variation
<222> LOCATION: (52)...(60)
<223> OTHER INFORMATION: N= A, G, C, T; S = G, C; Degenerate
      Oligonucleotides

<400> SEQUENCE: 28
aacctcaaca atggagacat gggtacatat ttctgtacaa gaagtcaccg gnnsnnsnns    60
gactactggg gtcaaggtac ctcagtcacc gtctcgtcag gtccc                  105

<210> SEQ ID NO 29
<211> LENGTH: 105
<212> TYPE: DNA
<213> ORGANISM: Artificial Sequence
<220> FEATURE:
<221> NAME/KEY: variation
<222> LOCATION: (55)...(63)
<223> OTHER INFORMATION: N= A, G, C, T; S = G, C; Degenerate
      Oligonucleotides

<400> SEQUENCE: 29
aacctcaaca atggagacat gggtacatat ttctgtacaa gaagtcaccg gtttnnsnns    60
nnstactggg gtcaaggtac ctcagtcacc gtctcgtcag gtccc                  105

<210> SEQ ID NO 30
<211> LENGTH: 99
<212> TYPE: DNA
<213> ORGANISM: Artificial Sequence
<220> FEATURE:
<221> NAME/KEY: variation
<222> LOCATION: (43)...(51)
<223> OTHER INFORMATION: N= A, G, C, T; S = G, C; Degenerate
      Oligonucleotides

<400> SEQUENCE: 30
gacatgggta catatttctg tacaagaagt caccggtttg gtnnsnnsnn stggggtcaa    60
ggtacctcag tcaccgtctc gtcaggtccc gccgccaag                         99

<210> SEQ ID NO 31
<211> LENGTH: 105
<212> TYPE: DNA
<213> ORGANISM: Artificial Sequence
<220> FEATURE:
<221> NAME/KEY: variation
<222> LOCATION: (43)...(51)
<223> OTHER INFORMATION: N= A, G, C, T; S = G, C; Degenerate
```

-continued

Oligonucleotides

<400> SEQUENCE: 31
tgggtgaagc agactccaag aaaggattta aagtggatgg gcnnsnnsnn sacccatact    60
ggagagccaa tatatgctga tgacttcaag ggacggtttg ccttc    105

<210> SEQ ID NO 32
<211> LENGTH: 105
<212> TYPE: DNA
<213> ORGANISM: Artificial Sequence
<220> FEATURE:
<221> NAME/KEY: variation
<222> LOCATION: (46)...(54)
<223> OTHER INFORMATION: N= A, G, C, T; S = G, C; Degenerate
      Oligonucleotides

<400> SEQUENCE: 32
tgggtgaagc agactccaag aaaggattta aagtggatgg gctggnnsnn snnscatact    60
ggagagccaa tatatgctga tgacttcaag ggacggtttg ccttc    105

<210> SEQ ID NO 33
<211> LENGTH: 105
<212> TYPE: DNA
<213> ORGANISM: Artificial Sequence
<220> FEATURE:
<221> NAME/KEY: variation
<222> LOCATION: (49)...(57)
<223> OTHER INFORMATION: N= A, G, C, T; S = G, C; Degenerate
      Oligonucleotides

<400> SEQUENCE: 33
tgggtgaagc agactccaag aaaggattta aagtggatgg gctggatann snnsnnsact    60
ggagagccaa tatatgctga tgacttcaag ggacggtttg ccttc    105

<210> SEQ ID NO 34
<211> LENGTH: 105
<212> TYPE: DNA
<213> ORGANISM: Artificial Sequence
<220> FEATURE:
<221> NAME/KEY: variation
<222> LOCATION: (52)...(60)
<223> OTHER INFORMATION: N = A, G, C, T; S = G, C; Degenerate
      Oligonucleotides

<400> SEQUENCE: 34
tgggtgaagc agactccaag aaaggattta aagtggatgg gctggataaa cnnsnnsnns    60
ggagagccaa tatatgctga tgacttcaag ggacggtttg ccttc    105

<210> SEQ ID NO 35
<211> LENGTH: 105
<212> TYPE: DNA
<213> ORGANISM: Artificial Sequence
<220> FEATURE:
<221> NAME/KEY: variation
<222> LOCATION: (55)...(63)
<223> OTHER INFORMATION: N = A, G, C, T; S = G, C; Degenerate
      Oligonucleotides

<400> SEQUENCE: 35
tgggtgaagc agactccaag aaaggattta aagtggatgg gctggataaa caccnnsnns    60
nnsgagccaa tatatgctga tgacttcaag ggacggtttg ccttc    105

<210> SEQ ID NO 36
<211> LENGTH: 105
<212> TYPE: DNA

```
<213> ORGANISM: Artificial Sequence
<220> FEATURE:
<221> NAME/KEY: variation
<222> LOCATION: (43)...(51)
<223> OTHER INFORMATION: N = A, G, C, T; S = G, C; Degenerate
      Oligonucleotides

<400> SEQUENCE: 36
ccaagaaagg atttaaagtg gatgggctgg ataaacaccc atnnsnnsnn sccaatatat    60
gctgatgact tcaagggacg gtttgccttc tctttggaaa cctct                   105

<210> SEQ ID NO 37
<211> LENGTH: 105
<212> TYPE: DNA
<213> ORGANISM: Artificial Sequence
<220> FEATURE:
<221> NAME/KEY: variation
<222> LOCATION: (46)...(54)
<223> OTHER INFORMATION: N = A, G, C, T; S = G, C; Degenerate
      Oligonucleotides

<400> SEQUENCE: 37
ccaagaaagg atttaaagtg gatgggctgg ataaacaccc atactnnsnn snnsatatat    60
gctgatgact tcaagggacg gtttgccttc tctttggaaa cctct                   105

<210> SEQ ID NO 38
<211> LENGTH: 105
<212> TYPE: DNA
<213> ORGANISM: Artificial Sequence
<220> FEATURE:
<221> NAME/KEY: variation
<222> LOCATION: (49)...(57)
<223> OTHER INFORMATION: N = A, G, C, T; S = G, C; Degenerate
      Oligonucleotides

<400> SEQUENCE: 38
ccaagaaagg atttaaagtg gatgggctgg ataaacaccc atactggann snnsnnstat    60
gctgatgact tcaagggacg gtttgccttc tctttggaaa cctct                   105

<210> SEQ ID NO 39
<211> LENGTH: 105
<212> TYPE: DNA
<213> ORGANISM: Artificial Sequence
<220> FEATURE:
<221> NAME/KEY: variation
<222> LOCATION: (52)...(60)
<223> OTHER INFORMATION: N = A, G, C, T; S = G, C; Degenerate
      Oligonucleotides

<400> SEQUENCE: 39
ccaagaaagg atttaaagtg gatgggctgg ataaacaccc atactggaga gnnsnnsnns    60
gctgatgact tcaagggacg gtttgccttc tctttggaaa cctct                   105

<210> SEQ ID NO 40
<211> LENGTH: 105
<212> TYPE: DNA
<213> ORGANISM: Artificial Sequence
<220> FEATURE:
<221> NAME/KEY: variation
<222> LOCATION: (55)...(63)
<223> OTHER INFORMATION: N = A, G, C, T; S = G, C; Degenerate
      Oligonucleotides

<400> SEQUENCE: 40
ccaagaaagg atttaaagtg gatgggctgg ataaacaccc atactggaga gccannsnns    60
nnsgatgact tcaagggacg gtttgccttc tctttggaaa cctct                   105
```

<210> SEQ ID NO 41
<211> LENGTH: 105
<212> TYPE: DNA
<213> ORGANISM: Artificial Sequence
<220> FEATURE:
<221> NAME/KEY: variation
<222> LOCATION: (43)...(51)
<223> OTHER INFORMATION: N = A, G, C, T; S = G, C; Degenerate
      Oligonucleotides

<400> SEQUENCE: 41
aagtggatgg gctggataaa cacccatact ggagagccaa tannsnnsnn sgacttcaag    60
ggacggtttg ccttctcttt ggaaacctct gccaacactg cctat                  105

<210> SEQ ID NO 42
<211> LENGTH: 105
<212> TYPE: DNA
<213> ORGANISM: Artificial Sequence
<220> FEATURE:
<221> NAME/KEY: variation
<222> LOCATION: (46)...(54)
<223> OTHER INFORMATION: N = A, G, C, T; S = G, C; Degenerate
      Oligonucleotides

<400> SEQUENCE: 42
aagtggatgg gctggataaa cacccatact ggagagccaa tatatnnsnn snnsttcaag    60
ggacggtttg ccttctcttt ggaaacctct gccaacactg cctat                  105

<210> SEQ ID NO 43
<211> LENGTH: 105
<212> TYPE: DNA
<213> ORGANISM: Artificial Sequence
<220> FEATURE:
<221> NAME/KEY: variation
<222> LOCATION: (49)...(57)
<223> OTHER INFORMATION: N = A, G, C, T; S = G, C; Degenerate
      Oligonucleotides

<400> SEQUENCE: 43
aagtggatgg gctggataaa cacccatact ggagagccaa tatatgctnn snnsnnsaag    60
ggacggtttg ccttctcttt ggaaacctct gccaacactg cctat                  105

<210> SEQ ID NO 44
<211> LENGTH: 105
<212> TYPE: DNA
<213> ORGANISM: Artificial Sequence
<220> FEATURE:
<221> NAME/KEY: variation
<222> LOCATION: (52)...(60)
<223> OTHER INFORMATION: N = A, G, C, T; S = G, C; Degenerate
      Oligonucleotides

<400> SEQUENCE: 44
aagtggatgg gctggataaa cacccatact ggagagccaa tatatgctga tnnsnnsnns    60
ggacggtttg ccttctcttt ggaaacctct gccaacactg cctat                  105

<210> SEQ ID NO 45
<211> LENGTH: 105
<212> TYPE: DNA
<213> ORGANISM: Artificial Sequence
<220> FEATURE:
<221> NAME/KEY: variation
<222> LOCATION: (55)...(63)
<223> OTHER INFORMATION: N = A, G, C, T; S = G, C; Degenerate
      Oligonucleotides

<400> SEQUENCE: 45
aagtggatgg gctggataaa cacccatact ggagagccaa tatatgctga tgacnnsnns    60
nnscggtttg ccttctcttt ggaaacctct gccaacactg cctat    105

<210> SEQ ID NO 46
<211> LENGTH: 105
<212> TYPE: DNA
<213> ORGANISM: Artificial Sequence
<220> FEATURE:
<221> NAME/KEY: variation
<222> LOCATION: (43)...(51)
<223> OTHER INFORMATION: N = A, G, C, T; S = G, C; Degenerate
      Oligonucleotides

<400> SEQUENCE: 46
aggaagcctg gagagacagt caagatctcc tgcaagggtt ctnnsnnsnn sttcacacac    60
tatggaataa actgggtgaa gcagactcca agaaaggatt taaag    105

<210> SEQ ID NO 47
<211> LENGTH: 105
<212> TYPE: DNA
<213> ORGANISM: Artificial Sequence
<220> FEATURE:
<221> NAME/KEY: variation
<222> LOCATION: (46)...(54)
<223> OTHER INFORMATION: N = A, G, C, T; S = G, C; Degenerate
      Oligonucleotides

<400> SEQUENCE: 47
aggaagcctg gagagacagt caagatctcc tgcaagggtt ctggannsnn snnsacacac    60
tatggaataa actgggtgaa gcagactcca agaaaggatt taaag    105

<210> SEQ ID NO 48
<211> LENGTH: 105
<212> TYPE: DNA
<213> ORGANISM: Artificial Sequence
<220> FEATURE:
<221> NAME/KEY: variation
<222> LOCATION: (49)...(57)
<223> OTHER INFORMATION: N = A, G, C, T; S = G, C; Degenerate
      Oligonucleotides

<400> SEQUENCE: 48
aggaagcctg gagagacagt caagatctcc tgcaagggtt ctggatatnn snnsnnscac    60
tatggaataa actgggtgaa gcagactcca agaaaggatt taaag    105

<210> SEQ ID NO 49
<211> LENGTH: 105
<212> TYPE: DNA
<213> ORGANISM: Artificial Sequence
<220> FEATURE:
<221> NAME/KEY: variation
<222> LOCATION: (52)...(60)
<223> OTHER INFORMATION: N = A, G, C, T; S = G, C; Degenerate
      Oligonucleotides

<400> SEQUENCE: 49
aggaagcctg gagagacagt caagatctcc tgcaagggtt ctggatatac cnnsnnsnns    60
tatggaataa actgggtgaa gcagactcca agaaaggatt taaag    105

<210> SEQ ID NO 50
<211> LENGTH: 105
<212> TYPE: DNA
<213> ORGANISM: Artificial Sequence
<220> FEATURE:

```
<221> NAME/KEY: variation
<222> LOCATION: (55)...(63)
<223> OTHER INFORMATION: N = A, G, C, T; S = G, C; Degenerate
      Oligonucleotides

<400> SEQUENCE: 50
aggaagcctg gagagacagt caagatctcc tgcaagggtt ctggatatac cttcnnsnns    60
nnsggaataa actgggtgaa gcagactcca agaaaggatt taaag                  105

<210> SEQ ID NO 51
<211> LENGTH: 99
<212> TYPE: DNA
<213> ORGANISM: Artificial Sequence
<220> FEATURE:
<221> NAME/KEY: variation
<222> LOCATION: (43)...(51)
<223> OTHER INFORMATION: N = A, G, C, T; S = G, C; Degenerate
      Oligonucleotides

<400> SEQUENCE: 51
acagtcaaga tctcctgcaa gggttctgga tataccttca cannsnnsnn sataaactgg   60
gtgaagcaga ctccaagaaa ggatttaaag tggatgggc                          99

<210> SEQ ID NO 52
<211> LENGTH: 99
<212> TYPE: DNA
<213> ORGANISM: Artificial Sequence
<220> FEATURE:
<221> NAME/KEY: variation
<222> LOCATION: (46)...(54)
<223> OTHER INFORMATION: N = A, G, C, T; S = G, C; Degenerate
      Oligonucleotides

<400> SEQUENCE: 52
acagtcaaga tctcctgcaa gggttctgga tataccttca cacacnnsnn snnsaactgg   60
gtgaagcaga ctccaagaaa ggatttaaag tggatgggc                          99

<210> SEQ ID NO 53
<211> LENGTH: 99
<212> TYPE: DNA
<213> ORGANISM: Artificial Sequence
<220> FEATURE:
<221> NAME/KEY: variation
<222> LOCATION: (49)...(57)
<223> OTHER INFORMATION: N = A, G, C, T; S = G, C; Degenerate
      Oligonucleotides

<400> SEQUENCE: 53
acagtcaaga tctcctgcaa gggttctgga tataccttca cacactatnn snnsnnstgg   60
gtgaagcaga ctccaagaaa ggatttaaag tggatgggc                          99

<210> SEQ ID NO 54
<211> LENGTH: 99
<212> TYPE: DNA
<213> ORGANISM: Artificial Sequence
<220> FEATURE:
<221> NAME/KEY: variation
<222> LOCATION: (40)...(48)
<223> OTHER INFORMATION: N = A, G, C, T; S = G, C; Degenerate
      Oligonucleotides

<400> SEQUENCE: 54
ttggctgtgt ctctagggca gagggccacc atctcctgcn nsnnsnnsca aagtgttgat   60
tataatggtg atagttatct gaactggtac caacagaag                          99
```

```
<210> SEQ ID NO 55
<211> LENGTH: 99
<212> TYPE: DNA
<213> ORGANISM: Artificial Sequence
<220> FEATURE:
<221> NAME/KEY: variation
<222> LOCATION: (43)...(51)
<223> OTHER INFORMATION: N = A, G, C, T; S = G, C; Degenerate
      Oligonucleotides

<400> SEQUENCE: 55
ttggctgtgt ctctagggca gagggccacc atctcctgca agnnsnnsnn sagtgttgat      60
tataatggtg atagttatct gaactggtac aacagaag                             99

<210> SEQ ID NO 56
<211> LENGTH: 99
<212> TYPE: DNA
<213> ORGANISM: Artificial Sequence
<220> FEATURE:
<221> NAME/KEY: variation
<222> LOCATION: (46)...(54)
<223> OTHER INFORMATION: N = A, G, C, T; S = G, C; Degenerate
      Oligonucleotides

<400> SEQUENCE: 56
ttggctgtgt ctctagggca gagggccacc atctcctgca aggccnnsnn snnsgttgat      60
tataatggtg atagttatct gaactggtac aacagaag                             99

<210> SEQ ID NO 57
<211> LENGTH: 99
<212> TYPE: DNA
<213> ORGANISM: Artificial Sequence
<220> FEATURE:
<221> NAME/KEY: variation
<222> LOCATION: (49)...(57)
<223> OTHER INFORMATION: N = A, G, C, T; S = G, C; Degenerate
      Oligonucleotides

<400> SEQUENCE: 57
ttggctgtgt ctctagggca gagggccacc atctcctgca aggccagcnn snnsnnsgat      60
tataatggtg atagttatct gaactggtac aacagaag                             99

<210> SEQ ID NO 58
<211> LENGTH: 99
<212> TYPE: DNA
<213> ORGANISM: Artificial Sequence
<220> FEATURE:
<221> NAME/KEY: variation
<222> LOCATION: (52)...(60)
<223> OTHER INFORMATION: N = A, G, C, T; S = G, C; Degenerate
      Oligonucleotides

<400> SEQUENCE: 58
ttggctgtgt ctctagggca gagggccacc atctcctgca aggccagcca annsnnsnns      60
tataatggtg atagttatct gaactggtac aacagaag                             99

<210> SEQ ID NO 59
<211> LENGTH: 99
<212> TYPE: DNA
<213> ORGANISM: Artificial Sequence
<220> FEATURE:
<221> NAME/KEY: variation
<222> LOCATION: (40)...(48)
<223> OTHER INFORMATION: N = A, G, C, T; S = G, C; Degenerate
      Oligonucleotides

<400> SEQUENCE: 59
```

-continued gggcagaggg ccaccatctc ctgcaaggcc agccaaagtn nsnnsnnsaa tggtgatagt        60
tatctgaact ggtaccaaca gaagccagga cagccaccc                              99

<210> SEQ ID NO 60
<211> LENGTH: 99
<212> TYPE: DNA
<213> ORGANISM: Artificial Sequence
<220> FEATURE:
<221> NAME/KEY: variation
<222> LOCATION: (43)...(51)
<223> OTHER INFORMATION: N = A, G, C, T; S = G, C; Degenerate
      Oligonucleotides

<400> SEQUENCE: 60
gggcagaggg ccaccatctc ctgcaaggcc agccaaagtg ttnnsnnsnn sggtgatagt        60
tatctgaact ggtaccaaca gaagccagga cagccaccc                              99

<210> SEQ ID NO 61
<211> LENGTH: 99
<212> TYPE: DNA
<213> ORGANISM: Artificial Sequence
<220> FEATURE:
<221> NAME/KEY: variation
<222> LOCATION: (46)...(54)
<223> OTHER INFORMATION: N = A, G, C, T; S = G, C; Degenerate
      Oligonucleotides

<400> SEQUENCE: 61
gggcagaggg ccaccatctc ctgcaaggcc agccaaagtg ttgatnnsnn snnsgatagt        60
tatctgaact ggtaccaaca gaagccagga cagccaccc                              99

<210> SEQ ID NO 62
<211> LENGTH: 99
<212> TYPE: DNA
<213> ORGANISM: Artificial Sequence
<220> FEATURE:
<221> NAME/KEY: variation
<222> LOCATION: (49)...(57)
<223> OTHER INFORMATION: N = A, G, C, T; S = G, C; Degenerate
      Oligonucleotides

<400> SEQUENCE: 62
gggcagaggg ccaccatctc ctgcaaggcc agccaaagtg ttgattatnn snnsnnsagt        60
tatctgaact ggtaccaaca gaagccagga cagccaccc                              99

<210> SEQ ID NO 63
<211> LENGTH: 99
<212> TYPE: DNA
<213> ORGANISM: Artificial Sequence
<220> FEATURE:
<221> NAME/KEY: variation
<222> LOCATION: (52)...(60)
<223> OTHER INFORMATION: N = A, G, C, T; S = G, C; Degenerate
      Oligonucleotides

<400> SEQUENCE: 63
gggcagaggg ccaccatctc ctgcaaggcc agccaaagtg ttgattataa tnnsnnsnns        60
tatctgaact ggtaccaaca gaagccagga cagccaccc                              99

<210> SEQ ID NO 64
<211> LENGTH: 93
<212> TYPE: DNA
<213> ORGANISM: Artificial Sequence
<220> FEATURE:
<221> NAME/KEY: variation
<222> LOCATION: (40)...(48)

<223> OTHER INFORMATION: N = A, G, C, T; S = G, C; Degenerate
      Oligonucleotides

<400> SEQUENCE: 64
atctcctgca aggccagcca aagtgttgat tataatggtn nsnnsnnsct gaactggtac    60
caacagaagc caggacagcc acccaaattc ctc                                93

<210> SEQ ID NO 65
<211> LENGTH: 93
<212> TYPE: DNA
<213> ORGANISM: Artificial Sequence
<220> FEATURE:
<221> NAME/KEY: variation
<222> LOCATION: (43)...(51)
<223> OTHER INFORMATION: N = A, G, C, T; S = G, C; Degenerate
      Oligonucleotides

<400> SEQUENCE: 65
atctcctgca aggccagcca aagtgttgat tataatggtg atnnsnnsnn saactggtac    60
caacagaagc caggacagcc acccaaattc ctc                                93

<210> SEQ ID NO 66
<211> LENGTH: 93
<212> TYPE: DNA
<213> ORGANISM: Artificial Sequence
<220> FEATURE:
<221> NAME/KEY: variation
<222> LOCATION: (46)...(54)
<223> OTHER INFORMATION: N = A, G, C, T; S = G, C; Degenerate
      Oligonucleotides

<400> SEQUENCE: 66
atctcctgca aggccagcca aagtgttgat tataatggtg atagtnnsnn snnstggtac    60
caacagaagc caggacagcc acccaaattc ctc                                93

<210> SEQ ID NO 67
<211> LENGTH: 99
<212> TYPE: DNA
<213> ORGANISM: Artificial Sequence
<220> FEATURE:
<221> NAME/KEY: variation
<222> LOCATION: (40)...(48)
<223> OTHER INFORMATION: N = A, G, C, T; S = G, C; Degenerate
      Oligonucleotides

<400> SEQUENCE: 67
caacagaagc caggacagcc acccaaattc ctcatctatn nsnnsnnsaa tctagaatct    60
gggatcccag ccaggtttag tggcagtggg tctgggaca                          99

<210> SEQ ID NO 68
<211> LENGTH: 99
<212> TYPE: DNA
<213> ORGANISM: Artificial Sequence
<220> FEATURE:
<221> NAME/KEY: variation
<222> LOCATION: (43)...(51)
<223> OTHER INFORMATION: N = A, G, C, T; S = G, C; Degenerate
      Oligonucleotides

<400> SEQUENCE: 68
caacagaagc caggacagcc acccaaattc ctcatctatg ctnnsnnsnn sctagaatct    60
gggatcccag ccaggtttag tggcagtggg tctgggaca                          99

<210> SEQ ID NO 69
<211> LENGTH: 99

```
<212> TYPE: DNA
<213> ORGANISM: Artificial Sequence
<220> FEATURE:
<221> NAME/KEY: variation
<222> LOCATION: (46)...(54)
<223> OTHER INFORMATION: N = A, G, C, T; S = G, C; Degenerate
      Oligonucleotides

<400> SEQUENCE: 69
caacagaagc caggacagcc acccaaattc ctcatctatg ctgcannsnn snnsgaatct      60
gggatcccag ccaggtttag tggcagtggg tctgggaca                            99

<210> SEQ ID NO 70
<211> LENGTH: 99
<212> TYPE: DNA
<213> ORGANISM: Artificial Sequence
<220> FEATURE:
<221> NAME/KEY: variation
<222> LOCATION: (49)...(57)
<223> OTHER INFORMATION: N = A, G, C, T; S = G, C; Degenerate
      Oligonucleotides

<400> SEQUENCE: 70
caacagaagc caggacagcc acccaaattc ctcatctatg ctgcatccnn snnsnnstct      60
gggatcccag ccaggtttag tggcagtggg tctgggaca                            99

<210> SEQ ID NO 71
<211> LENGTH: 99
<212> TYPE: DNA
<213> ORGANISM: Artificial Sequence
<220> FEATURE:
<221> NAME/KEY: variation
<222> LOCATION: (52)...(60)
<223> OTHER INFORMATION: N = A, G, C, T; S = G, C; Degenerate
      Oligonucleotides

<400> SEQUENCE: 71
caacagaagc caggacagcc acccaaattc ctcatctatg ctgcatccaa tnnsnnsnns      60
gggatcccag ccaggtttag tggcagtggg tctgggaca                            99

<210> SEQ ID NO 72
<211> LENGTH: 99
<212> TYPE: DNA
<213> ORGANISM: Artificial Sequence
<220> FEATURE:
<221> NAME/KEY: variation
<222> LOCATION: (40)...(48)
<223> OTHER INFORMATION: N = A, G, C, T; S = G, C; Degenerate
      Oligonucleotides

<400> SEQUENCE: 72
catcctgtgg aggaggagga tgctgcaacc tattactgtn nsnnsnnsaa tgaggatcca      60
ttcacgttcg gctcggggac aaagttggaa ataaaacgg                            99

<210> SEQ ID NO 73
<211> LENGTH: 99
<212> TYPE: DNA
<213> ORGANISM: Artificial Sequence
<220> FEATURE:
<221> NAME/KEY: variation
<222> LOCATION: (43)...(51)
<223> OTHER INFORMATION: N = A, G, C, T; S = G, C; Degenerate
      Oligonucleotides

<400> SEQUENCE: 73
catcctgtgg aggaggagga tgctgcaacc tattactgtc agnnsnnsnn sgaggatcca      60
```

```
ttcacgttcg gctcggggac aaagttggaa ataaaacgg                                  99

<210> SEQ ID NO 74
<211> LENGTH: 99
<212> TYPE: DNA
<213> ORGANISM: Artificial Sequence
<220> FEATURE:
<221> NAME/KEY: variation
<222> LOCATION: (46)...(54)
<223> OTHER INFORMATION: N = A, G, C, T; S = G, C; Degenerate
      Oligonucleotides

<400> SEQUENCE: 74
catcctgtgg aggaggagga tgctgcaacc tattactgtc agcaannsnn snnsgatcca           60
ttcacgttcg gctcggggac aaagttggaa ataaaacgg                                  99

<210> SEQ ID NO 75
<211> LENGTH: 99
<212> TYPE: DNA
<213> ORGANISM: Artificial Sequence
<220> FEATURE:
<221> NAME/KEY: variation
<222> LOCATION: (49)...(57)
<223> OTHER INFORMATION: N = A, G, C, T; S = G, C; Degenerate
      Oligonucleotides

<400> SEQUENCE: 75
catcctgtgg aggaggagga tgctgcaacc tattactgtc agcaaagtnn snnsnnscca           60
ttcacgttcg gctcggggac aaagttggaa ataaaacgg                                  99

<210> SEQ ID NO 76
<211> LENGTH: 99
<212> TYPE: DNA
<213> ORGANISM: Artificial Sequence
<220> FEATURE:
<221> NAME/KEY: variation
<222> LOCATION: (52)...(60)
<223> OTHER INFORMATION: N = A, G, C, T; S = G, C; Degenerate
      Oligonucleotides

<400> SEQUENCE: 76
catcctgtgg aggaggagga tgctgcaacc tattactgtc agcaaagtaa tnnsnnsnns           60
ttcacgttcg gctcggggac aaagttggaa ataaaacgg                                  99

<210> SEQ ID NO 77
<211> LENGTH: 93
<212> TYPE: DNA
<213> ORGANISM: Artificial Sequence
<220> FEATURE:
<221> NAME/KEY: variation
<222> LOCATION: (40)...(48)
<223> OTHER INFORMATION: N = A, G, C, T; S = G, C; Degenerate
      Oligonucleotides

<400> SEQUENCE: 77
gaggatgctg caacctatta ctgtcagcaa agtaatgagn nsnnsnnsac gttcggctcg           60
gggacaaagt tggaaataaa acgggcggcc gcc                                        93

<210> SEQ ID NO 78
<211> LENGTH: 93
<212> TYPE: DNA
<213> ORGANISM: Artificial Sequence
<220> FEATURE:
<221> NAME/KEY: variation
<222> LOCATION: (43)...(51)
<223> OTHER INFORMATION: N = A, G, C, T; S = G, C; Degenerate
      Oligonucleotides
```

```
<400> SEQUENCE: 78
gaggatgctg caacctatta ctgtcagcaa agtaatgagg atnnsnnsnn sttcggctcg    60
gggacaaagt tggaaataaa acgggcggcc gcc                                93

<210> SEQ ID NO 79
<211> LENGTH: 20
<212> TYPE: DNA
<213> ORGANISM: Artificial Sequence
<220> FEATURE:
<223> OTHER INFORMATION: pYD41 vector specific primers

<400> SEQUENCE: 79
tagcatgact ggtggacagc                                                20

<210> SEQ ID NO 80
<211> LENGTH: 18
<212> TYPE: DNA
<213> ORGANISM: Artificial Sequence
<220> FEATURE:
<223> OTHER INFORMATION: pYD41 rev vector specific primers

<400> SEQUENCE: 80
cgtagaatcg agaccgag                                                  18

<210> SEQ ID NO 81
<211> LENGTH: 51
<212> TYPE: DNA
<213> ORGANISM: Artificial Sequence
<220> FEATURE:
<223> OTHER INFORMATION: Heavy chain CDR 2 region of AM1

<400> SEQUENCE: 81
tggataaaca cccatactgg agaggcgtac tatgctgatg acttcaaggg a             51

<210> SEQ ID NO 82
<211> LENGTH: 45
<212> TYPE: DNA
<213> ORGANISM: Artificial Sequence
<220> FEATURE:
<223> OTHER INFORMATION: Light chain CDR 1 region of AM1

<400> SEQUENCE: 82
aaggccaact ggcccgttga ttataatggt gatagttatc tgaac                    45
```

HUMAN BNP IMMUNOSPECIFIC ANTIBODIES

RELATED APPLICATION INFORMATION

This application is a continuation application of U.S. Ser. No. 11/595,625 filed Nov. 9, 2006, now abandoned, and also claims the benefit of U.S. Application No. 60/734,964, filed Nov. 9, 2005 (expired), each of which are incorporated herein by reference in their entireties.

FIELD OF THE INVENTION

The present invention relates to antibodies that immunospecifically bind to human brain natriuretic peptide or a human brain natriuretic peptide fragment with a high binding affinity, methods for producing and selecting said antibodies, immunoassays for human brain natriuretic peptide or a human brain natriuretic peptide fragment that employ said antibodies and therapeutic compositions containing said antibodies.

BACKGROUND OF THE INVENTION

Atrial natriuretic peptide (hereinafter referred to as "ANP"), brain natriuretic peptide (hereinafter referred to as "BNP"), C-type natriuretic peptide (hereinafter referred to as "CNP") and Dendroaspis natriuretic peptide (hereinafter referred to as "DNP") are each members of a family of hormones known as "natriuretic peptides". ANP and BNP share a wide spectrum of biological properties and belong to the cardiac natriuretic system. Both ANP and BNP are of myocardial cell origin while CNP is of endothelial cell origin. DNP was isolated from the venom of the green mamba snake and possesses structural similarity to ANP, BNP and CNP.

BNP received its name because it was first isolated from porcine brain, thus "BNP" stood for "brain natriuretic peptide". However, because BNP belongs to the cardiac natriuretic system, "brain" has been changed to "B-type". Therefore, "BNP" now refers to "B-type natriuretic peptide".

ANP is secreted by the heart in the atria. BNP is secreted by the heart through the coronary sinus, predominantly from the cardiac ventricles. BNP is secreted as a 108 amino acid polypeptide precursor (See Valli et al., *J. Lab. Clin. Med.*, 134(5):437-444 (November 1999)). The mature form of BNP is made up of 32 amino acids (representing amino acids 77-108 of the 108 amino acid polypeptide precursor) with a 17 amino acid ring closed by a disulfide bond between two cysteine residues, an amino-terminal tail of 9 amino acids, and a carboxyl-terminal tail of 6 amino acids. ANP and CNP also have a 17 amino acid ring closed by a disulfide bond between two cysteine residues. Eleven of the seventeen amino acids in the ring are conserved between the three molecules. In addition to the 17 amino acid ring structure, ANP has an amino-terminal tail of 6 amino acids and a carboxy-terminal tail of 5 amino acids. ANP is produced as a 126 amino acid pro-ANP form that is the major storage form of ANP. After proteolytic cleavage between amino acids 98 and 99, the mature 28 amino acid peptide ANP is found in coronary sinus plasma (See Yandle, *J. Internal Med.*, 235:561-576 (1994)).

CNP is found in the brain and cerebral spinal fluid and is the most prevalent of the three peptides in the central nervous system. Little if any CNP is present in the heart. Pro-CNP is a 103 amino acid peptide that is processed into either CNP-53 (amino acids 51 to 103) or CNP-22 (amino acids 82 to 103) that are the active peptides. In addition the 17 amino acid ring structure, CNP-22 has an amino-terminal tail of 5 amino acids and contains no carboxy-terminal tail. CNP-53 is identical to CNP-22 except for a 31 amino acid extension at the amino terminal end.

As mentioned previously, DNP was isolated from the venom of the green mamba snake. The mature form of DNP is made up of 38 amino acids. DNP-like immunoreactivity (DNP-L1) has been reported in human plasma and the plasma concentration of DNP-L1 has been found to be elevated in patients with congestive heart failure (See, Cataliotti, et al., *Mayo Clin. Proc.*, 76:111-1119 (2001)). Additionally, it is also known that the infusion of synthetic DNP results in marked natriuresis and diuresis in association with increased plasma and urinary cyclic guanosine monophosphate. Id.

One of the problems with natural human natriuretic peptides is that they are unstable in plasma and serum. Specifically, enzymes, such as proteases, cleave these peptides. For example, proteases cleave BNP (natural and synthetic) at various locations along its amino acid chain. For example, protease cleavage is known to occur at the amino terminus of BNP between amino acids 2-3 (Shimizu et al., *Clinica Chimica Acta*, 316:129-135 (2002)) and at its carboxy terminus between amino acids 30-32. Moreover, endopeptidase cleavage of BNP is also known in the art (Davidson and Struthers, *J. Hypertension*, 12:329-336 (1994)).

The measurement of mature BNP (i.e., the 32 amino acid molecule (amino acids 77-108 of the precursor polypeptide of BNP)) in humans (hereinafter referred to has "hBNP"), in the general population has been found to reflect cardiac diseases, such as congestive heart failure, ischemic heart diseases, atrial fibrillation and renal dysfunction. In fact, elevated levels of BNP in human plasma have been reported in heart disease, following acute myocardial infarction and during symptomless or subclinical ventricular dysfunction (See Mukoyama et al., *J. Clin. Invest.*, 87:11402-11412 (1991), Motwani et al., *Lancet*, 341:1109-1113 (1993), Yoshibayashi et al., *New Eng. J. Med.*, 327:434 (1992)). Increased circulating levels of ANP are seen in congestive heart failure, chronic renal failure and in severe hypertension. The presence of CNP in human plasma remains controversial with reports of its absence or presence as CNP-22 (See Yandle, *J. Internal Med.*, 235:561-576 (1994)).

A ligand binding assay is an analytical technique for measuring concentrations of substances commonly referred to as ligands that react selectively with specific binding proteins. Immunoassays that measure the concentrations of antigens that react selectively with specific antibodies are an example of a class of ligand binding assays.

Ligand binding assays, such as immunoassays, for measuring human natriuretic peptides in plasma, particularly hBNP, are well-known in the art and are commercially available. These immunoassays require the use of at least one or two specific antibodies as well as at least one calibrator and, ideally, at least one control. In addition to the calibrators and controls, immunoassays require the use of at least one test sample. Test samples are normally biological samples derived from serum, plasma, whole blood or other bodily fluids (normally from a human patient). The levels of at least one human natriuretic peptide in the test sample is quantified in the immunoassay.

For example, U.S. Pat. No. 6,162,902 (hereinafter referred to as the "'902 patent") discloses isolated antibodies that are monospecifically reactive to epitopes 1-10, 5-13 and 15-25 of hBNP. More particularly, the '902 patent describes two isolated monoclonal antibodies. The first monoclonal antibody is produced by hybridoma cell line 106.3 (ATCC Accession No. HB-12044) and is monospecifically reactive to epitopes 5-13 of hBNP. The second monoclonal antibody is produced by hybridoma cell line 201.3 (ATCC Accession No. HB 12045) and is monospecifically reactive to epitopes 1-10 of hBNP. The '902 patent also describes the use of the above antibodies in immunoassays for the purpose of quantifying the amount of hBNP in a biological sample. U.S. Pat. No. 6,677,124 (hereinafter referred to as the "'124 patent") discloses a monoclonal antibody that binds to an epitope having the amino acid sequence of LYS-VAL-LEU-ARG-ARG-HIS (amino acids 27-32 of SEQ ID NO:5) that is found in the C-terminal region of hBNP, namely epitopes 27-32. More particularly, the '124 patent describes a monoclonal antibody produced by hybridoma cell line BC203 (FERM BP-3515). The '124 patent also describes immunoassays for hBNP using this monoclonal antibody.

It is generally known in the art that the specificity and sensitivity of the antibodies used in immunoassays, such as hBNP immunoassays, are very important. One way in which to increase both the specificity and sensitivity of one or more antibodies is to improve the binding affinity of an antibody for its intended target (i.e., an antigen). Antibodies having an improved binding affinity for their intended targets should exhibit increased specificity and sensitivity. Therefore, there is a need in the art for new antibodies that specifically bind to human BNP with a high binding affinity and thus exhibit high specificity and sensitivity when used in said hBNP immunoassays.

BRIEF SUMMARY OF THE INVENTION

In one aspect, the present invention relates to an isolated antibody which immunospecifically binds to an epitope comprising amino acid residues 5 through 13 of human brain natriuretic peptide ("hBNP") with at least about a two fold improvement in its equilibrium dissociation constant ($K_D$) when compared with an antibody produced by hybridoma cell line 106.3, said cell line having A.T.C.C. Accession No. HB-12044. More specifically, the antibody of the present invention exhibits at least about a three fold improvement, at least about a five fold improvement, at least about a ten fold improvement, at least about a fifteen fold improvement, at least about a twenty fold improvement or at least about a twenty-five fold improvement in its $K_D$ when compared with an antibody produced by hybridoma cell line 106.3. The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof.

In another aspect, the present invention relates to an isolated antibody which immunospecifically binds to hBNP, wherein said antibody has an association rate ($k_a$) of between about $5.0 \times 10^4$ and about $1.0 \times 10^8$ M$^{-1}$s$^{-1}$. More specifically, the antibody of the present invention has an association rate of between about $3.3 \times 10^4$ and about $1.0 \times 10^9$ M$^{-1}$s$^{-1}$, between about $2.5 \times 10^4$ and about $1.0 \times 10^8$ M$^{-1}$s$^{-1}$ or between about $2.4 \times 10^4$ and about $1.35 \times 10^7$ M$^{-1}$s$^{-1}$. The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof. Additionally, this isolated antibody immunospecifically binds to an epitope comprising amino acid residues 5 through 13 of hBNP.

In another aspect, the present invention relates to an isolated antibody which immunospecifically binds to hBNP, wherein said antibody has a dissociation rate ($k_d$) of between about $1.0 \times 10^{-3}$ and about $1.0 \times 10^{-6}$·s$^{-1}$. More specifically, the antibody of the present invention has a dissociation rate of between about $1.0 \times 10^{-3}$ and about $1.0 \times 10^{-5}$·s$^{-1}$ or between about $1.0 \times 10^{-3}$ and about $1.0 \times 10^{-4}$·s$^{-1}$. The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof. Additionally, this isolated antibody immunospecifically binds to an epitope comprising amino acid residues 5 through 13 of hBNP.

In another aspect, the present invention relates to an isolated antibody which immunospecifically binds to hBNP wherein said antibody has an equilibrium dissociation constant ($K_D$) of between about $2 \times 10^{-11}$ M and about $1 \times 10^{-15}$ M. More specifically, the antibody of the present invention has an equilibrium dissociation constant of between about $3.0 \times 10^{-11}$ M and about $1.0 \times 10^{-14}$ M, between about $4.0 \times 10^{-11}$ M and about $8.0 \times 10^{-13}$ M or between about $4.2 \times 10^{-11}$ M and about $7.4 \times 10^{-13}$ M. The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof. Additionally, this isolated antibody immunospecifically binds to an epitope comprising amino acid residues 5 through 13 of hBNP.

In still another aspect, the present invention relates to a Chinese hamster ovary ("CHO") cell line AM1 having A.T.C.C. Accession No. PTA-6987.

In still yet another aspect, the present invention relates to an antibody made from DNA extracted from CHO cell line AM1 having A.T.C.C. Accession No. PTA-6987.

In yet another aspect, the present invention relates to a chimeric antibody or a hBNP-epitope binding fragment thereof produced by CHO cell line AM1, wherein said cell line has A.T.C.C. Accession No. PTA-6987.

In still a further aspect, the present invention relates to an isolated antibody which immunospecifically binds to hBNP, wherein said antibody has a variable heavy domain and a variable light domain, the variable heavy domain comprising a heavy chain complementary determining region ("CDR") 1, a heavy chain CDR 2 and a heavy chain CDR 3, the variable light domain comprising a light chain CDR 1, a light chain CDR 2 and a light chain CDR 3, wherein (a) the Heavy Chain CDR 1 has an amino acid sequence of: Gly-Tyr-Thr-Phe-Thr-His-Tyr-Gly-Ile-Asn (SEQ ID NO:6);

(b) the Heavy Chain CDR 2 has an amino acid sequence having a formula of:

(SEQ ID NO: 12)
Trp-Ile-Asn-Thr-His-Thr-Gly-Glu-Xaa$_1$-Xaa$_2$-Tyr-Ala-

Asp-Asp-Phe-Lys-Gly wherein Xaa₁ is selected from the group consisting of proline and alanine;
wherein Xaa₂ is selected from the group consisting of isoleucine and tyrosine;
(c) the Heavy Chain CDR 3 has an amino acid sequence of: Ser-His-Arg-Phe-Gly-Leu-Asp-Tyr (SEQ ID NO:8);
(d) the Light Chain CDR 1 has an amino acid sequence having a formula of:

```
                                            (SEQ ID NO: 13)
Lys-Ala-Xaa₃-Xaa₄-Xaa₅-Val-Asp-Tyr-Asn-Gly-Asp-

Ser-Tyr-Leu-Asn
``` wherein Xaa₃ is selected from the group consisting of: serine, alanine, asparagine, glutamine, tyrosine, threonine and arginine;
wherein Xaa₄ is selected from the group consisting of: glutamine, tyrosine, tryptophan, alanine and phenylalanine;
wherein Xaa₅ is selected from the group consisting of: serine, glycine, proline, alanine and aspartic acid;
(e) the Light Chain CDR 2 has an amino acid sequence having the formula of:

```
Ala-Ala-Ser-Xaa₆-Xaa₇-Xaa₈-Ser      (SEQ ID NO: 14)
``` wherein Xaa₆ is selected from the group consisting of: asparagine and cysteine;
wherein Xaa₇ is selected from the group consisting of: leucine, glycine and alanine;
wherein Xaa₈ is selected from the group consisting of glutamic acid, tryptophan and proline; and
(f) the Light Chain CDR 3 has an amino acid sequence of: Gln-Gln-Ser-Asn-Glu-Asp-Pro-Phe-Thr (SEQ ID NO:11),
wherein the heavy chain CDR 2 has an amino acid sequence other than Trp-Ile-Asn-Thr-His-Thr-Gly-Glu-Pro-Ile-Tyr-Ala-Asp-Asp-Phe-Lys-Gly (SEQ ID NO:7) when the light chain CDR 1 has the amino acid sequence of Lys-Ala-Ser-Gln-Ser-Val-Asp-Tyr-Asn-Gly-Asp-Ser-Tyr-Leu-Asn (SEQ ID NO:9) and the light chain CDR 2 has the amino acid sequence of Ala-Ala-Ser-Asn-Leu-Glu-Ser (SEQ ID NO: 10), the light chain CDR 1 has an amino acid sequence other than Lys-Ala-Ser-Gln-Ser-Val-Asp-Tyr-Asn-Gly-Asp-Ser-Tyr-Leu-Asn (SEQ ID NO:9) when the heavy chain CDR 2 has the amino acid sequence Trp-Ile-Asn-Thr-His-Thr-Gly-Glu-Pro-Ile-Tyr-Ala-Asp-Asp-Phe-Lys-Gly (SEQ ID NO:7) and the light chain CDR 2 has the amino acid sequence Ala-Ala-Ser-Asn-Leu-Glu-Ser (SEQ ID NO: 10), or the light chain CDR 2 has an amino acid sequence other than Ala-Ala-Ser-Asn-Leu-Glu-Ser (SEQ ID NO: 10) when the heavy chain CDR 2 has the amino acid sequence of Trp-Ile-Asn-Thr-His-Thr-Gly-Glu-Pro-Ile-Tyr-Ala-Asp-Asp-Phe-Lys-Gly (SEQ ID NO:7) and the light chain CDR 1 has the amino acid sequence of Lys-Ala-Ser-Gln-Ser-Val-Asp-Tyr-Asn-Gly-Asp-Ser-Tyr-Leu-Asn (SEQ ID NO:9).

More specifically, in the above-described isolated antibody:
Xaa₁ can be alanine;
Xaa₂ can be tyrosine;
Xaa₃ can be serine;
Xaa₄ can be glutamine;
Xaa₅ can be serine;
Xaa₆ can be asparagine;
Xaa₇ can be leucine; and
Xaa₈ can be glutamic acid; or In the above-described isolated antibody:
Xaa₁ can be proline;
Xaa₂ can be isoleucine;
Xaa₃ can be glutamine;
Xaa₄ can be phenylalanine;
Xaa₅ can be alanine;
Xaa₆ can be asparagine;
Xaa₇ can be leucine; and
Xaa₈ can be glutamic acid; or
In the above-described isolated antibody:
Xaa₁ can be proline;
Xaa₂ can isoleucine;
Xaa₃ can be tyrosine;
Xaa₄ can be alanine;
Xaa₅ can be serine;
Xaa₆ can be asparagine;
Xaa₇ can be leucine; and
Xaa₈ can be glutamic acid; or
In the above-described isolated antibody
Xaa₁ can be proline;
Xaa₂ can be isoleucine;
Xaa₃ can be glutamine;
Xaa₄ can be tryptophan;
Xaa₅ can be glycine;
Xaa₆ can be asparagine;
Xaa₇ can be leucine; and
Xaa₈ can be glutamic acid; or
In the above-described isolated antibody:
Xaa₁ can be proline;
Xaa₂ can be isoleucine;
Xaa₃ can be threonine;
Xaa₄ can be tryptophan;
Xaa₅ can be aspartic acid;
Xaa₆ can be asparagine;
Xaa₇ can be leucine; and
Xaa₈ can be glutamic acid; or
In the above-described isolated antibody:
Xaa₁ can be proline;
Xaa₂ can be isoleucine;
Xaa₃ can be arginine;
Xaa₄ can be tryptophan;
Xaa₅ can be proline;
Xaa₆ can be asparagine;
Xaa₇ can be leucine; and
Xaa₈ can be glutamic acid; or
In the above-described isolated antibody:
Xaa₁ can be proline;
Xaa₂ can be isoleucine;
Xaa₃ can be alanine;
Xaa₄ can be tyrosine;
Xaa₅ can be glycine;
Xaa₆ can be asparagine;
Xaa₇ can be leucine; and
Xaa₈ can be glutamic acid; or
In the above-described isolated antibody:
Xaa₁ can be proline;
Xaa₂ can be isoleucine;
Xaa₃ can be asparagine;
Xaa₄ can be tryptophan;
Xaa₅ can be proline;
Xaa₆ can be asparagine;
Xaa₇ can be leucine; and
Xaa₈ can be glutamic acid; or
In the above-described isolated antibody:
Xaa₁ can be proline;
Xaa₂ can be isoleucine;
Xaa₃ can be serine;

Xaa$_4$ can be glutamine;
Xaa$_5$ can be serine;
Xaa$_6$ can be cysteine;
Xaa$_7$ can be glycine; and
Xaa$_8$ can be tryptophan; or
In the above-described isolated antibody:
Xaa$_1$ can be proline;
Xaa$_2$ can be isoleucine;
Xaa$_3$ can be serine;
Xaa$_4$ can be glutamine;
Xaa$_5$ can be serine;
Xaa$_6$ can be cysteine;
Xaa$_7$ can be alanine; and
Xaa$_8$ can be proline.

The above-described antibody can have an equilibrium dissociation constant (K$_D$) of between about 2.0×10$^{-11}$ M and about 1.0×10$^{-15}$ M, between about 3.0×10$^{-11}$ M and about 1.0×10$^{-14}$ M, between about 4.0×10$^{-11}$ M and about 8.0×10$^{-13}$ M or between about 4.2×10$^{-11}$ M and about 7.4×10$^{-13}$ M. Additionally, the above-described antibody can have an association rate (k$_a$) of between about 5.0×10$^4$ and about 1.0×10$^8$ M$^{-1}$s$^{-1}$. Furthermore, the above-described antibody can have a dissociation rate (k$_d$) of between about 1.0×10$^{-3}$ and 1.0×10$^{-6}$ s$^{-1}$. Furthermore, the above-described antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof. Finally, the above-described antibody can immunospecifically bind to an epitope comprising amino acid residues 5 through 13 of hBNP.

In another aspect, the present invention relates to an immunoassay for hBNP or hBNP fragment, wherein said immunoassay comprises any one of the hereinbefore described antibodies of the present invention. More specifically, said immunoassay may comprise only a single antibody that immunospecifically binds to hBNP or hBNP fragment. Moreover, said immunoassay may further comprise an additional specific binding partner for hBNP or hBNP fragment.

In another aspect, the present invention relates to a pharmaceutical composition comprising a therapeutically effective amount of any of the hereinbefore described antibodies of the present invention and a pharmaceutically acceptable carrier or excipient.

BRIEF DESCRIPTION OF THE FIGURES

FIGS. 3A-3E are the nucleotide sequence of the vector shown in FIG. 2.

FIG. 5 shows the amino acid sequence of the 106.3 single-chain variable fragment ("scFv"). The solid underlined sequence represents the variable heavy chain sequence ("VH"), the double underlined sequence the linker, and the stippled underline sequence the variable light chain sequence ("VL"). Italicized and bold type indicates the complementary determining regions (CDR).

FIGS. 6A-6B show the nucleotide sequence of the 106.3 scFv.

FIG. 11 is a summary showing that 106.3scFv variants isolated from CDR mutagenic libraries exhibited improvements in off-rate (namely, said variants had a slower k$_{off}$).

FIGS. 12A-C show the sequence characterization of scFv 106.3 variants. More specifically, plasmid DNA was isolated from 106.3 variants and scFv genes were sequenced.

FIG. 13 shows affinity measurements of selected 106.3 engineered, human-mouse chimeric antibodies and mouse 106.3 mAb using surface plasmon resonance using BIAcore.

FIGS. 14A-H show the fifty-four (54) oligonucleotides that were used to create the gapped pYD41 vector discussed in Example 1.

DETAILED DESCRIPTION OF THE INVENTION

I. Introduction

Figure 1:
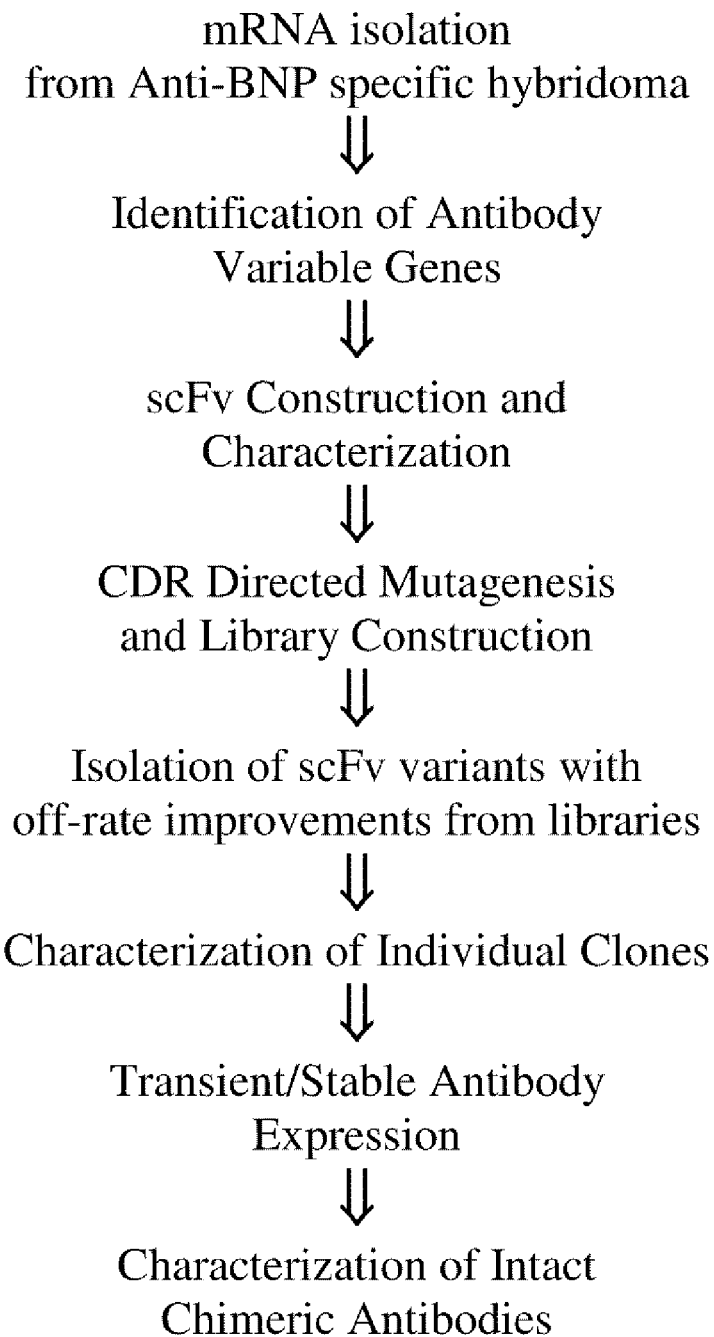
FIG. 1 is a flow chart showing the steps used to identify and create antibodies that immunospecifically bind to human BNP with a high binding affinity.

The present invention relates to novel antibodies that immunospecifically bind to human brain natriuretic peptide with a high binding affinity. The antibodies of the present invention are highly sensitive reagents and are useful in the qualitative and/or quantitative detection of hBNP or hBNP fragments in test samples. In another embodiment, the present invention relates to immunoassays that employ the antibodies of the present invention. In yet still a further embodiment, the present invention relates to therapeutic compositions comprising the antibodies of the present invention.

DEFINITIONS

As used herein, the terms "antibody" and "antibodies" refer to monoclonal antibodies, multispecific antibodies, human antibodies, humanized antibodies (fully or partially humanized), animal antibodies (in one aspect, a bird (for example, a duck or goose), in another aspect, a shark or whale, in yet another aspect, a mammal, including a non-primate (for example, a cow, pig, camel, llama, horse, goat, rabbit, sheep, hamsters, guinea pig, cat, dog, rat, mouse, etc) and a non-human primate (for example, a monkey, such as a cynomologous monkey, a chimpanzee, etc), recombinant antibodies, chimeric antibodies, single-chain Fvs (scFv), single chain antibodies, single domain antibodies, Fab fragments, F(ab')$_2$ fragments, disulfide-linked Fv (sdFv), and anti-idiotypic (anti-Id) antibodies (including, for example, anti-Id antibodies to antibodies of the present invention), and functionally active epitope-binding fragments of any of the above. In particular, antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, IgG$_1$, IgG$_2$, IgG$_3$, IgG$_4$, IgA$_1$ and IgA$_2$) or subclass.

As used herein, the term "association rate", "$k_{on}$" or "$k_a$" as used interchangeably herein, refers to the value indicating the binding strength (degree) of an antibody to its target antigen or the rate of complex formation between mAb and antigen as shown by the below:

Methods for determining association constants ($K_A$) are well known in the art. For example, a Biacore® (Sweden) assay can be used. Additionally, a KinExA® (Kinetic Exclusion Assay) assay, available from Sapidyne Instruments (Boise, Id.) can also be used.

As used herein, the term "dissociation rate", "$k_{off}$" or "$k_d$" as used interchangeably herein, refers to the value indicating the dissociation strength (degree) of an antibody from its target antigen or separation of Ab-Ag complex over time into free mAb and antigen as shown by the below:

Methods for determining dissociation constants ($K_D$) are well known in the art. For example, a Biacore® (Sweden) assay can be used. Additionally, a KinExA® (Kinetic Exclusion Assay) assay, available from Sapidyne Instruments (Boise, Id.) can also be used.

As used herein, the term "epitope" or "epitopes" refers to sites or fragments of a polypeptide or protein having antigenic or immunogenic activity in a subject. An epitope having immunogenic activity is a site or fragment of a polypeptide or protein that elicits an antibody response in an animal. An epitope having antigenic activity is a site or fragment of a polypeptide or protein to which an antibody immunospecifically binds as determined by any method well-known to those skilled in the art, for example by immunoassays.

As used herein, the term "equilibrium dissociation constant" or "$K_D$" as used interchangeably, herein, refers to the value obtained by dividing the dissociation rate ($k_{off}$) by the association rate ($k_{on}$). The association rate, the dissociation rate and the equilibrium dissociation constant are used to represent the binding affinity of an antibody to an antigen.

As used herein, the term "human brain natriuretic peptide", "human BNP", "hBNP", "hBNP peptide", "B-type natriuretic peptide" or "hBNP polypeptide" refers to a 32 amino acid molecule representing amino acids 77-108 of the 108 amino acid precursor molecule of human brain natriuretic peptide.

As used herein, the term "hBNP fragment" or "hBNP peptide fragment" as used herein refers to a polypeptide that comprises at least about five contiguous amino acids of amino acids 77-108 of the 108 amino acid BNP precursor molecule. In one aspect, a hBNP fragment or hBNP peptide fragment refers to a polypeptide that comprises at least about ten contiguous amino acids residues of amino acids 77-108 of the 108 amino acid BNP precursor molecule; at least about fifteen contiguous amino acids residues of amino acids 77-108 of the 108 amino acid BNP precursor molecule; at least about 20 contiguous amino acids residues of amino acids 77-108 of the 108 amino acid BNP precursor molecule; at least about 25 contiguous amino acids residues of amino acids 77-108 of the 108 amino acid BNP precursor molecule, or at least about 30 contiguous amino acid residues of amino acids 77-108 of the 108 amino acid BNP precursor molecule. Examples of hBNP fragments or hBNP peptide fragments include, but are not limited to, amino acid sequences containing amino acids residues 1-31, 1-30, 1-29, 1-28, 1-27, 1-26, 1-25, 1-24, 1-23, 1-22, 1-21, 1-20, 1-19, 1-18, 1-17, 1-16, 1-15, 2-32, 2-31, 2-30, 2-29, 2-28, 2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 3-32, 3-31, 3-30, 3-29, 3-28, 3-27, 3-26, 3-25, 3-24, 3-23, 3-32, 3-21, 3-20, 3-19, 3-18, 3-17, 3-16, 3-15, 3-14, 3-13, 3-12, 3-11, 3-10, 3-9, 3-8, 4-32, 4-31, 4-30, 4-29, 4-28, 4-27, 4-26, 4-25, 4-24, 4-23, 4-22, 4-21, 4-20, 4-19, 4-18, 4-17, 4-16, 4-15, 4-14, 4-13, 4-12, 4-11, 4-10, 4-9, 5-32, 5-31, 5-30, 5-29, 5-28, 5-27, 5-26, 5-25, 5-24, 5-23, 5-22, 5-21, 5-20, 5-19, 5-18, 5-17, 5-16, 5-15, 5-14, 5-13, 5-12, 5-11, 5-10, 6-32, 6-31, 6-30, 6-29, 6-28, 6-27, 6-26, 6-25, 6-24, 6-23, 6-22, 6-21, 6-20, 6-19, 6-18, 6-17, 6-16, 6-15, 6-14, 6-13, 6-12, 6-11, 7-32, 7-31, 7-30, 7-29, 7-28, 7-27, 7-26, 7-25, 7-24, 7-23, 7-22, 7-21, 7-20, 7-19, 7-18, 7-17, 7-16, 7-15, 7-14, 7-13, 7-12, 8-32, 8-31, 8-30, 8-29, 8-28, 8-27, 8-26, 8-25, 8-24, 8-23, 8-22, 8-21, 8-20, 8-19, 8-18, 8-17, 8-16, 8-15, 8-14, 8-13, 9-32, 9-31, 9-30, 9-29, 9-28, 9-27, 9-26, 9-25, 9-24, 9-23, 9-22, 9-21, 9-20, 9-19, 9-18, 9-17, 9-16, 9-15, 9-14, 10-32, 10-31, 10-30, 10-29, 10-28, 10-27, 10-26, 10-25, 10-24, 10-23, 10-22, 10-21, 10-20, 10-19, 10-18, 10-17, 10-16, 10-15, 11-32, 11-31, 11-30, 11-29, 11-28, 11-27, 11-26, 11-25, 11-24, 11-23, 11-22, 11-21, 11-20, 11-19, 11-18, 11-17 or 11-16 of hBNP (SEQ ID NO:5).

As used herein, the term "humanized" antibody refers to an immunoglobulin variant or fragment thereof, which is capable of binding to a predetermined antigen and which comprises framework regions having substantially the amino acid sequence of a human immunoglobulin and CDRs having substantially the amino acid sequence of a non-human immunoglobulin. Ordinarily, a humanized antibody has one or more amino acid residues introduced into it from a source that is non-human. In general, the humanized antibody will include substantially all of at least one, and typically two, variable domains (Fab, Fab', F(ab')$_2$, Fabc, Fv) in which all or substantially all of the CDR regions correspond to those of a non-human immunoglobulin and all or substantially all of the FR regions are those of a human immunoglobulin consensus sequence. The humanized antibody optimally comprises at least a portion of an immunoglobulin constant region (Fc), typically that of a human immunoglobulin. Generally, the antibody will contain both the light chain as well as at least the variable domain of a heavy chain. The humanized antibody can be selected from any class of immunoglobulins, including IgM, IgG, IgD, IgA and IgE, and any isotype, including IgG$_1$, IgG$_2$, IgG$_3$ and IgG$_4$. The humanized antibody may comprise sequences from more than one class or isotype, and selecting particular constant domains to optimize desired effector functions is within those skilled in the art.

As used herein, the phrase "immunospecifically binds to a human brain natriuretic peptide", "immunospecifically binds to hBNP", "immunospecifically binds to human brain natriuretic peptide fragment" or "immunospecifically binds to hBNP fragment" and analogous terms thereof refer to peptides, polypeptides, proteins, fusion proteins and antibodies that specifically bind to hBNP or hBNP fragment and do not specifically bind to other peptides. A peptide, polypeptide, protein, or antibody that immunospecifically binds to hBNP or hBNP fragment may bind to other peptides, polypeptides, or proteins with lower binding affinity as determined by, for example, immunoassays, BIAcore, or other assays known in the art. Antibodies or antibody fragments that immunospecifically bind to hBNP or hBNP fragment can be identified, for example, by immunoassays, BIAcore, or other techniques known to those of skill in the art. An antibody binds immunospecifically to a hBNP peptide or hBNP fragment when it binds to hBNP or hBNP fragment with a higher binding affinity than to any cross-reactive antigen as determined using experimental techniques, such as, but not limited to, radioimmunoassays (RIA) and enzyme-linked immunosorbent assays (ELISAs) (See, for example, Paul, ed., *Fundamental Immunology*, 2nd ed., Raven Press, New York, pages 332-336 (1989) for a discussion regarding antibody specificity.). In one aspect of the present invention, an antibody binds immunospecifically to hBNP or hBNP fragment when it has an equilibrium dissociation constant ($K_D$) for the hBNP or hBNP fragment of at least $2.0 \times 10^{-11}$ M as determined by a BIAcore assay under standard assay conditions, and in particular the BIAcore assay described in Example 1.

As used herein, the term "isolated" in the context of nucleic acid molecules refers to a nucleic acid molecule which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In one aspect, nucleic acid molecules are isolated. In another aspect, a nucleic acid molecule encoding an antibody of the invention is isolated.

As used herein, the term "stringent conditions" refers to hybridization to filter-bound DNA in 6× sodium chloride/sodium citrate (SSC) at about 45° C. followed by one or more washes in 0.2×SSC/0.1% SDS at about 50-65° C. The term "under highly stringent conditions", refers to hybridization to filter-bound nucleic acid in 6×SSC at about 45° C. followed by one or more washes in 0.1×SSC/0.2% SDS at about 68° C., or under other stringent hybridization conditions which are known to those skilled in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3).

As used herein, the terms "subject" and "patient" are used interchangeably. As used herein, the terms "subject" and "subjects" refer to an animal, in one aspect, a bird (for example, a duck or goose), in another aspect, a shark or whale, or in a further aspect, a mammal including, a non-primate (for example, a cow, pig, camel, llama, horse, goat, rabbit, sheep, hamsters, guinea pig, cat, dog, rat, and mouse) and a primate (for example, a monkey, such as a cynomolgous monkey, chimpanzee, and a human).

As used herein, the term "test sample" refers to a biological sample derived from serum, plasma, whole blood, lymph, CNS fluid, urine or other bodily fluids of a subject. The test sample can be prepared using routine techniques known to those skilled in the art.

As used herein, the term "therapeutically effective amount" or "pharmaceutically effective amount" means an amount of antibody or antibody portion effective, at dosages and for periods of time necessary, to achieve the desired therapeutic result. The exact dose will be ascertainable by one skilled in the art. As known in the art, adjustments based on age, body weight, sex, race, diet, time of administration, drug interaction and severity of condition may be necessary and will be ascertainable with routine experimentation by those skilled in the art. A therapeutically effective amount is also one in which the therapeutically beneficial effects outweigh any toxic or detrimental effects of the antibody or antibody fragment. A "prophylactically effective amount" refers to an amount effective, at dosages and for periods of time necessary to achieve the desired prophylactic result. Typically, since a prophylactic dose is used in subjects prior to or at an earlier stage of disease, the prophylactically effective amount will be less than the therapeutically effective amount.

II. Antibodies of the Present Invention

The present invention provides antibodies that immunospecifically bind to hBNP or hBNP fragment. In particular, the present invention provides for antibodies that have a high binding affinity for hBNP or hBNP fragment. Specifically, in one aspect, the present invention relates to an antibody that immunospecifically binds to an epitope comprising amino acid residues 5 through 13 of hBNP or hBNP fragment with at least about a two fold improvement in its equilibrium dissociation constant ($K_D$) when compared with an antibody produced by hybridoma cell line 106.3, said cell line having A.T.C.C. Accession No. HB-12044 (which is also referred to herein as the "wildtype"). More specifically, the antibodies of the present invention immunospecifically bind to an epitope comprising amino acid residues 5 through 13 of hBNP or hBNP fragment thereof with at least about a three fold improvement, at least about a five fold improvement, at least about a ten fold improvement, at least about a fifteen fold improvement, at least about a twenty fold improvement, at least about a twenty-five fold improvement, at least about a thirty fold improvement, at least about a thirty-five fold improvement, at least about a forty fold improvement, at least about a forty-five fold improvement, at least about a fifty fold improvement, at least about a fifty-five fold improvement, at least about a sixty fold improvement, at least about a seventy fold improvement or at least about a seventy-five fold improvement in its equilibrium dissociation constant ($K_D$) when compared with an antibody produced by hybridoma cell line 106.3 (the wildtype).

In another aspect, the present invention relates to an antibody that immunospecifically binds to hBNP or hBNP fragment and has a $k_{on}$ (or $k_a$) of at least about $2.4\times10^4$ $M^{-1}s^{-1}$, of at least about $2.5\times10^4$ $M^{-1}s^{-1}$, of at least about $3.3\times10^4$ $M^{-1}s^{-1}$, of at least about $5.0\times10^4$ $M^{-1}s^{-1}$, of at least about $1.25\times10^7$ $M^{-1}s^{-1}$ of at least about $1.35\times10^7$ $M^{-1}s^{-1}$, of at least about $1.0\times10^8$ $M^{-1}s^{-1}$, of at least about $1.0\times10^9$ $M^{-1}s^{-1}$, or has a $k_{on}$ (or $k_a$) ranging from about $5.0\times10^4$ $M^{-1}s^{-1}$ to about $1.0\times10^8$ $M^{-1}s^{-1}$, from about $3.3\times10^4$ $M^{-1}s^{-1}$ to about $1.0\times10^9$ $M^{-1}s^{-1}$, from about $2.5\times10^4$ $M^{-1}s^{-1}$ to about $1.25\times10^7$ $M^{-1}s^{-1}$, from about $2.4\times10^4$ $M^{-1}s^{-1}$ to about $1.35\times10^7$ $M^{-1}s^{-1}$.

In another aspect, an antibody of the present invention immunospecifically binds to the amino acid residues 5 through 13 of human BNP or hBNP fragment at a $k_{on}$ (or $k_a$) of at least about $2.4\times10^4$ $M^{-1}s^{-1}$, of at least about $2.5\times10^4$ $M^{-1}s^{-1}$, of at least about $3.3\times10^4$ $M^{-1}s^{-1}$, of at least about $5.0\times10^4$ $M^{-1}s^{-1}$, of at least about $1.25\times10^7$ $M^{-1}s^{-1}$ of at least about $1.35\times10^7$ $M^{-1}s^{-1}$, of at least about $1.0\times10^8$ $M^{-1}s^{-1}$, of at least about $1.0\times10^9$ $M^{-1}s^{-1}$, or has a $k_{on}$ (or $k_a$) ranging from about $5.0\times10^4$ $M^{-1}s^{-1}$ to about $1.0\times10^8$ $M^{-1}s^{-1}$, from about $3.3\times10^4$ $M^{-1}s^{-1}$ to about $1.0\times10^9$ $M^{-1}s^{-1}$, from about $2.5\times10^4$ $M^{-1}s^{-1}$ to about $1.25\times10^7$ $M^{-1}s^{-1}$, from about $2.4\times10^{-11}$ $M^{-1}s^{-1}$ to about $1.35\times10^7$ $M^{-1}s^{-1}$.

In another aspect, the present invention provides antibodies produced by Chinese hamster ovary cell line AM1 (also known as 106.3 L1 B24/H2288). Antibodies produced by this cell line bind to amino acid residues 5 thorough 13 of hBNP or hBNP fragment at a $k_{on}$ (or $k_a$) of at least about $2.4\times10^4$ $M^{-1}s^{-1}$, of at least about $2.5\times10^4$ $M^{-1}s^{-1}$, of at least about $3.3\times10^4$ $M^{-1}s^{-1}$, of at least about $5.0\times10^4$ $M^{-1}s^{-1}$, of at least about $1.25\times10^7$ $M^{-1}s^{-1}$ of at least about $1.35\times10^7$ $M^{-1}s^{-1}$, of at least about $1.0\times10^8$ $M^{-1}s^{-1}$, of at least about $1.0\times10^9$ $M^{-1}s^{-1}$, or has a $k_{on}$ (or $k_a$) ranging from about $5.0\times10^4$ $M^{-1}s^{-1}$ to about $1.0\times10^8$ $M^{-1}s^{-1}$, from about $3.3\times10^4$ $M^{-1}s^{-1}$ to about $1.0\times10^9$ $M^{-1}s^{-1}$, from about $2.5\times10^4$ $M^{-1}s^{-1}$ to about $1.25\times10^7$ $M^{-1}s^{-1}$, from about $2.4\times10^{-11}$ $M^{-1}s^{-1}$ to about $1.35\times10^7$ $M^{-1}s^{-1}$.

The present invention provides antibodies that immunospecifically bind to hBNP or hBNP fragment. In particular, the present invention provides for antibodies that have a high binding affinity for hBNP or hBNP fragment. More specifically, in one aspect, an antibody that immunospecifically binds to hBNP or hBNP fragment and has a $k_{off}$ (or $k_d$) of at least $1.0\times10^{-3}$ $s^{-1}$, of at least $1.0\times10^{-4}$ $s^{-1}$, of at least $1.0\times10^{-5}$ $s^{-1}$, of at least $1.0\times10^{-6}$ $s^{-1}$ or has a $k_{off}$ (or $k_d$) ranging from $1.0\times10^{-3}$ $s^{-1}$ to $1.0\times10^{-6}$ $s^{-1}$, from $1.0\times10^{-3}$ $s^{-1}$ to $1.0\times10^{-5}$ $s^{-1}$ or from $1.0\times10^{-3}$ $s^{-1}$ to $1.0\times10^{-4}$ $s^{-1}$.

In another aspect, an antibody of the present invention immunospecifically binds to the amino acid residues 5 through 13 of human BNP or hBNP fragment at a $k_{off}$ (or $k_{off}$) of at least $1.0\times10^{-3}$ $s^{-1}$, of at least $1.0\times10^{-4}$ $s^{-1}$, of at least $1.0\times10^{-5}$ $s^{-1}$, of at least $1.0\times10^{-6}$ $s^{-1}$ or has a $k_{off}$ (or $k_d$) ranging from $1.0\times10^{-3}$ $s^{-1}$ to $1.0\times10^{-6}$ $s^{-1}$, from $1.0\times10^{-3}$ $s^{-1}$ to $1.0\times10^{-5}$ $s^{-1}$ or from $1.0\times10^{-3}$ $s^{-1}$ to $1.0\times10^{-4}$ $s^{-1}$.

In another aspect, the present invention provides antibodies produced by Chinese hamster ovary cell line AM1. Antibodies produced by this cell line bind to amino acid residues 5 thorough 13 of hBNP or hBNP fragment at a $k_{off}$ (or $k_d$) of at least $1.0\times10^{-3}$ $s^{-1}$, of at least $1.0\times10^{-4}$ $s^{-1}$, of at least $1.0\times10^{-5}$ $s^{-1}$, of at least $1.0\times10^{-6}$ $s^{-1}$ or has a $k_{off}$ (or $k_d$) ranging from $1.0\times10^{-3}$ $s^{-1}$ to $1.0\times10^{-6}$ $s^{-1}$, from $1.0\times10^{-3}$ $s^{-1}$ to $1.0\times10^{-5}$ $s^{-1}$ or from $1.0\times10^{-3}$ $s^{-1}$ to $1.0\times10^{-4}$ $s^{-1}$.

The present invention provides antibodies that immunospecifically bind to hBNP or hBNP fragment. In particular, the present invention provides for antibodies that have a high binding affinity for hBNP or hBNP fragment. More specifically, in one aspect, the present invention relates to an antibody that immunospecifically binds to hBNP or hBNP fragment and has a $K_D$ of at least $2.0\times10^{-11}$ M, of at least $3.0\times10^{-11}$ M, of at least $4.0\times10^{-11}$ M, of at least $4.2\times10^{-11}$ M, of at least $1.0\times10^{-12}$ M of at least $1.0\times10^{-13}$ M, of at least $7.4\times10^{-13}$ M, of at least $8.0\times10^{-13}$ M, of at least $1.0\times10^{-14}$ M, of at least $1.0\times10^{-15}$ M, or has a $K_D$ ranging from $2.0\times10^{-11}$ M to $1.0\times10^{-15}$ M, from $3.0\times10^{-11}$ M to $1\times10^{-14}$ M, from $4.0\times10^{-11}$ M to $8.0\times10^{-13}$ M or from $4.2\times10^{-11}$ M to $7.4\times10^{-13}$ M.

In another aspect, an antibody of the present invention immunospecifically binds to the amino acid residues 5 through 13 of human BNP at a $K_D$ of at least $2.0\times10^{-11}$ M, of at least $3.0\times10^{-11}$ M, of at least $4.0\times10^{-11}$ M, of at least $4.2\times10^{-11}$ M, of at least $1.0\times10^{-12}$ M of at least $1.0\times10^{-13}$ M, of at least $7.4\times10^{-13}$ M, of at least $8.0\times10^{-13}$ M, of at least $1.0\times10^{-14}$ M, of at least $1.0\times10^{-15}$ M, or has a $K_D$ ranging from $2.0\times10^{-11}$ M to $1.0\times10^{-15}$ M, from $3.0\times10^{-11}$ M to $1\times10^{14}$ M, from $4.0\times10^{-11}$ M to $8.0\times10^{-13}$ M or from $4.2\times10^{-11}$ M to $7.4\times10^{-13}$ M.

In another aspect, the present invention provides antibodies produced by Chinese hamster ovary (CHO) cell line AM1. Antibodies produced by this cell line bind to amino acid residues 5 thorough 13 of hBNP or hBNP fragment at a $K_D$ of from $4.2\times10^{-11}$ M to $7.4\times10^{-13}$ M.

In another aspect, the antibodies of the present invention are derivatives or variants of the antibodies produced by hybridoma cell line 106.3 (ATCC Accession No. HB-12044). More specifically, the inventors of the present invention have discovered that antibodies that are derivatives or variants of the antibodies produced by hybridoma cell line 106.3 can be produced which exhibit a high binding affinity to hBNP or hBNP fragment. More specifically, the antibodies of the present invention exhibit a $k_{on}$ (or $k_a$) of at least about $2.4\times10^4$ $M^{-1}s^{-1}$, of at least about $2.5\times10^4$ $M^{-1}s^{-1}$, of at least about $3.3\times10^4$ $M^{-1}s^{-1}$, of at least about $5.0\times10^4$ $M^{-1}s^{-1}$, of at least about $1.25\times10^7$ $M^{-1}s^{-1}$ of at least about $1.35\times10^7$ $M^{-1}s^{-1}$, of at least about $1.0\times10^8$ $M^{-1}s^{-1}$, of at least about $1.0\times10^9$ $M^{-1}s^{-1}$, or have a $k_{on}$ (or $k_a$) ranging from about $5.0\times10^4$ $M^{-1}s^{-1}$ to about $1.0\times10^8$ $M^{-1}s^{-1}$, from about $3.3\times10^4$ $M^{-1}s^{-1}$ to about $1.0\times10^9$ $M^{-1}s^{-1}$, from about $2.5\times10^4$ $M^{-1}s^{-1}$ to about $1.25\times10^7$ $M^{-1}s^{-1}$, from about $2.4\times10^{-11}$ $M^{-1}s^{-1}$ to about $1.35\times10^7$ $M^{-1}s^{-1}$, a $k_{off}$ (or $k_d$) of at least $1.0\times10^{-3}$ $s^{-1}$, of at least $1.0\times10^{-4}$ $s^{-1}$, of at least $1.0\times10^{-5}$ $s^{-1}$, of at least $1.0\times10^{-6}$ $s^{-1}$ or have a $k_{off}$ (or $k_d$) ranging from $1.0\times10^{-3}$ $s^{-1}$ to $1.0\times10^{-6}$ s$^{-1}$, from $1.0\times10^{-3}$ s$^{-1}$ to $1.0\times10^{-5}$ s$^{-1}$ or from $1.0\times10^{-3}$ s$^{-1}$ to $1.0\times10^{4}$ s$^{-1}$ and a $K_D$ of at least $2.0\times10^{-11}$ M, of at least $3.0\times10^{-11}$ M, of at least $4.0\times10^{-11}$ M, of at least $4.2\times10^{-11}$ M, of at least $1.0\times10^{-12}$ M of at least $1.0\times10^{-13}$ M, of at least $7.4\times10^{-13}$ M, of at least $8.0\times10^{-13}$ M, of at least $1.0\times10^{-14}$ M, of at least $1.0\times10^{-15}$ M, or have a $K_D$ ranging from $2.0\times10^{-11}$ M to $1.0\times10^{-5}$ M, from $3.0\times10^{-1}$ M to $1\times10^{-14}$M, from $4.0\times10^{-1}$ M to $8.0\times10^{-13}$ M or from $4.2\times10^{-11}$ M to $7.4\times10^{-13}$ M. The derived or variant antibodies of the present invention comprise at least one mutation (such as deletions, additions and/or substitutions) in at least one of the heavy chain complementary determining ("CDR") regions (for example, the heavy chain CDR 1, heavy chain CDR 2 and/or heavy chain CDR 3), and/or at least one mutation (such as deletions, additions and/or substitutions) in the light chain CDR regions (for example, the light chain CDR 1, light chain CDR 2, and/or light chain CDR 3) when compared to the amino acid sequence of the antibody produced by hybridoma cell line 106.3 (also referred to herein as the "wildtype"). Moreover, the antibodies of the present invention may also contain one or more other mutations (such as deletions, additions and/or substitutions) in a part or portion of the antibody other than the CDR, such as, but not limited to, the framework region of an antibody. Methods for creating such derivatives are well known in the art and include the use of site-directed mutagenesis and PCR-mediated mutagenesis, which will be discussed in more detail infra.

More specifically, in another aspect, the antibody of the present invention immunospecifically binds to hBNP or hBNP fragment and comprises a heavy chain CDR 2 having an amino acid sequence of the formula of:

```
                                       (SEQ ID NO: 12)
Trp-Ile-Asn-Thr-His-Thr-Gly-Glu-Xaa₁-Xaa₂-Tyr-Ala-

Asp-Asp-Phe-Lys-Gly
``` where Xaa₁ is selected from the group consisting of proline and alanine and Xaa₂ is selected from the group consisting of isoleucine and tyrosine, provided that when Xaa₁ is proline, Xaa₂ is not isoleucine.

In yet a further aspect, the antibody of the present invention immunospecifically binds to hBNP or hBNP fragment and comprises a heavy chain CDR 2 having the amino acid sequence shown in SEQ ID NO:15. In another aspect, the present invention relates to an antibody that immunospecifically binds to hBNP or hBNP fragment that comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to an amino acid sequence of SEQ ID NO: 15.

In yet another aspect, the antibody of the present invention immunospecifically binds to hBNP or hBNP fragment and comprises a light chain CDR 1 that has an amino acid sequence having a formula of:

```
                                       (SEQ ID NO: 13)
Lys-Ala-Xaa₃-Xaa₄-Xaa₅-Val-Asp-Tyr-Asn-Gly-Asp-

Ser-Tyr-Leu-Asn
``` where Xaa₃ is selected from the group consisting of: serine, alanine, asparagine, glutamine, tyrosine, threonine and arginine; where Xaa₄ is selected from the group consisting of: glutamine, tyrosine, tryptophan, alanine and phenylalanine and where Xaa₅ is selected from the group consisting of: serine, glycine, proline, alanine and aspartic acid, provided that Xaa₃ is not serine when Xaa₄ is glutamine and Xaa₅ is serine.

In yet a further aspect, the antibody immunospecifically binds to hBNP or hBNP fragment and has a light chain CDR 1 having the amino acid sequence of SEQ ID NO:16, SEQ ID NO: 17, SEQ ID NO:18, SEQ ID NO:19, SEQ ID NO:20, SEQ ID NO: 21 or SEQ ID NO:22. In another aspect, the present invention relates to an antibody that immunospecifically binds to hBNP or hBNP fragment that comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to an amino acid sequence of SEQ ID NO:16, SEQ ID NO: 17, SEQ ID NO:18, SEQ ID NO:19, SEQ ID NO:20, SEQ ID NO: 21 or SEQ ID NO:22.

In yet another aspect, the antibody of the present invention immunospecifically binds to hBNP or hBNP fragment and comprises a light chain CDR 2 that has an amino acid sequence having a formula of:

```
Ala-Ala-Ser-Xaa₆-Xaa₇-Xaa₈-Ser        (SEQ ID NO: 14)
``` where Xaa₆ is selected from the group consisting of: asparagine and cysteine, where Xaa₇ is selected from the group consisting of: leucine, glycine and alanine and where Xaa₈ is selected from the group consisting of glutamic acid, tryptophan and proline, provided that Xaa₆ is not asparagine when Xaa₇ is leucine and Xaa₈ is glutamic acid.

In yet a further aspect, the antibody immunospecifically binds to hBNP or hBNP fragment and has a light chain CDR 2 having the amino acid sequence of SEQ ID NO:23 or SEQ ID NO: 24. In another aspect, the present invention relates to an antibody that immunospecifically binds to hBNP or hBNP fragment that comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to an amino acid sequence of SEQ ID NO:23 or SEQ ID NO:24.

In yet a further aspect, the antibody of the present invention immunospecifically binds to hBNP or hBNP fragment and has a heavy chain CDR 1, heavy chain CDR 2, heavy chain CDR 3, a light chain CDR 1, a light chain CDR 2 and a light variable CDR 3 comprising the following amino acid sequences:

(a) Heavy Chain CDR 1 having an amino acid sequence of: Gly-Tyr-Thr-Phe-Thr-His-Tyr-Gly-Ile-Asn (SEQ ID NO:6);

(b) Heavy Chain CDR 2 having an amino acid sequence having a formula of:

```
                                       (SEQ ID NO: 12)
Trp-Ile-Asn-Thr-His-Thr-Gly-Glu-Xaa₁-Xaa₂-Tyr-Ala-

Asp-Asp-Phe-Lys-Gly
``` where Xaa₁ is selected from the group consisting of proline and alanine;

where Xaa₂ is selected from the group consisting of isoleucine and tyrosine;

(c) Heavy Chain CDR 3 having an amino acid sequence of: Ser-His-Arg-Phe-Gly-Leu-Asp-Tyr (SEQ ID NO:8);

(d) Light Chain CDR 1 having an amino acid sequence having a formula of:

Lys-Ala-Xaa$_3$-Xaa$_4$-Xaa$_5$-Val-Asp-Tyr-Asn-Gly-Asp-Ser-Tyr-Leu-Asn (SEQ ID NO: 13)

where Xaa$_3$ is selected from the group consisting of: serine, alanine, asparagine, glutamine, tyrosine, threonine and arginine;

acid sequence of Lys-Ala-Ser-Gln-Ser-Val-Asp-Tyr-Asn-Gly-Asp-Ser-Tyr-Leu-Asn (SEQ ID NO:9).

Preferably, the antibodies having the above-described formulas comprise a heavy chain CDR 1, heavy chain CDR 2, heavy chain CDR 3, light chain CDR 1, light chain CDR 2 and light chain CDR 3 where Xaa$_1$-Xaa$_8$ in the above described formulas have the amino acid residues shown below in Table 2:

TABLE 2

| Xaa$_1$ | Xaa$_2$ | Xaa$_3$ | Xaa$_4$ | Xaa$_5$ | Xaa$_6$ | Xaa$_7$ | Xaa$_8$ |
|---|---|---|---|---|---|---|---|
| alanine | Tyrosine | serine | Glutamine | serine | asparagine | leucine | glutamic acid |
| proline | Isoleucine | glutamine | phenylalanine | alanine | asparagine | leucine | glutamic acid |
| proline | Isoleucine | tyrosine | Alanine | serine | asparagine | leucine | glutamic acid |
| proline | Isoleucine | glutamine | Tryptophan | glycine | asparagine | leucine | glutamic acid |
| proline | Isoleucine | threonine | Tryptophan | aspartic acid | asparagine | leucine | glutamic acid |
| proline | Isoleucine | arginine | Tryptophan | proline | asparagine | leucine | glutamic acid |
| proline | Isoleucine | alanine | Tyrosine | glycine | asparagine | leucine | glutamic acid |
| proline | Isoleucine | asparagine | Tryptophan | proline | asparagine | leucine | glutamic acid |
| proline | Isoleucine | serine | Glutamine | serine | cysteine | glycine | tryptophan |
| proline | Isoleucine | serine | Glutamine | serine | cysteine | alanine | proline | where Xaa$_4$ is selected from the group consisting of: glutamine, tyrosine, tryptophan, alanine and phenylalanine;

where Xaa$_5$ is selected from the group consisting of: serine, glycine, proline, alanine and aspartic acid;

(e) Light Chain CDR 2 has an amino acid sequence having the formula of:

Ala-Ala-Ser-Xaa$_6$-Xaa$_7$-Xaa$_8$-Ser (SEQ ID NO: 14)

where Xaa$_6$ is selected from the group consisting of: asparagine and cysteine;

where Xaa$_7$ is selected from the group consisting of: leucine, glycine and alanine;

where Xaa$_8$ is selected from the group consisting of glutamic acid, tryptophan and proline; and (f) Light Chain CDR 3 has an amino acid sequence of: Gln-Gln-Ser-Asn-Glu-Asp-Pro-Phe-Thr (SEQ ID NO:11), where the heavy chain CDR 2 has an amino acid sequence other than Trp-Ile-Asn-Thr-His-Thr-Gly-Glu-Pro-Ile-Tyr-Ala-Asp-Asp-Phe-Lys-Gly (SEQ ID NO:7) when the light chain CDR 1 has the amino acid sequence of Lys-Ala-Ser-Gln-Ser-Val-Asp-Tyr-Asn-Gly-Asp-Ser-Tyr-Leu-Asn (SEQ ID NO:9) and the light chain CDR 2 has the amino acid sequence of Ala-Ala-Ser-Asn-Leu-Glu-Ser (SEQ ID NO: 10), the light chain CDR 1 has an amino acid sequence other than Lys-Ala-Ser-Gln-Ser-Val-Asp-Tyr-Asn-Gly-Asp-Ser-Tyr-Leu-Asn (SEQ ID NO:9) when the heavy chain CDR 2 has the amino acid sequence Trp-Ile-Asn-Thr-His-Thr-Gly-Glu-Pro-Ile-Tyr-Ala-Asp-Asp-Phe-Lys-Gly (SEQ ID NO:7) and the light chain CDR 2 has the amino acid sequence Ala-Ala-Ser-Asn-Leu-Glu-Ser (SEQ ID NO: 10), or the light chain CDR 2 has an amino acid sequence other than Ala-Ala-Ser-Asn-Leu-Glu-Ser (SEQ ID NO: 10) when the heavy chain CDR 2 has the amino acid sequence of Trp-Ile-Asn-Thr-His-Thr-Gly-Glu-Pro-Ile-Tyr-Ala-Asp-Asp-Phe-Lys-Gly (SEQ ID NO:7) and the light chain CDR 1 has the amino

III. Nucleic Acid Molecules

The present invention provides for a nucleic acid molecule, generally isolated, encoding an antibody of the present invention that immunospecifically binds to hBNP or hBNP fragment. In one aspect, the invention provides an isolated nucleic acid molecule encoding an antibody that binds to an epitope comprising amino acid residues 5 through 13 of hBNP or hBNP fragment thereof with at least about a two fold improvement, at least about a three fold improvement, at least about a five fold improvement, at least about a ten fold improvement, at least about a fifteen fold improvement, at least about a twenty fold improvement, at least about a twenty-five fold improvement, at least about a thirty fold improvement, at least about a thirty-five fold improvement, at least about a forty fold improvement, at least about a forty-five fold improvement, at least about a fifty fold improvement, at least about a fifty-five fold improvement, at least about a sixty fold improvement, at least about a seventy fold improvement or at least about a seventy-five fold improvement in its equilibrium dissociation constant ($K_D$) when compared with an antibody produced by hybridoma cell line 106.3, said cell line having A.T.C.C. Accession No. HB-12044. The present invention also provides an isolated nucleic acid molecule that comprises a nucleotide sequence that hybridizes, under stringent conditions, to the nucleic acid molecule described herein that encodes an antibody that binds to an epitope comprising amino acid residues 5 through 13 of hBNP or hBNP fragment with at least about a two fold improvement, at least about a three fold improvement, at least about a five fold improvement, at least about a ten fold improvement, at least about a fifteen fold improvement, at least about a twenty fold improvement, at least about a twenty-five fold improvement, at least about a thirty fold improvement, at least about a thirty-five fold improvement, at least about a forty fold improvement, at least about a forty-five fold improvement, at least about a fifty fold improvement, at least about a fifty-five fold improvement, at least about a sixty fold improvement, at least about a seventy fold improvement or at least about a seventy-five fold improvement in its equilibrium dissociation constant ($K_D$) when compared with an antibody produced by hybridoma cell line 106.3, said cell line having A.T.C.C. Accession No. HB-12044.

In another aspect, the invention provides an isolated nucleic acid molecule encoding an antibody that immunospecifically binds to hBNP or hBNP fragment and that has a $K_D$ of at least $2.0 \times 10^{-11}$ M, of at least $3.0 \times 10^{-11}$ M, of at least $4.0 \times 10^{-11}$ M, of at least $4.2 \times 10^{-11}$ M, of at least $1.0 \times 10^{-12}$ M of at least $1.0 \times 10^{-13}$ M, of at least $7.4 \times 10^{-13}$ M, of at least $8.0 \times 10^{-13}$ M, of at least $1.0 \times 10^{-14}$ M, of at least $1.0 \times 10^{-15}$ M, or has a $K_D$ ranging from $2.0 \times 10^{-11}$ M to $1.0 \times 10^{-15}$ M, from $3.0 \times 10^{-11}$ M to $1.0 \times 10^{-14}$ M, from $4.0 \times 10^{-11}$ M to $8.0 \times 10^{-13}$ M or from $4.2 \times 10^{-11}$ M to $7.4 \times 10^{-13}$ M. The present invention also provides an isolated nucleic acid molecule that comprises a nucleotide sequence that hybridizes, under stringent conditions, to the nucleic acid molecule described herein that encodes an antibody that immunospecifically binds to hBNP or hBNP fragment and that has a $K_D$ of at least $2.0 \times 10^{-11}$ M, of at least $3.0 \times 10^{-11}$ M, of at least $4.0 \times 10^{-11}$ M, of at least $4.2 \times 10^{-11}$ M, of at least $1.0 \times 10^{-12}$ M of at least $1.0 \times 10^{-13}$ M, of at least $7.4 \times 10^{-13}$ M, of at least $8.0 \times 10^{-13}$ M, of at least $1.0 \times 10^{-14}$ M, of at least $1.0 \times 10^{-15}$ M, or has a $K_D$ ranging from $2.0 \times 10^{-11}$ M to $1.0 \times 10^{-15}$ M, from $3.0 \times 10^{-11}$ M to $1.0 \times 10^{-14}$ M, from $4.0 \times 10^{-11}$ M to $8.0 \times 10^{-13}$ M or from $4.2 \times 10^{-11}$ M to $7.4 \times 10^{-13}$ M.

In another aspect, an isolated nucleic acid molecule encodes an antibody that immunospecifically binds to amino acid residues 5 through 13 of human BNP or hBNP fragment at a $K_D$ of at least $2.0 \times 10^{-11}$ M, of at least $3.0 \times 10^{-11}$ M, of at least $4.0 \times 10^{-11}$ M, of at least $4.2 \times 10^{-11}$ M, of at least $1.0 \times 10^{-12}$ M of at least $1.0 \times 10^{-13}$ M, of at least $7.4 \times 10^{-13}$ M, of at least $8.0 \times 10^{-13}$ M, of at least $1.0 \times 10^{-14}$ M, of at least $1.0 \times 10^{-15}$ M, or has a $K_D$ ranging from $2.0 \times 10^{-11}$ M to $1.0 \times 10^{-15}$ M, from $3.0 \times 10^{-11}$ M to $1.0 \times 10^{-14}$ M, from $4.0 \times 10^{-11}$ M to $8.0 \times 10^{-13}$ M or from $4.2 \times 10^{-11}$ M to $7.4 \times 10^{-13}$ M. The present invention also provides an isolated nucleic acid molecule that comprises a nucleotide sequence that hybridizes, under stringent conditions, to the nucleic acid molecule described herein that encodes an antibody that immunospecifically binds to amino acid residues 5 through 13 of hBNP or hBNP fragment at a $K_D$ of at least $2.0 \times 10^{-11}$ M, of at least $3.0 \times 10^{-11}$ M, of at least $4.0 \times 10^{-11}$ M, of at least $4.2 \times 10^{-11}$ M, of at least $1.0 \times 10^{-12}$ M of at least $1.0 \times 10^{-13}$ M, of at least $7.4 \times 10^{-13}$ M, of at least $8.0 \times 10^{-13}$ M, of at least $1.0 \times 10^{-14}$ M, of at least $1.0 \times 10^{-15}$ M, or has a $K_D$ ranging from $2.0 \times 10^{-11}$ M to $1.0 \times 10^{-15}$ M, from $3.0 \times 10^{-11}$ M to $1.0 \times 10^{-14}$ M, from $4.0 \times 10^{-11}$ M to $8.0 \times 10^{-13}$ M or from $4.2 \times 10^{-11}$ M to $7.4 \times 10^{-13}$ M.

In yet another aspect, the invention provides an isolated nucleic acid molecule encoding an antibody that immunospecifically binds to amino acid residues 5 through 13 of hBNP or hBNP fragment at a $K_D$ of from $4.2 \times 10^{-11}$ M to $7.4 \times 10^{-13}$ M, wherein said nucleic acid molecule comprises the nucleotide sequence of antibody produced by CHO cell line AM1. The present invention also provides an isolated nucleic acid molecule that comprises a nucleotide sequence that hybridizes, under stringent conditions, to the nucleic acid molecule described herein that encodes an antibody that immunospecifically binds to amino acid residues 5 through 13 of hBNP or hBNP fragment at a $K_D$ of from $4.2 \times 10^{-11}$ M to $7.4 \times 10^{-13}$ M, wherein said nucleic acid molecule comprises the nucleotide sequence of antibody produced by CHO cell line AM1.

In another aspect, the present invention provides an isolated nucleic acid molecule that encodes antibodies that immunospecifically bind to hBNP or hBNP fragment, wherein said antibodies comprise derivatives or variants of antibodies produced by hybridoma cell line 106.3 (ATCC Accession No. HB-12044). As discussed previously herein, the inventors of the present invention have discovered that antibodies that are derivatives or variants of the antibodies produced by hybridoma cell line 106.3 can be produced which exhibit a high binding affinity, specifically a $k_{on}$ (or $k_a$) of at least about $2.4 \times 10^4$ $M^{-1}s^{-1}$, of at least about $2.5 \times 10^4$ $M^{-1}s^{-1}$, of at least about $3.3 \times 10^4$ $M^{-1}s^{-1}$, of at least about $5.0 \times 10^4$ $M^{-1}s^{-1}$, of at least about $1.25 \times 10^7$ $M^{-1}s^{-1}$ of at least about $1.35 \times 10^7$ $M^{-1}s^{-1}$, of at least about $1.0 \times 10^8$ $M^{-1}s^{-1}$, of at least about $1.0 \times 10^9$ $M^{-1}s^{-1}$, or have a $k_{on}$ (or $k_a$) ranging from $5.0 \times 10^4$ $M^{-1}s^{-1}$ to $1.0 \times 10^8$ $M^{-1}s^{-1}$, from $3.3 \times 10^4$ $M^{-1}s^{-1}$ to $1.0 \times 10^9$ $M^{-1}s^{-1}$, from $2.5 \times 10^4$ $M^{-1}s^{-1}$ to $1.25 \times 10^7$ $M^{-1}s^{-1}$, from $2.4 \times 10^{-11}$ $M^{-1}s^{-1}$ to $1.35 \times 10^7$ $M^{-1}s^{-1}$, a $k_{off}$ (or $k_d$) of at least about $1.0 \times 10^{-3}$ $s^{-1}$, of at least about $1.0 \times 10^{-4}$ $s^{-1}$, of at least about $1.0 \times 10^{-5}$ $s^{-1}$, of at least about $1.0 \times 10^{-6}$ $s^{-1}$ or have a $k_{off}$ (or $k_d$) ranging from $1.0 \times 10^{-3}$ $s^{-1}$ to $1.0 \times 10^{-6}$ $s^{-1}$, from $1.0 \times 10^{-3}$ $s^{-1}$ to $1.0 \times 10^{-5}$ $s^{-1}$ or from $1.0 \times 10^{-3}$ $s^{-1}$ to $1.0 \times 10^{-4}$ $s^{-1}$ and a $K_D$ of at least about $2.0 \times 10^{-11}$ M, of at least about $3.0 \times 10^{-11}$ M, of at least about $4.0 \times 10^{-11}$ M, of at least about $4.2 \times 10^{-11}$ M, of at least about $1.0 \times 10^{-12}$ M of at least about $1.0 \times 10^{-13}$ M, of at least about $7.4 \times 10^{-13}$ M, of at least about $8.0 \times 10^{-13}$ M, of at least about $1.0 \times 10^{-14}$ M, of at least about $1.0 \times 10^{-15}$ M of at least about $1.0 \times 10^{-16}$ M, or have a $K_D$ ranging from $2.0 \times 10^{-11}$ M to $1.0 \times 10^{-16}$ M, from $2.0 \times 10^{-11}$ M to $1.0 \times 10^{-5}$ M, from $3.0 \times 10^{-11}$ M to $1 \times 10^{-14}$ M, from $4.0 \times 10^{-11}$ M to $8.0 \times 10^{-13}$ M or from $4.2 \times 10^{-11}$ M to $7.4 \times 10^{-13}$ M. The derived or variant antibodies of the present invention comprises at least one mutation (such as deletions, additions and/or substitutions) in at least one of the heavy chain complementary determining ("CDR") regions (for example, the heavy chain CDR 1, heavy chain CDR 2, or heavy chain CDR 3), at least one mutation (such as deletions, additions and/or substitutions) in the light chain CDR regions (for example, the light chain CDR 1, light chain CDR 2, or light chain CDR 3) when compared to the amino acid sequence the antibody produced by hybridoma cell line 106.3. Standard techniques known to those of skill in the art can be used to introduce mutations (such as deletions, additions, and/or substitutions) in the nucleic acid molecule encoding an antibody of the present invention, including, for example, site-directed mutagenesis and PCR-mediated mutagenesis which results in amino acid substitutions. In one aspect, the derivatives include less than 10 amino acid substitutions, less than 5 amino acid substitutions, less than 4 amino acid substitutions, less than 3 amino acid substitutions, or less than 2 amino acid substitutions relative to the original antibody produced by hybridoma cell line 106.3. In one aspect, the derivatives have conservative amino acid substitutions are made at one or more predicted non-essential amino acid residues (i.e., amino acid residues which are not critical for the antibody to immunospecifically bind to hBNP or hBNP fragment). A "conservative amino acid substitution" is one in which the amino acid residue is replaced with the amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), betabranched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that exhibit enhanced binding affinity to hBNP or hBNP fragment. Following mutagenesis, the encoded antibody can be expressed and the activity of the antibody can be determined.

In another aspect, the present invention provides an isolated nucleic acid molecule encoding an antibody that immunospecifically binds to hBNP or hBNP fragment, said antibody having a heavy chain CDR 2 having an amino acid sequence of the formula of:

```
                                            (SEQ ID NO: 12)
Trp-Ile-Asn-Thr-His-Thr-Gly-Glu-Xaa₁-Xaa₂-Tyr-Ala-

Asp-Asp-Phe-Lys-Gly
``` where $Xaa_1$ is selected from the group consisting of proline and alanine and $Xaa_2$ is selected from the group consisting of isoleucine and tyrosine, provided that when $Xaa_1$ is proline, $Xaa_2$ is not isoleucine. The present invention also provides an isolated nucleic acid molecule that comprises a nucleotide sequence that hybridizes, under stringent conditions, to the nucleic acid molecule described herein that encodes an antibody having a heavy chain CDR 2 having an amino acid sequence of the above-described formula.

In another aspect, the invention provides an isolated nucleic acid molecule encoding an antibody that immunospecifically binds to hBNP or hBNP fragment, said antibody comprising (alternatively, consisting of) a heavy chain CDR 2 having an amino acid sequence of SEQ ID NO: 15. The present invention also provides an isolated nucleic acid molecule that comprises a nucleotide sequence that hybridizes, under stringent conditions, to the nucleic acid molecule described herein that encodes an antibody comprising a heavy chain CDR 2 having the amino acid sequence of SEQ ID NO: 15.

In another aspect, the present invention provides an isolated nucleic acid molecule encoding an antibody that immunospecifically binds to hBNP or hBNP fragment, said antibody having a light chain CDR 1 that has an amino acid sequence having a formula of:

```
                                            (SEQ ID NO: 13)
Lys-Ala-Xaa₃-Xaa₄-Xaa₅-Val-Asp-Tyr-Asn-Gly-Asp-

Ser-Tyr-Leu-Asn
``` where $Xaa_3$ is selected from the group consisting of: serine, alanine, asparagine, glutamine, tyrosine, threonine and arginine; where $Xaa_4$ is selected from the group consisting of: glutamine, tyrosine, tryptophan, alanine and phenylalanine and where $Xaa_5$ is selected from the group consisting of: serine, glycine, proline, alanine and aspartic acid, provided that $Xaa_3$ is not serine when $Xaa_4$ is glutamine and $Xaa_5$ is serine. The present invention also provides an isolated nucleic acid molecule that comprises a nucleotide sequence that hybridizes, under stringent conditions, to the nucleic acid molecule described herein that encodes an antibody having a light chain CDR 1 having an amino acid sequence of the above-described formula.

In another aspect, the invention provides an isolated nucleic acid molecule encoding an antibody that immunospecifically binds to hBNP or hBNP fragment, said antibody comprising (alternatively, consisting of) a light chain CDR 1 having an amino acid sequence of SEQ ID NO:16, SEQ ID NO: 17, SEQ ID NO:18, SEQ ID NO:19, SEQ ID NO:20, SEQ ID NO:21 or SEQ ID NO:22. The present invention also provides an isolated nucleic acid molecule that comprises a nucleotide sequence that hybridizes, under stringent conditions, to the nucleic acid molecule described herein that encodes an antibody comprising a light chain CDR 1 having the amino acid sequence of SEQ ID NO:16, SEQ ID NO: 17, SEQ ID NO:18, SEQ ID NO:19, SEQ ID NO:20, SEQ ID NO:21 or SEQ ID NO:22.

In another aspect, the present invention provides an isolated nucleic acid molecule encoding an antibody that immunospecifically binds to hBNP or hBNP fragment, said antibody having a light chain CDR 2 that has an amino acid sequence having a formula of:

```
Ala-Ala-Ser-Xaa₆-Xaa₇-Xaa₈-Ser    (SEQ ID NO: 14)
``` where $Xaa_6$ is selected from the group consisting of: asparagine and cysteine, where $Xaa_7$ is selected from the group consisting of: leucine, glycine and alanine and where $Xaa_8$ is selected from the group consisting of glutamic acid, tryptophan and proline, provided that $Xaa_6$ is not asparagine when $Xaa_7$ is leucine and $Xaa_8$ is glutamic acid. The present invention also provides an isolated nucleic acid molecule that comprises a nucleotide sequence that hybridizes, under stringent conditions, to the nucleic acid molecule described herein that encodes an antibody having a light chain CDR 2 having an amino acid sequence of the above-described formula.

In another aspect, the invention provides an isolated nucleic acid molecule encoding an antibody that immunospecifically binds to hBNP or hBNP fragment, said antibody comprising (alternatively, consisting of) a light chain CDR 2 having an amino acid sequence of SEQ ID NO:23 or SEQ ID NO:24. The present invention also provides an isolated nucleic acid molecule that comprises a nucleotide sequence that hybridizes, under stringent conditions, to the nucleic acid molecule described herein that encodes an antibody comprising a light chain CDR 2 having the amino acid sequence of SEQ ID NO:23 or SEQ ID NO:24.

In another aspect, the invention provides an isolated nucleic acid molecule that encodes an antibody that immunospecifically binds to hBNP or hBNP fragment, said antibody comprising (alternatively, consisting) a heavy chain CDR 2 having an amino acid sequence of SEQ ID NO: 15, a light chain CDR 1 having an amino acid sequence of SEQ ID NO:16, SEQ ID NO: 17, SEQ ID NO:18, SEQ ID NO:19, SEQ ID NO:20, SEQ ID NO:21 or SEQ ID NO:22, a light chain CDR 2 having an amino acid sequence of SEQ ID NO:23 or SEQ ID NO:24 or any combinations these amino acid sequences. The present invention also provides an isolated nucleic acid molecule that comprises a nucleotide sequence that hybridizes, under stringent conditions, to the nucleic acid molecule described herein that encodes an antibody comprising a heavy chain CDR 2 having an amino acid sequence of SEQ ID NO: 15, a light chain CDR 1 having an amino acid sequence of SEQ ID NO:16, SEQ ID NO: 17, SEQ ID NO:18, SEQ ID NO:19, SEQ ID NO:20, SEQ ID NO:21 or SEQ ID NO:22, a light chain CDR 2 having an amino acid sequence of SEQ ID NO:23 or SEQ ID NO:24 or any combinations these amino acid sequences.

In another aspect, the present invention provides an isolated nucleic acid molecule encoding an antibody that immunospecifically binds to hBNP or hBNP fragment, said antibody having a heavy chain CDR 1, heavy chain CDR 2, heavy chain CDR 3, a light chain CDR 1, a light chain CDR 2 and a light variable CDR 3 comprising the following amino acid sequences:

(a) Heavy Chain CDR 1 having an amino acid sequence of: Gly-Tyr-Thr-Phe-Thr-His-Tyr-Gly-Ile-Asn (SEQ ID NO:6);

(b) Heavy Chain CDR 2 having an amino acid sequence having a formula of:

(SEQ ID NO: 12)
Trp-Ile-Asn-Thr-His-Thr-Gly-Glu-Xaa$_1$-Xaa$_2$-Tyr-Ala-

Asp-Asp-Phe-Lys-Gly where Xaa$_1$ is selected from the group consisting of proline and alanine;

where Xaa$_2$ is selected from the group consisting of isoleucine and tyrosine;

(c) Heavy Chain CDR 3 having an amino acid sequence of: Ser-His-Arg-Phe-Gly-Leu-Asp-Tyr (SEQ ID NO:8);

(d) Light Chain CDR 1 having an amino acid sequence having a formula of:

(SEQ ID NO: 13)
Lys-Ala-Xaa$_3$-Xaa$_4$-Xaa$_5$-Val-Asp-Tyr-Asn-Gly-Asp-

Ser-Tyr-Leu-Asn where Xaa$_3$ is selected from the group consisting of: serine, alanine, asparagine, glutamine, tyrosine, threonine and arginine;

where Xaa$_4$ is selected from the group consisting of: glutamine, tyrosine, tryptophan, alanine and phenylalanine;

where Xaa$_5$ is selected from the group consisting of: serine, glycine, proline, alanine and aspartic acid;

(e) Light Chain CDR 2 has an amino acid sequence having the formula of:

Ala-Ala-Ser-Xaa$_6$-Xaa$_7$-Xaa$_8$-Ser (SEQ ID NO: 14)

where Xaa$_6$ is selected from the group consisting of: asparagine and cysteine;

where Xaa$_7$ is selected from the group consisting of: leucine, glycine and alanine;

where Xaa$_8$ is selected from the group consisting of glutamic acid, tryptophan and proline; and (f) Light Chain CDR 3 has an amino acid sequence of: Gln-Gln-Ser-Asn-Glu-Asp-Pro-Phe-Thr (SEQ ID NO:11), where the heavy chain CDR 2 has an amino acid sequence other than Trp-Ile-Asn-Thr-His-Thr-Gly-Glu-Pro-Ile-Tyr-Ala-Asp-Asp-Phe-Lys-Gly (SEQ ID NO:7) when the light chain CDR 1 has the amino acid sequence of Lys-Ala-Ser-Gln-Ser-Val-Asp-Tyr-Asn-Gly-Asp-Ser-Tyr-Leu-Asn (SEQ ID NO:9) and the light chain CDR 2 has the amino acid sequence of Ala-Ala-Ser-Asn-Leu-Glu-Ser (SEQ ID NO: 10), the light chain CDR 1 has an amino acid sequence other than Lys-Ala-Ser-Gln-Ser-Val-Asp-Tyr-Asn-Gly-Asp-Ser-Tyr-Leu-Asn (SEQ ID NO:9) when the heavy chain CDR 2 has the amino acid sequence Trp-Ile-Asn-Thr-His-Thr-Gly-Glu-Pro-Ile-Tyr-Ala-Asp-Asp-Phe-Lys-Gly (SEQ ID NO:7) and the light chain CDR 2 has the amino acid sequence Ala-Ala-Ser-Asn-Leu-Glu-Ser (SEQ ID NO: 10), or the light chain CDR 2 has an amino acid sequence other than Ala-Ala-Ser-Asn-Leu-Glu-Ser (SEQ ID NO: 10) when the heavy chain CDR 2 has the amino acid sequence of Trp-Ile-Asn-Thr-His-Thr-Gly-Glu-Pro-Ile-Tyr-Ala-Asp-Asp-Phe-Lys-Gly (SEQ ID NO:7) and the light chain CDR 1 has the amino acid sequence of Lys-Ala-Ser-Gln-Ser-Val-Asp-Tyr-Asn-Gly-Asp-Ser-Tyr-Leu-Asn (SEQ ID NO:9). The present invention also provides an isolated nucleic acid molecule that comprises a nucleotide sequence that hybridizes, under stringent conditions, to the nucleic acid molecule described herein that encodes an antibody having a heavy chain CDR 1 region, a heavy chain CDR 2 region, a heavy chain CDR 3 region, a light chain CDR 1 region, a light chain CDR 2 region and a light chain CDR 3 region having the amino acid sequences pursuant to the above-described formula.

In yet another aspect, the present invention provides an isolated nucleic acid molecule encoding an antibody that immunospecifically binds to hBNP or hBNP fragment, wherein said antibody is produced by CHO cell line AM1. The present invention also provides an isolated nucleic acid molecule that comprises a nucleotide sequence that hybridizes, under stringent conditions, to the nucleic acid molecule that encodes an antibody that immunospecifically binds to hBNP or hBNP fragment, wherein said antibody is produced by CHO cell line AM1.

IV. Methods for Preparing the Antibodies of the Present Invention

The antibodies of the present invention can be prepared using routine techniques known to those skilled in the art.

In one aspect, the antibodies of the present invention can be prepared by recombinant expression of immunoglobulin light and heavy chain genes in a host cell. To express an antibody recombinantly, a host cell is transfected with one or more recombinant expression vectors carrying nucleic acid molecules encoding the immunoglobulin light and heavy chains of the antibody such that the light and heavy chains are expressed in the host cell and, preferably, secreted into the medium in which the host cells are cultures, from which medium the antibodies can be recovered. Standard recombinant nucleic acid (DNA) methodologies are used to obtain antibody heavy and light chain genes, incorporate these genes into recombinant expressions vectors and introduce the vectors into host cells, such as those described in Sambrook, Fritsch and Maniatis (eds), *Molecular Cloning: A Laboratory Manual, Second Edition*, Cold Spring Harbor, New Your, (1989), Ausubel, F. M. et al. (eds.) *Current Protocols in Molecular Biology*, Greene Publishing Associates (1989) and in U.S. Pat. No. 4,816,397 by Boss et al.

To express the antibodies of the invention, nucleic acid molecules encoding the light and heavy chain regions are first obtained. These nucleic acid molecules may be obtained from the hybridoma cell line expressing monoclonal antibody 106.3 and modified by means well known in the art (such as site-directed mutagenesis) to generate antibodies of the present invention, including, for example, the antibodies produced by CHO cell line AM1. A hybridoma cell line expressing monoclonal antibody 106.3 was deposited with the American Type Culture Collection ("ATCC"), University Boulevard, Manassas, Va. 20110 and was accorded accession number HB-12044. The nucleic acid sequence of monoclonal antibody 106.3 is shown in FIGS. 3A-3E and SEQ ID NO: 1.

For example, once the 106.3 variable heavy (VH) and variable (VL) nucleic acid fragments are obtained, these sequences or specific regions within these sequences, such as the complementary determining ("CDR") regions, can be mutated to encode the AM1 or AM1-related amino acid sequences disclosed herein. The amino acid sequences encoded by the 106.3 VH and VL DNA sequences are compared to the AM1 or AM1-related VH and VL amino acid sequences to identify amino acid residues in the AM1 or AM1-related sequence that differ. The appropriate nucleotides of monoclonal antibody 106.3 are mutated such that the mutated sequence encodes the AM1 or AM1-related amino acid sequence, using the genetic code to determine which nucleotide changes should be made. Mutagenesis of antibody 106.3 sequences can be carried out by standard methods, such as PCR-mediated mutagenesis (in which the mutated nucleotides are incorporated into the PCR primers such that the PCR product contains the mutations) or site-directed mutagenesis.

Alternatively, in another aspect, nucleic acid molecules encoding the VH and VL chains can be synthesized on a chemical synthesizer, using routine techniques known to those in the art. For example, the VH and VL chains from the nucleic acid molecules described in Section III can be chemically synthesized using routine techniques known in the art. Starting at the 3' terminal base which is attached to a support, nucleotides are coupled in a step-wise fashion. Following the addition of the most 5' nucleotide, the nucleotide is cleaved from the solid support and purified by desalting followed by polyacrylamide gel electrophoresis (PAGE) (Midland Certified Reagents, Midland, Tex., www.oligos.com).

Once nucleic acid fragments encoding AM1 or AM1-related VH and VL segments are obtained (by amplification and mutagenesis of VH and VL genes, as described above), these nucleic acid fragments can be further manipulated by standard recombinant DNA techniques, for example to convert the variable region genes to an antibody (such as, but not limited to, a full-length antibody chain genes, to Fab fragment genes or to a scFv gene). In these manipulations, a VL- or VH-encoding nucleic acid fragment is operatively linked to another nucleic acid fragment encoding another protein, such as antibody constant region or a flexible linker. The term "operatively linked", as used in this context, is intended to mean that the two nucleic acid fragments are joined such that the amino acid sequences encoded by the two nucleic acid fragments remain in-frame.

In an alternative method, an scFv gene may be constructed with wildtype CDR regions (such as those of monoclonal antibody 106.3) and then mutated using techniques known in the art.

The isolated nucleic acid molecule encoding the VH region can be converted to a full-length heavy chain gene by operatively linking the VH-encoding nucleic acid molecule to another nucleic acid molecule encoding heavy chain constant regions (CH1, CH2 and CH3). The sequences of human heavy chain constant region genes are known in the art (See for example, Kabat, E. A., et al., *Sequences of Proteins of Immunological Interest, Fifth Edition*, U.S. Department of Health and Human Services, NIH Publication No. 91-3242 (1991)). In another aspect, the present invention further encompasses all known human heavy chain constant regions, including but not limited to, all known allotypes of the human heavy chain constant region. Nucleic acid fragments encompassing these regions can be obtained by standard PCR amplification. The heavy chain constant region can be an IgG1, IgG2, IgG3, IgG4, IgA, IgE, IgM or IgD constant region.

The isolated nucleic acid molecule encoding the VL region can be converted to a full-length light chain gene (as well as a Fab light chain gene) by operatively linking the VL-encoding nucleic acid molecule to another nucleic acid molecule encoding the light chain constant region, CL. The sequences of human light chain constant region genes are known in the art (see e.g., Kabat, E. A., et al., *Sequences of Proteins of Immunological Interest, Fifth Edition*, U.S. Department of Health and Human Services, NIH Publication No. 91-3242 (1991)). The present invention encompasses all known human light chain constant regions, including but not limited to, all known allotypes of the human light chain constant region. Nucleic acid fragments encompassing these regions can be obtained by standard PCR amplification. The light chain constant region can be a kappa or lambda constant region, but most preferably is a kappa constant region.

It is to be understood that the specific designations of framework (FR) and CDR regions within a particular heavy or light chain region may vary depending on the convention or numbering system used to identify such regions (e.g. Chothia, Kabat, Oxford Molecular's *AbM* modeling software, all of which are known to those of ordinary skill in the art). For the purposes of the present invention, the Kabat numbering system is used.

To create a scFv gene, the VH- and VL-encoding nucleic acid fragments are operatively linked to another fragment encoding a flexible linker, such as, a linker that is encoded by the amino acid sequence GPAKELTPLKEAKVS (SEQ ID NO:4). Examples of other linker sequences that can be used in the present invention can be found in Bird et al., *Science* 242:423-426 (1988), Huston et al., *Proc. Natl. Acad. Sci. USA* 85:5879-5883 (1988) and McCafferty et al., *Nature,* 348:552-554 (1990).

To express the antibodies, or antibody portions of the invention, nucleic acid molecules encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods (for example, ligation of complementary restriction sites on the antibody gene fragment and vector, or blunt end ligation if no restriction sites are present). Prior to the insertion of the light or heavy chain sequences, the expression vector may already carry antibody constant region sequences. For example, one approach to converting the VH and VL sequences to full-length antibody genes is to insert them into expression vectors already encoding heavy chain constant and light chain constant regions, respectively, such that the VH segment is operatively linked to the CH "segment" within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The single peptide can be an immunoglobin signal peptide or a heterologous signal peptide (i.e., a signal peptide from a non-immunoglobulin protein).

In addition to the antibody chain genes, the recombinant expression vectors can carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology. Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of the expression of protein desired, etc. Preferred regulatory sequences for mammalian host cell expression include viral elements that direct high levels of protein expression in mammalian cells, such as promoters and/or enhancers derived from cytomegalovirus ("CMV") (such as the CMV promoter/enhancer), Simian Virus 40 ("SV40") (such as the SV40 promoter/enhancer), adenovirus, (such as the adenovirus major late promoter ("AdMLP")) and polyoma. For further description of viral regulatory elements, and sequences thereof, see for example, U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, recombinant expression vectors may carry additional sequences, such as sequences that regulate replication of the vector in host cells (e.g., origins of replication) and selectable marker genes. The selectable marker gene facilitates selection of host cells into which the vector has been introduced (See, for example, U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase ("DHFR") gene for use in dhfr-host cells with methotrexate selection/amplification and the neomycin ("neo") gene for G418 selection.

For expression of the light and heavy chains, the expression vector(s) encoding the heavy and light chains are transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (See, Boss, M. A. and Wood, C. R., *Immunology Today* 6:12-13 (1985)).

Preferred mammalian host cells for expressing the recombinant antibodies of the invention include the Chinese Hamster Ovary ("CHO") cells (including dhfr-CHO cells, described in Urlaub and Chasin, *Proc. Natl. Acad. Sci. USA* 77:4216-4220 (1980), used with a DHFR selectable marker, for example, as described in R. J. Kaufman and P. A. Sharp, *Mol. Biol.* 159:601-621 (1982)), NSO myeloma cells, COS cells, HEK-293 cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments, F(ab')$_2$ fragments or scFv molecules. It will be understood that variations on the above procedure are within the scope of the present invention. For example, it may be desirable to transfect a host cell with nucleic acid molecule encoding either the light chain or the heavy chain (but not both) of an antibody of the present invention. Recombinant DNA technology may also be used to remove some or all of the nucleic acid molecules encoding either or both of the light and heavy chains that are not necessary for binding to hBNP or hBNP fragment. The molecules expressed from such truncated nucleic acid molecules also are encompassed by the antibodies of the invention.

In a preferred system for recombinant expression of an antibody, or antigen binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector. Cells were cultured in medium without hypoxanthine and thymidine to obtain those CHO cells that have acquired the DHFR gene from the transfecting vector. Antigen specific screening methods were used to identify those clones that expressed the highest quantity of antibody. Those individual clones were expanded and were routinely re-screened. The highest producing clone was AM1. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In view of forgoing, another aspect of the invention pertains to nucleic acid, vector and host cell compositions that can be used for recombinant expression of the antibodies and antibody portions of the invention. The amino acid sequence encoding the heavy chain CDR 2 region of AM1 and variants thereof is shown in SEQ ID NO: 15. The amino acid sequence encoding the AM1 light chain CDR 1 region is shown in SEQ ID NO:22. The nucleic acid molecule encoding the heavy chain CDR 2 region of AM1 is shown in SEQ ID NO:81. The nucleic acid molecule encoding the light chain CDR 1 region of AM1 is shown in SEQ ID NO:82.

V. Selection of Recombinant Antibodies

The antibodies of the present invention, including the AM1 or AM1-related antibodies disclosed herein, can be isolated by screening of a combinatorial antibody library. Preferably, the combinatorial antibody library is a recombinant combinatorial library, preferably a scFv yeast display library, prepared using chimeric, humanized or human VL and VH cDNAs. Methodologies for preparing and screening such libraries are known in the art. In addition to commercially available vectors for generating yeast display libraries (such as, the pYD1 vector, Invitrogen, Carlsbad, Calif.) examples of methods and reagents particularly amenable for use in generating and screening antibody display libraries can be found in, for example, Boder E. T. and Wittrup K. D., Yeast surface display for directed evolution of protein expression, affinity, and stability, *Methods Enzymol.*, 328:430-44 (2000) and Boder E. T. and Wittrup K. D., Yeast surface display for screening combinatorial polypeptide libraries, *Nat. Biotechnol.* 15(6):553-7 (June 1997).

In a preferred embodiment, to isolate antibodies with high binding affinity, such as any of the antibodies described in Section II herein, an antibody that is known to immunospecifically bind to hBNP or hBNP fragment (such as, for example, monoclonal antibody 106.3) is first used to generate human heavy and light chain sequences expressed as scFvs on the surface of yeast (preferably, *Saccaromyces cerevisiae*). These antibody (Such as monoclonal antibody 106.3) scFvs are analyzed to determine the dissociation rate (namely, the $k_{off}$ or $k_d$) of these antibodies. Such constructs then are screened, preferably using biotinylated cyclic hBNP (1-32c). The dissociation rate data can then be plotted as mean fluorescence units ("MFU") versus time (in seconds). A first order decay equation can be used to fit the data. An example of such a formula that can be used is:

$$y = m1 * \exp(-m2 * M0) + m3$$

where m1 is the maximum fluorescence at time zero (*=time and exp exponential);

where m2 is the off-rate (the formula for determining off-rate is well known to those skilled in the art);

where M0 is time x (x being the time that is being measured); and where m3 is the background being generated from the system.

The dissociation rate data can be used to identify off-rate improved antibodies of the present invention from mutagenic libraries.

Those scFv constructs having an improved dissociation rate are selected for subsequent mutagenesis of the heavy and light chain variable regions to generate CDR mutagenic libraries.

To further increase the binding affinity, the VH and VL segments of the preferred VH/VL pair(s) can be randomly mutated, preferably within the CDR2 region of VH, the CDR1 region and/or CDR2 region of VL in a process analogous to the in vivo somatic mutation process responsible for affinity maturation of antibodies during a natural immune response. This in vitro affinity maturation can be accomplished by replacing a portion of each CDR with a degenerate single-stranded oligonucleotide encoding three amino acids within the CDR being targeted. The replacement of a portion of each CDR with a new randomized sequence (up to 8000 possibilities) can be accomplished by homologous recombination in yeast (see, e.g. Example 1). These randomly mutated VH and VL segments can be analyzed for binding to hBNP or hBNP fragment in the context of an scFv; scFvs exhibiting an improved fluorescence and that (a) bind to an epitope comprising amino acid residues 5 through 13 of hBNP or hBNP fragment thereof with at least about a two fold improvement, at least about a three fold improvement, at least about a five fold improvement, at least about a ten fold improvement, at least about a fifteen fold improvement, at least about a twenty fold improvement, at least about a twenty-five fold improvement, at least about a thirty fold improvement, at least about a thirty-five fold improvement, at least about a forty fold improvement, at least about a forty-five fold improvement, at least about a fifty fold improvement, at least about a fifty-five fold improvement, at least about a sixty fold improvement, at least about a seventy fold improvement or at least about a seventy-five fold improvement in its equilibrium dissociation constant ($K_D$) when compared with an antibody produced by hybridoma cell line 106.3, said cell line having A.T.C.C. Accession No. HB-12044, (b) exhibits a $k_{on}$ (or $k_a$) of at least about $2.4 \times 10^4$ $M^{-1}s^{-1}$, of at least about $2.5 \times 10^4$ $M^{-1}s^{-1}$, of at least about $3.3 \times 10^4$ $M^{-1}s^{-1}$, of at least about $5.0 \times 10^4$ $M^{-1}s^{-1}$, at least about $1.25 \times 10^7$ $M^{-1}s^{-1}$ of at least about $1.35 \times 10^7$ $M^{-1}s^{-1}$, of at least about $1.0 \times 10^8$ $M^{-1}s^{-1}$, of at least about $1.0 \times 10^9$ $M^{-1}s^{-1}$, or have a $k_{on}$ (or $k_a$) ranging from $5.0 \times 10^4$ $M^{-1}s^{-1}$ to $1.0 \times 10^8$ $M^{-1}s^{-1}$, from $3.3 \times 10^4$ $M^{-1}s^{-1}$ to $1.0 \times 10^9$ $M^{-1}s^{-1}$, from $2.5 \times 10^4$ $M^{-1}s^{-1}$ to $1.25 \times 10^7$ $M^{-1}s^{-1}$, from $2.4 \times 10^{-11}$ $M^{-1}s^{-1}$ to $1.35 \times 10^7$ $M^{-1}s^{-1}$, (C) exhibits a $k_{off}$ (or $k_d$) of at least about $1.0 \times 10^{-3}$ $s^{-1}$, of at least about $1.0 \times 10^{-4}$ $s^{-1}$, of at least about $1.0 \times 10^{-5}$ $s^{-1}$, of at least about $1.0 \times 10^{-6}$ $s^{-1}$ or have a $k_{off}$ (or $k_d$) ranging from $1.0 \times 10^{-3}$ $s^{-1}$ to $1.0 \times 10^{-6}$ $s^{-1}$, from $1.0 \times 10^{-3}$ $s^{-1}$ to $1.0 \times 10^{-5}$ $s^{-1}$ or from $1.0 \times 10^{-3}$ $s^{-1}$ to $1.0 \times 10^{-4}$ $s^{-1}$, or (d) exhibit a $K_D$ of at least about $2.0 \times 10^{-11}$ M, of at least about $3.0 \times 10^{-11}$ M, of at least about $4.0 \times 10^{-11}$ M, of at least about $4.2 \times 10^{-11}$ M, of at least about $1.0 \times 10^{-12}$ M, of at least about $1.0 \times 10^{-13}$ M, of at least about $7.4 \times 10^{-13}$ M, of at least about $8.0 \times 10^{-13}$ M, of at least about $1.0 \times 10^{-14}$ M, of at least about $1.0 \times 10^{-15}$ M, or have a $K_D$ ranging from $2.0 \times 10^{-11}$ M to $1.0 \times 10^{-15}$ M, from $3.0 \times 10^{-11}$ M to $1 \times 10^{-14}$ M, from $4.0 \times 10^{-11}$ M to $8.0 \times 10^{-13}$ M or from $4.2 \times 10^{-11}$ M to $7.4 \times 10^{-13}$ M can then be isolated and the CDR mutation identified by sequencing.

Following screening of a recombinant scFv display library, clones having the desired characteristics are selected for conversion. Nucleic acid molecules encoding the selected antibody can be recovered from the display package (e.g., from the yeast expression vector) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in Section IV above.

VI. Immunoassays

In another aspect, the present invention relates to immunoassays that can be used for the qualitative and/or quantitative detection of hBNP or hBNP fragment in a test sample. The immunoassays of the present invention can be conducted using any format known in the art, such as, but not limited to, a sandwich format, a competitive inhibition format (including both forward or reverse competitive inhibition assays) or in a fluorescence polarization format.

In immunoassays for the qualitative detection of hBNP or hBNP fragment in a test sample, at least one antibody that binds to certain epitopes of hBNP or hBNP fragment thereof is contacted with at least one test sample suspected of containing or that is known to contain hBNP or hBNP fragment to form an antibody-hBNP immune complex. The antibodies described in Section II herein can be used in such immunoassays to form such antibody-hBNP immune complexes in at least one test sample. These immune complexes can then detected using routine techniques known to those skilled in the art. For example, the antibody of the present invention can be labeled with a detectable label to detect the presence antibody-hBNP complex. Alternatively, the hBNP or hBNP fragments in the test sample can be labeled with a detectable label and the resulting antibody-hBNP immune complexes detected using routine techniques known to those skilled in the art. Detectable labels and their attachment to antibodies are discussed in more detail infra.

Alternatively, a second antibody that binds to the hBNP or hBNP fragment and that contains a detectable label can be added to the test sample and used to detect the presence of the antibody-hBNP complex. Any detectable label known in the art can be used. Detectable labels and their attachment to antibodies are discussed in more detail infra.

In immunoassays for the quantitative detection of BNP, such as a sandwich type format, at least two antibodies are employed to separate and quantify hBNP or hBNP fragment in a test sample. More specifically, the at least two antibodies bind to certain epitopes of hBNP or hBNP fragment forming an immune complex which is referred to as a "sandwich". Generally, one or more antibodies can be used to capture the hBNP or hBNP fragment in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, it is preferred that both antibodies binding to their epitope are not diminished by the binding of any other antibody in the assay to its respective epitope. In other words, antibodies should be selected so that the one or more first antibodies brought into contact with a test sample suspected of containing hBNP or hBNP fragment do not bind to all or part of an epitope recognized by the second or subsequent antibodies, thereby interfering with the ability of the one or more second detection antibodies to bind to the hBNP or hBNP fragment.

The inventors have discovered that an excellent sandwich immunoassay can be performed using the antibodies of the present invention. More specifically, the antibodies of the present invention can be used as a first antibody in said immunoassay. Preferably, the antibody of the present invention immunospecifically bind to epitopes comprising at least three (3) amino acids of 5-13 of hBNP or hBNP fragment with a $K_D$ of from $4.2 \times 10^{-11}$ M to $7.4 \times 10^{-13}$ M. In addition to the antibodies of the present invention, said immunoassay comprises a second antibody, preferably a monoclonal antibody, that immunospecifically binds to epitopes having an amino acid sequence comprising at least three (3) amino acids of amino acids 27-32 of hBNP. An example of a monoclonal antibody that immunospecifically binds to epitopes having an amino acid sequence containing amino acids 27-32 of hBNP is a monoclonal antibody produced by hybridoma cell line BC203.

In a preferred embodiment, the test sample suspected of containing hBNP or a hBNP fragment can be contacted with at least one first capture antibody (or antibodies) and at least one second detection antibodies either simultaneously or sequentially. In the sandwich assay format, a test sample suspected of containing hBNP or hBNP fragment is first brought into contact with the at least one first capture antibody that specifically binds to a particular epitope under conditions which allow the formation of a first antibody-hBNP complex. If more than one capture antibody is used, a first multiple capture antibody-hBNP complex is formed. In a sandwich assay, the antibodies, preferably, the at least one capture antibody, are used in molar excess amounts of the maximum amount of hBNP or hBNP fragment expected in the test sample. For example, from about 5 µg/mL to about 1 mg/mL of antibody per mL of microparticle coating buffer can be used.

Optionally, prior to contacting the test sample with the at least one first capture antibody, the at least one first capture antibody can be bound to a solid support which facilitates the separation the first antibody-hBNP complex from the test sample. Any solid support known in the art can be used, including but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind hBNP or hBNP fragment. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing hBNP or an hBNP fragment is brought into contact with the at least one first capture antibody, the test sample is incubated in order to allow for the formation of a first capture antibody (or multiple antibody)-hBNP complex. The incubation can be carried out at a pH of from about 4.5 to about 10.0, at a temperature of from about 2° C. to about 45° C., and for a period from at least about one (1) minute to about eighteen (18) hours, preferably from about 2-6 minutes, most preferably from about 3-4 minutes.

After formation of the first/multiple capture antibody-hBNP complex, the complex is then contacted with at least one second detection antibody (under conditions which allow for the formation of a first/multiple antibody-hBNP-second antibody complex). If the first antibody-hBNP complex is contacted with more than one detection antibody, then a first/multiple capture antibody-hBNP-multiple antibody detection complex is formed. As with first antibody, when the at least second (and subsequent) antibody is brought into contact with the first antibody-hBNP complex, a period of incubation under conditions similar to those described above is required for the formation of the first/multiple antibody-hBNP-second/multiple antibody complex. Preferably, at least one second antibody contains a detectable label. The detectable label can be bound to the at least one second antibody prior to, simultaneously with or after the formation of the first/multiple antibody-hBNP-second/multiple antibody complex. Any detectable label known in the art can be used. For example, the detectable label can be a radioactive label, such as, $^3$H, $^{125}$I, $^{35}$S, $^{14}$C, $^{32}$P, $^{33}$P, an enzymatic label, such as horseradish peroxidase, alkaline peroxidase, glucose 6-phosphate dehydrogenase, etc., a chemiluminescent label, such as, acridinium esters, luminal, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, 2nd ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg.

The detectable label can be bound to the antibodies either directly or through a coupling agent. An example of a coupling agent that can be used is EDAC (1-ethyl-3-(3-dimethylaminopropyl) carbodiimide, hydrochloride) that is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9- carboxamide, otherwise known as CPSP-Acridinium Ester or N10-(3-sulfopropyl)-N-(3-sulfopropyl)-acridinium-9-carboxamide, otherwise known as SPSP-Acridinium Ester.

The first antibody/multiple-hBNP-second/multiple antibody complex can be, but does not have to be, separated from the remainder of the test sample prior to quantification of the label. For example, if the at least first capture antibody is bound to a solid support, such as a well or a bead, separation can be accomplished by removing the fluid (from the test sample) from contact with the solid support. Alternatively, if the at least first capture antibody is bound to a solid support it can be simultaneously contacted with the hBNP-containing sample and the at least one second detection antibody to form a first (multiple) antibody-hBNP-second (multiple) antibody complex, followed by removal of the fluid (test sample) from contact with the solid support. If at least first capture antibody is not bound to a solid support, then the first antibody/multiple-hBNP-second/multiple antibody complex does not have to be removed from the test sample for quantification of the amount of the label.

After formation of the labeled first antibody-hBNP-second antibody complex, the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of hBNP or hBNP fragment in the test sample is determined by use of a standard curve that has been generated using serial dilutions of hBNP or hBNP fragment of known concentration. Other than using serial dilutions of hBNP or hBNP fragment, the standard curve can be generated gravimetrically, by mass spectroscopy and by other techniques known in the art.

In a forward competitive format, an aliquot of labeled hBNP, hBNP fragment or hBNP analogue thereof of a known concentration is used to compete with hBNP or hBNP fragment in a test sample for binding to hBNP antibody (such as an antibody of the present invention). Peptides of hBNP, hBNP fragments and hBNP analogues thereof and methods of making peptides of hBNP, hBNP fragments and hBNP analogues are known in the art (See, for example, U.S. Pat. No. 6,162,902). Moreover, as described in the Examples herein, cyclic hBNP (1-32) can also be used in said competitive formats.

In a forward competition assay, an immobilized antibody (such as an antibody of the present invention) can either be sequentially or simultaneously contacted with the test sample and a labeled hBNP, hBNP fragment or hBNP analogue thereof. The hBNP peptide, hBNP fragment or hBNP analogue can be labeled with any detectable label known to those skilled in the art, including those detectable labels discussed above in connection with the sandwich assay format. In this assay, the antibody of the present invention can be immobilized on to a solid support using the techniques discussed previously herein. Alternatively, the antibody of the present invention can be coupled to an antibody, such as an antispecies antibody, that has been immobilized on to a solid support, such as a microparticle (See Example 3).

The labeled hBNP peptide, hBNP fragment or hBNP analogue, the test sample and the antibody are incubated under conditions similar to those described above in connection with the sandwich assay format. Two different species of antibody-hBNP complexes are then generated. Specifically, one of the antibody-hBNP complexes generated contains a detectable label while the other antibody-hBNP complex does not contain a detectable label. The antibody-hBNP complex can be, but does not have to be, separated from the remainder of the test sample prior to quantification of the detectable label. Regardless of whether the antibody-hBNP complex is separated from the remainder of the test sample, the amount of detectable label in the antibody-hBNP complex is then quantified. The concentration of hBNP or hBNP fragment in the test sample can then be determined by comparing the quantity of detectable label in the antibody-hBNP complex to a standard curve. The standard curve can be generated using serial dilutions of hBNP or hBNP fragment of known concentration, by mass spectroscopy, gravimetrically and by other techniques known in the art.

The antibody-hBNP complex can be separated from the test sample by binding the antibody to a solid support, such as the solid supports discussed above in connection with the sandwich assay format, and then removing the remainder of the test sample from contact with the solid support.

The labeled hBNP (or hBNP fragment or hBNP analogue thereof) that is used to compete with hBNP or a hBNP fragment in the test sample for binding to the antibody can be intact hBNP 1-32 (SEQ ID NO:5), any hBNP fragment thereof provided that said hBNP fragment comprises at least one amino acid sequence containing (meaning including and between) amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP) or any hBNP analogue provided that said hBNP peptide, hBNP fragment or hBNP analogue contains a sequence of amino acids that corresponds to an epitope that is recognized by the antibody. Preferably, the antibody employed specifically binds to an epitope comprising at least three (3) amino acids of amino acids 5-13 of hBNP (SEQ ID NO:5) (such as the antibody of the present invention, specifically an antibody produced by CHO cell line AM1) or specifically binds to an epitope having an amino acid sequence that contains (meaning that it includes and is between) amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP. Examples of hBNP fragments that can be labeled and used in the present invention, include, but are not limited to, peptide fragments having an amino acid sequence containing amino acids 1-31, 1-30, 1-29, 1-28, 1-27, 1-26, 1-25, 1-24, 1-23, 1-22, 1-21, 1-20, 1-19, 1-18, 1-17, 1-16, 1-15, 2-32, 2-31, 2-30, 2-29, 2-28, 2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 3-32, 3-31, 3-30, 3-29, 3-28, 3-27, 3-26, 3-25, 3-24, 3-23, 3-32, 3-21, 3-20, 3-19, 3-18, 3-17, 3-16, 3-15, 3-14, 3-13, 3-12, 3-11, 3-10, 3-9, 3-8, 4-32, 4-31, 4-30, 4-29, 4-28, 4-27, 4-26, 4-25, 4-24, 4-23, 4-22, 4-21, 4-20, 4-19, 4-18, 4-17, 4-16, 4-15, 4-14, 4-13, 4-12, 4-11, 4-10, 4-9, 5-32, 5-31, 5-30, 5-29, 5-28, 5-27, 5-26, 5-25, 5-24, 5-23, 5-22, 5-21, 5-20, 5-19, 5-18, 5-17, 5-16, 5-15, 5-14, 5-13, 5-12, 5-11, 5-10, 6-32, 6-31, 6-30, 6-29, 6-28, 6-27, 6-26, 6-25, 6-24, 6-23, 6-22, 6-21, 6-20, 6-19, 6-18, 6-17, 6-16, 6-15, 6-14, 6-13, 6-12, 6-11, 7-32, 7-31, 7-30, 7-29, 7-28, 7-27, 7-26, 7-25, 7-24, 7-23, 7-22, 7-21, 7-20, 7-19, 7-18, 7-17, 7-16, 7-15, 7-14, 7-13, 7-12, 8-32, 8-31, 8-30, 8-29, 8-28, 8-27, 8-26, 8-25, 8-24, 8-23, 8-22, 8-21, 8-20, 8-19, 8-18, 8-17, 8-16, 8-15, 8-14, 8-13, 9-32, 9-31, 9-30, 9-29, 9-28, 9-27, 9-26, 9-25, 9-24, 9-23, 9-22, 9-21, 9-20, 9-19, 9-18, 9-17, 9-16, 9-15, 9-14, 10-32, 10-31, 10-30, 10-29, 10-28, 10-27, 10-26, 10-25, 10-24, 10-23, 10-22, 10-21, 10-20, 10-19, 10-18, 10-17, 10-16, 10-15, 11-32, 11-31, 11-30, 11-29, 11-28, 11-27, 11-26, 11-25, 11-24, 11-23, 11-22, 11-21, 11-20, 11-19, 11-18, 11-17 or 11-16 of hBNP (SEQ ID NO:5).

In a reverse competition assay, an immobilized hBNP peptide, hBNP fragment or hBNP analogue thereof can either be sequentially or simultaneously contacted with a test sample and at least one labeled antibody. Preferably, the antibody specifically binds to an epitope having an amino acid sequence comprising at least three (3) amino acids of amino acids 5-13 of hBNP or to an epitope having an amino acid sequence containing (meaning including and between) amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP (SEQ ID NO:5). An example of an antibody that specifically binds to epitopes having an amino acid sequence containing at least three (3) amino acids of amino acids 5-13 of hBNP (SEQ ID NO:5) is an antibody produced by CHO cell line AM1. The antibody can be labeled with any detectable label known to those skilled in the art, including those detectable labels discussed above in connection with the sandwich assay format.

The hBNP peptide, hBNP fragment or hBNP analogue can be bound to a solid support, such as the solid supports discussed above in connection with the sandwich assay format. Preferably, the hBNP peptide fragment has an amino acid sequence that contains amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP (SEQ ID NO:5).

The immobilized hBNP peptide, hBNP peptide fragment or hBNP analogue thereof, test sample and at least one labeled antibody are incubated under conditions similar to those described above in connection with the sandwich assay format. Two different species hBNP-antibody complexes are then generated. Specifically, one of the hBNP-antibody complexes generated is immobilized and contains a detectable label while the other hBNP-antibody complex is not immobilized and contains a detectable label. The non-immobilized hBNP-antibody complex and the remainder of the test sample are removed from the presence of the immobilized hBNP-antibody complex through techniques known in the art, such as washing. Once the non-immobilized hBNP antibody complex is removed, the amount of detectable label in the immobilized hBNP-antibody complex is then quantified. The concentration of hBNP or hBNP fragment in the test sample can then be determined by comparing the quantity of detectable label in the hBNP-complex to a standard curve. The standard curve can be generated using serial dilutions of hBNP or hBNP fragment of known concentration, by mass spectroscopy, gravimetrically and by other techniques known in the art.

In a fluorescence polarization assay, in one embodiment, an antibody or functionally active fragment thereof is first contacted with an unlabeled test sample suspected of containing hBNP or a hBNP fragment thereof to form an unlabeled hBNP-antibody complex. The unlabeled hBNP-antibody complex is then contacted with a fluorescently labeled hBNP, hBNP fragment or hBNP analogue thereof. The labeled hBNP, hBNP fragment or hBNP analogue competes with any unlabeled hBNP or hBNP fragment in the test sample for binding to the antibody or functionally active fragment thereof. The amount of labeled hBNP-antibody complex formed is determined and the amount of hBNP in the test sample determined via use of a standard curve.

Preferably, the antibody used in a fluorescence polarization assay specifically binds to an epitope having an amino acid sequence comprising at least three (3) amino acids of amino acids 5-13 of hBNP (SEQ ID NO:5) or to an epitope having an amino acid sequence containing (meaning including and between) amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP (SEQ ID NO:5). An example of an antibody that specifically binds to epitopes having an amino acid sequence containing at least three (3) amino acids of amino acids 5-13 of hBNP (SEQ ID NO:5) is a monoclonal antibody produced by CHO cell line AM1.

Preferably, the hBNP peptide fragment has an amino acid sequence that contains amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP (SEQ ID NO:5). The antibody, labeled hBNP peptide, hBNP peptide fragment or hBNP analogue thereof and test sample and at least one labeled antibody are incubated under conditions similar to those described above in connection with the sandwich assay format.

Alternatively, in another embodiment, an antibody or functionally active fragment thereof is simultaneously contacted with a fluorescently labeled hBNP, hBNP fragment or hBNP analogue thereof and an unlabeled test sample suspected of containing hBNP or hBNP fragment thereof to form both labeled hBNP-antibody complexes and unlabeled hBNP-antibody complexes. The amount of labeled hBNP-antibody complex formed is determined and the amount of hBNP in the test sample determined via use of a standard curve. The antibody used in this immunoassay specifically binds to an epitope having an amino acid sequence comprising at least three (3) amino acids of amino acids 5-13 of hBNP (SEQ ID NO:5) or to an epitope having an amino acid sequence containing (meaning including and between) amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP (SEQ ID NO:5). An example of an antibody that specifically binds to epitopes having an amino acid sequence containing at least three (3) amino acids of amino acids 5-13 of hBNP (SEQ ID NO:5) is a monoclonal antibody produced by CHO cell line AM1. Additionally, the hBNP peptide fragment has an amino acid sequence that contains amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP (SEQ ID NO:5).

Alternatively, in yet another embodiment, an antibody (such as antibody of the present invention, such as an antibody produced by CHO cell line AM1) or functionally active fragment thereof is first contacted with a fluorescently labeled hBNP, hBNP fragment or hBNP analogue thereof to form a labeled hBNP-antibody complex. The labeled BNP-antibody complex is then contacted with an unlabeled test sample suspected of containing hBNP or a hBNP fragment thereof. Any unlabeled hBNP or hBNP fragment in the test sample competes with the labeled hBNP, hBNP fragment or hBNP analogue for binding to the antibody or functionally active fragment thereof. The amount of labeled hBNP-antibody complex formed is determined the amount of hBNP in the test sample determined via use of a standard curve. The antibody used in this immunoassay specifically binds to an epitope having an amino acid sequence comprising at least three (3) amino acids of amino acids 5-13 of hBNP (SEQ ID NO:5) or to an epitope having an amino acid sequence containing (meaning including and between) amino acids 13-20, 13-19, 13-18, 13-17, 13-16, 14-20, 14-19, 14-18, 14-17, 14-16, 15-20, 15-19, 15-18, 16-20, 16-19, 17-24, 17-23, 17-22, 17-21, 17-20, 17-19, 18-24, 18-23, 18-22, 18-21, 18-20, 19-24, 19-23, 19-22 or 19-21 of hBNP (SEQ ID NO:5). An example of an antibody that specifically binds to epitopes having an amino acid sequence containing at least three (3) amino acids of amino acids 5-13 of hBNP (SEQ ID NO:5) is a monoclonal antibody produced by CHO cell line AM1. Additionally, the hBNP peptide fragment has an amino acid sequence that contains amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP (SEQ ID NO:5).

VII. Pharmaceutical Compositions and Pharmaceutical Administration

The antibodies of the present invention can be incorporated into pharmaceutical compositions suitable for administration to a subject. Typically, the pharmaceutical composition comprises a therapeutically or pharmaceutically effective amount of an antibody or the present invention along with a pharmaceutically acceptable carrier or excipient. As used herein, "pharmaceutically acceptable carrier" or "pharmaceutically acceptable excipient" includes any and all solvents, dispersion media, coating, antibacterial and antifungal agents, isotonic and absorption delaying agents, and the like that are physiologically compatible. Examples of pharmaceutically acceptable carriers or excipients include one or more of water, saline, phosphate buffered saline, dextrose, glycerol, ethanol and the like as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or antibody portion also may be included. Optionally, disintegrating agents can be included, such as cross-linked polyvinyl pyrrolidone, agar, alginic acid or a salt thereof, such as sodium alginate and the like. In addition to the excipients, the pharmaceutical composition can include one or more of the following, carrier proteins such as serum albumin, buffers, binding agents, sweeteners and other flavoring agents; coloring agents and polyethylene glycol.

The compositions of this invention may be in a variety of forms. They include, for example, liquid, semi-solid and solid dosage forms, such as liquid solutions (e.g. injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody or antibody fragment is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e. antibody or antibody fragment) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the present invention can be administered by a variety of methods known in the art, although for many therapeutic applications, the preferred route/mode of administration is intravenous injection or infusion. As will be appreciated by those skilled in the art, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. (See, e.g. *Sustained and Controlled Release Drug Delivery Systems*, J. R. Robinson, ed., Marcel Dekker, Inc., New York, 1978).

In certain embodiments, an antibody of the present invention may be orally administered, for example, with an inert diluent or an assimilable edible carrier. The compound (and other ingredients if desired) may also be enclosed in a hard or soft shell gelatin capsule, compressed into tablets, buccal tablets, troches, capsules, elixirs, suspensions, syrups, wafers, and the like. To administer an antibody or antibody fragment of the invention by other than parenteral administration, it may be necessary to coat the compound with, or co-administer the compound with, a material to prevent its inactivation.

Supplementary active compounds also can be incorporated into the compositions. In certain embodiments, the antibody or antibody portion is co-formulated with and/or co-administered with one or more additional therapeutic agents. Such combination therapies may advantageously utilize lower dosages of the administered therapeutic agents, thus avoiding possible toxicities or complications associated with monotherapies or alternatively, act synergistically or additively to enhance the therapeutic effect.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be tested; each unit containing a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic or prophylactic effect to be achieved and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 0.5-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Now by way of example, and not of limitation, examples of the present invention shall now be given.

EXAMPLE 1

Identification of Immunoglobulin Genes

Figure 2:
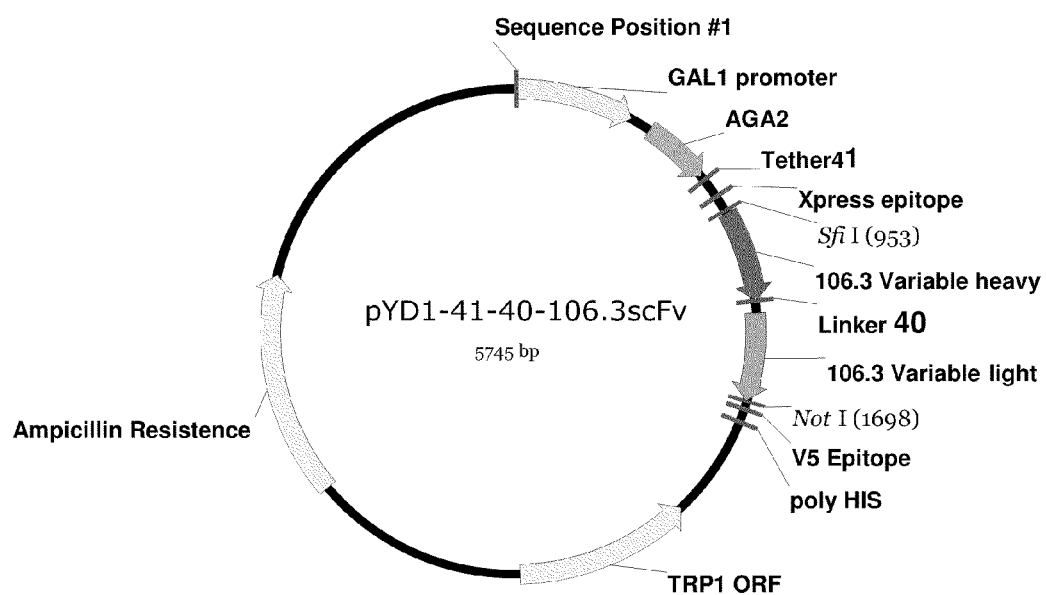
FIG. 2 is a plasmid map for vector pYD41-40 containing the 106.3 single-chain variable fragment shown in FIG. 4.

Messenger RNA was isolated from subcloned anti-BNP 106.3 hybridoma cells (hybridoma cell line 106.3 (A.T.C.C. Accession No. HB-12044) is described in U.S. Pat. No. 6,162,902). 106.3 mRNA was utilized in a reverse transcriptase-polymerase chain reaction using a mouse Ig primer set kit purchased from Novagen (Novagen (which is an Affiliate of Merck KGaA, Darmstadt, Germany), Cat No. 69831-3) with immunoglobulin gene specific primers contained in the kit. The resulting PCR products were sequenced and thus the immunoglobulin variable heavy and variable light chain genes were identified (See FIGS. 3A-3E and SEQ ID NO: 1).
Cloning 106.3 Variable Region Genes into pYD41 Vector A yeast display system was used to express unmutated anti-BNP proteins (described herein infra) and a library of anti-BNP proteins on the yeast surface as a fusion to the yeast protein AGA2. A yeast display vector called pYD (Invitrogen, Carlsbad, Calif.), was used as it allows for cloning of the anti-BNP gene at the C-terminus of the AGA2 gene, a yeast mating factor (See, Boder and Wittrup, *Nature Biotechnology*, 15:553-557 (June 1997). Other critical features of the pYD vector include a galactose inducible promoter and an epitope tag, V5, on the C-terminus of the inserted anti-BNP gene (See, FIG. 2 and FIG. 6A-6B).

The yeast display platform utilizes an antibody format known as the single-chain variable fragment. In the scFv format, the variable heavy domain is connected to the variable light domain through a flexible linker (variable heavy domain—Linker GPAKELTPLKEAKVS (SEQ ID NO:4)—variable light domain).

Figure 4:
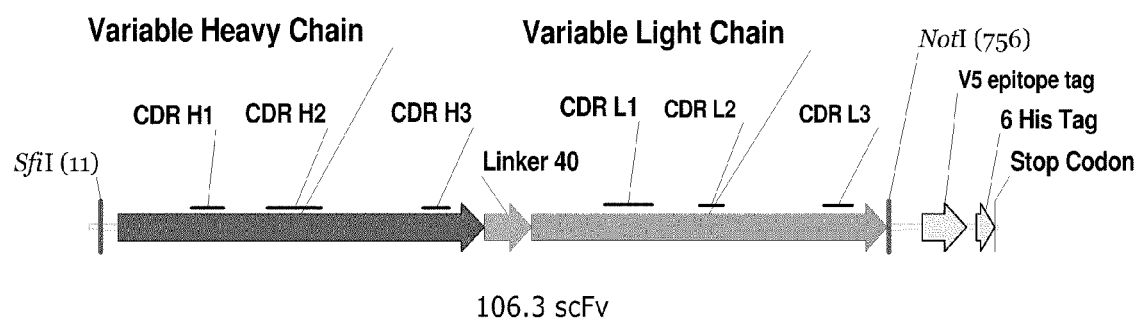
FIG. 4 is a diagram of the 106.3 single-chain variable fragment ("scFv").

PCR single overlap extension (SOE) was used to combine the variable heavy (VH) and the variable light genes (VL) for the 106.3 scFv construct (See, e.g., FIGS. 4, 6A-6B, and SEQ ID NO:2). The 106.3 scFv DNA was cloned into the yeast display vector pYD41 using vector restriction sites SfiI and NotI. The pYD41-106.3scFv vector was transformed into DH5α *E. coli*. Plasmid DNA was then isolated from the *E. coli* and the 106.3 scFv insert was sequenced to ensure the scFv was cloned in frame with the AGA2 protein.

The cloning site for the scFv into the yeast display vector pYD41 is in an ORF that includes the following genes: AGA2-tether linker 41-X press epitope tag-106.3 variable heavy chain-Linker 40-106.3 variable light chain-V5 epitope tag—Six His tag. In addition, the yeast strain EBY100 is a tryptophan auxotroph and the pYD41 vector encodes for tryptophan as the system's selectable marker.
Transformation into *Saccharomyces cerevisiae* Strain EBY100

Figure 7A:
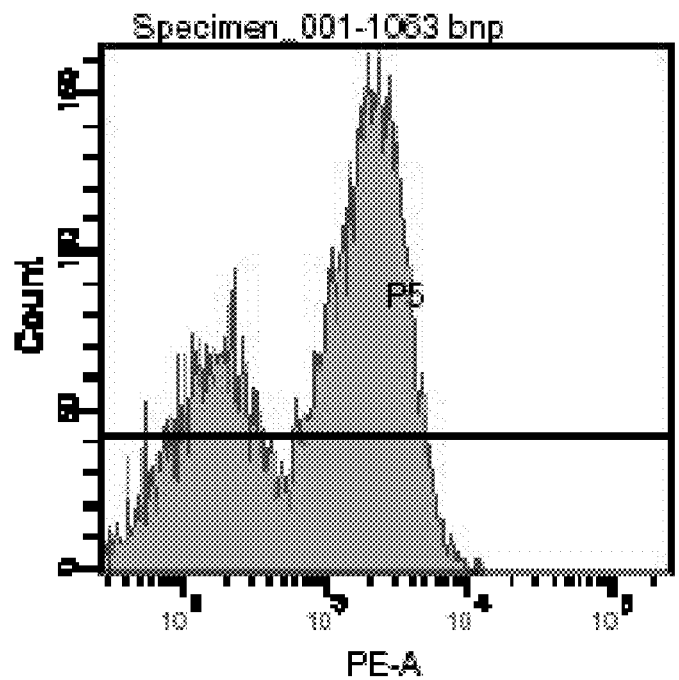
FIGS. 7A-7B show that yeast expressing full-length 106.3 single-chain variable fragment (scFv) bind to cyclic BNP (SEQ ID NO:5) More specifically, this figure shows that 106.3 scFv expressing yeast were incubated with cyclic BNP (1-32c) (SEQ ID NO:5) or anti-V5 followed by secondary reagents streptavidin phycoerythrin (SA:PE) (FIG. 7A) and goat anti mouse-phycoerythrin (GAM:PE) (FIG. 7B). The flow cytometry histograms illustrate the full-length expression of 106.3 scFv as detected by anti-V5 and the ability of 106.3 scFv to bind to cyclic BNP peptide (1-32) (SEQ ID NO:5). PEA units (abscissa): $10^2$, $10^3$, $10^4$, and $10^5$. Count units (ordinate): 0, 50, 100, 150 (FIG. 7A); 0, 25, 50, 75, 100, 125 (FIG. 7B).
Figure 7B:
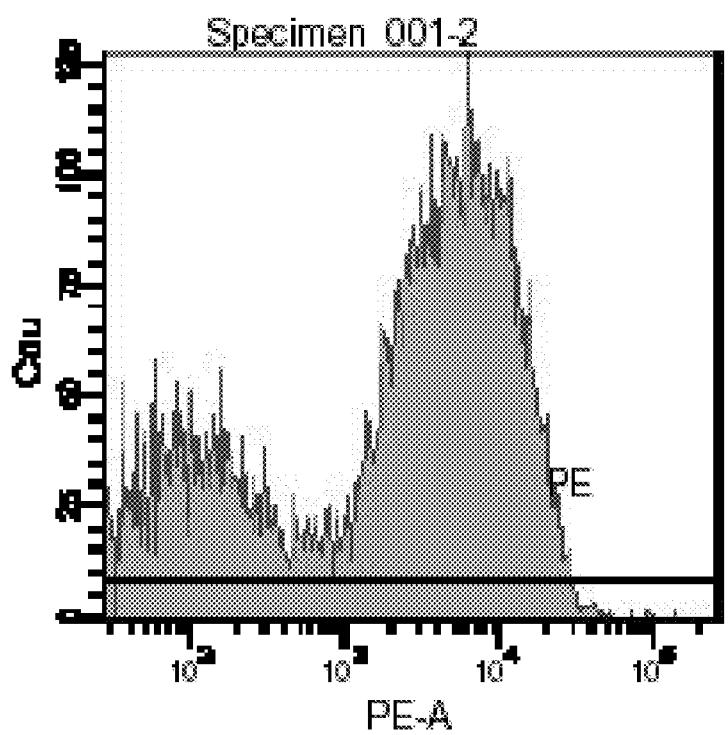

Yeast display plasmid, pYD41-106.3 scFv, was transformed into *S. cerevisiae* EBY100 using Gietz and Schiestl Method (See, Schiestl and Gietz, Current Genetics, 16(5-6): 339-46 (December 1989)). Dilutions of the transformation reaction were plated on selective glucose plates (2% glucose (0.67% yeast nitrogen base, 0.105% HSM-trp-ura, 1.8% bacterial agar, 18.2% sorbitol, 0.86% NaH$_2$PO$_4$H$_2$O, 1.02% Na$_2$HPO$_4$7H$_2$O)) and incubated at 30° C. for 48-72 hours. Selective glucose media was inoculated with individual colonies and grown shaking at 30° C. for 16-20 hours. Protein expression was induced in colonies by transferring 0.5 OD600 of cells/ml (1e7 cells/0.50 D/ml) to selective galactose media. Colonies were shaken at 20° C. for 16-24 hours and then analyzed by the FACS Aria flow cytometer for binding to cyclic BNP (referred to as "1-32c") (SEQ ID NO:5) and anti-V5. For flow cytometry assays, yeast cells expressing 106.3 scFv were incubated with biotinylated: cyclic BNP (1-32c) (SEQ ID NO:5) or anti-V5 antibody followed by streptavidin: phycoerythrin (SA:PE, BD Pharmingen) or goat anti-mouse immunoglobulin-Alexa Fluora 633 (GAM:633, Molecular Probes (which is an Affiliate of Invitrogen, Carlsbad, Calif.)). The flow cytometry histograms as shown in FIGS. 7A-7B illustrate full-length surface expression of 106.3 scFv (anti-V5 binding) and binding of 106.3 scFv to cyclic BNP (1-32c) (SEQ ID NO:5).
Off-Rate Analysis for 106.3 scFv and 106.3 Variants on Yeast.

Figure 8:
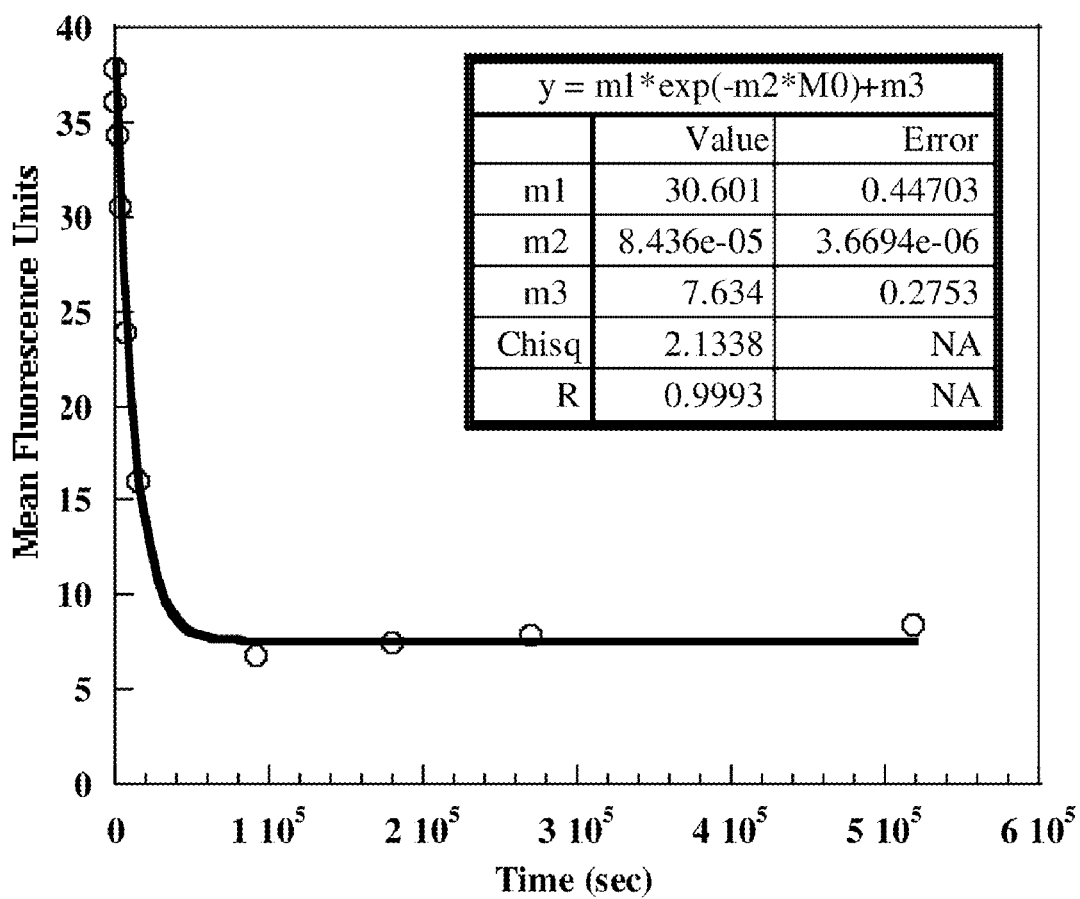
FIG. 8 shows the 106.3 scFv off-rate measurement. More specifically, yeast expressing 106.3 scFv were incubated with a saturating concentration of biotinylated cyclic BNP (1-32c) (SEQ ID NO:5). Cells were then washed and incubated with a saturating concentration of unlabelled BNP 1-32c (SEQ ID NO:5). At each time point, cells were transferred to ice, washed and incubated with SA:PE. After 30 minutes, cells were washed again and analyzed on the flow cytometer. A first order decay equation was used to fit the individual time points where m1 was the theoretical maximum mean fluorescence units ("MFU") at time 0, m2 was the off-rate ("koff"), m3 was the background MFU due to autofluorescence and M0, which is the time x (the x being the time that is being measured) was the time x that measurements are taken. The half-life (t$_{1/2}$) of 106.3 scFv binding to cyclic BNP (1-32c) was calculated using: t$_{1/2}$=ln 2/k$_{off}$. One and a half times the half-life was the time used to sort the 106.3 CDR mutagenic libraries.

Off-rate measurements of 106.3scFv and 106.3 variants on yeast were measured by incubating 0.050 D yeast (1×10$^6$ cells) with 100-fold molar excess of biotinylated-cyclic BNP 1-32c (~0.3 µM) (SEQ ID NO:5) and anti-V5 antibody (2.5 ug/ml) for 30-60 minutes at room temperature. Cells were then washed twice with blocking buffer containing phosphate buffered saline with 1% bovine serum albumin (PBS/BSA) and incubated at room temperature with 100-fold molar excess unlabelled cyclic BNP 1-32c (SEQ ID NO:5) for varying amounts of time (0, 0.25 hr, 0.5 hr, 1 hr, 2 hr, 4.25 hr, 25.5 hr, 50 hr 75 hr and 144 hr (See FIG. 8). At each individual time point, yeast cells were transferred to ice to halt the reaction. Cells were then washed twice with PBS/BSA and suspended in secondary staining reagents, specifically, SA:PE and GAM:633. Cells were incubated on ice for 30 minutes, washed twice and then analyzed on the FACS Aria flow cytometer. FIG. 8 shows the off-rate data plotted as mean fluorescence units ("MFU") versus time (in seconds). A first order decay equation was used to fit the data. The off-rate, m2 in the equation shown in FIG. 8, was fitted to 8.4-5 sec$^{-1}$ with and R value of 0.9993. The 106.3 scFv half-life ($t_{1/2}$) was 137 min ($t_{1/2}$=ln 2/k$_{off}$).

An off-rate sorting strategy was used to identify off-rate improved 106.3 variants from mutagenic libraries. Therefore, the 106.3 scFv, unmutated or wildtype ("wt"), half-life was used to determine the appropriate time to sort the mutagenic libraries. 106.3 mutagenic libraries were sorted approximately 3 hours after the addition of unlabelled cyclic BNP (1-32c) (SEQ ID NO:5) with the same assay conditions described for wt 106.3 scFv.

Generation of 106.3 CDR Directed Libraries

Figure 9:
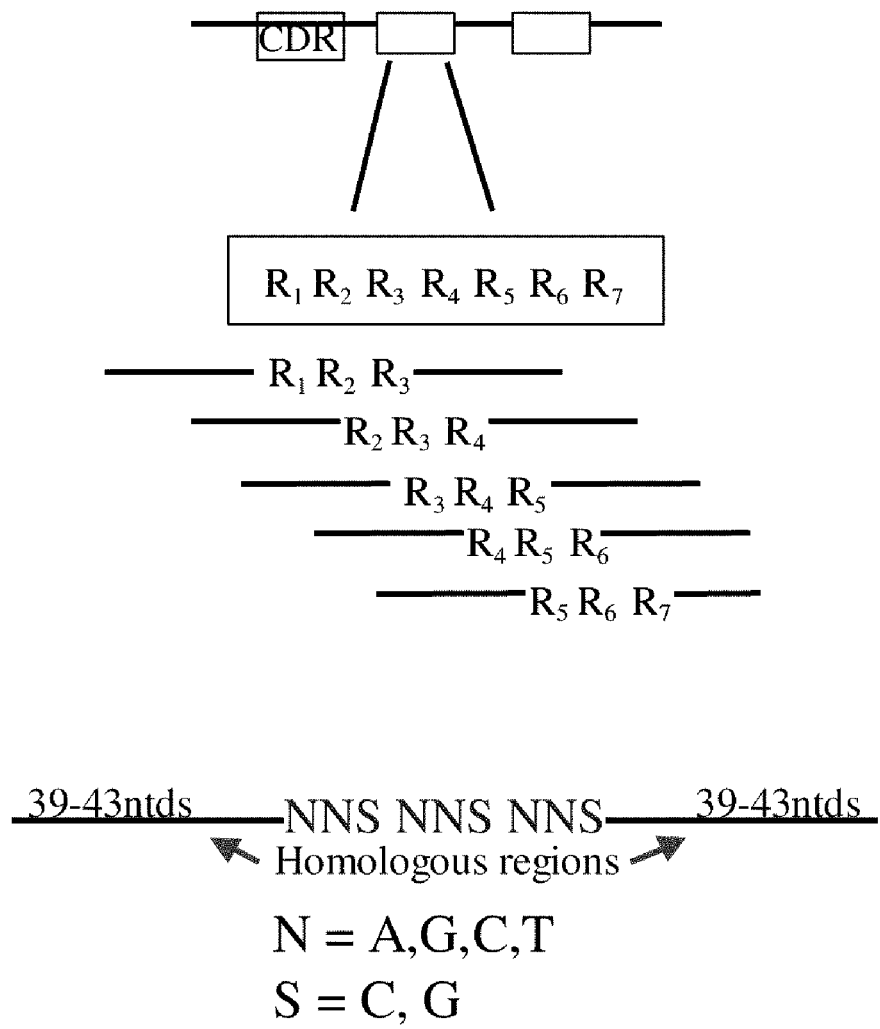
FIG. 9 is a schematic depiction which shows how degenerate oligonucleotides were designed so that three amino acid positions of the complementarity determining region (9 nucleotides) were randomly mutated per library.

Mutagenesis was directed to the three heavy and three light chain complementary determining regions (CDR) of antibody 106.3 (See, e.g., FIGS. 3-6 and SEQ ID NOS:6-11) since these loops are the major antigen contact sites. CDR loop lengths and numbering were defined using Kabat nomenclature. Individual libraries were composed that randomly mutated three amino acid positions of the CDR in a single library with the mutagenic window shifted by one amino acid per library (See, FIG. 9). The library diversity for an individual library totaled $20^3$ or 8,000 possible variants with every amino acid sampled at every CDR position. For 106.3scFv, a total of 54 libraries were generated 29 variable heavy and 25 variable light libraries.

Figure 10:
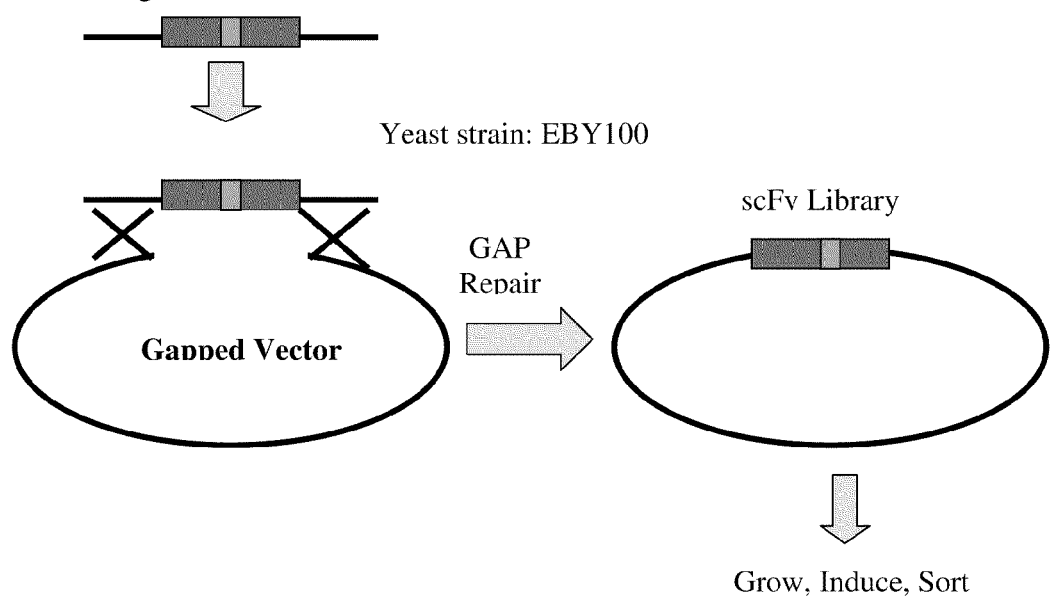
FIG. 10 is a schematic depiction which shows how the 106.3 scFv library was constructed using yeast homologous recombination. More specifically, gapped vectors were PCR generated to exclude those nucleotides that were being mutagenized in the library. The degenerate single stranded oligonucleotides were synthesized. Gapped vectors and single stranded degenerate oligonucleotides were transformed into *S. cerevisiae* strain EBY100. Transformed clones were selected in tryptophan deficient glucose media.

Libraries were generated by combining linearized gapped pYD41-106.3 vector and single stranded oligonucleotides with chemically competent EBY100 yeast (See, FIG. 10). The gapped pYD41 vector is a vector created by PCR that lacks a specific region of each CDR that is replaced in library construction by the single stranded degenerate oligonucleotide. Degenerate single-stranded oligonucleotides are 90-105 nucleotides long with 39-43 nucleotides of homology to the pYD41-106.3 scFv vector on each side of the nine degenerate nucleotide window. The oligonucleotides for each library, 54 total, were synthesized (See FIGS. 14A-H and SEQ ID NOS:25-78). Gapped vector (1 ug) and the degenerate oligonucleotide (16 ug) were combined with EBY100 yeast (3e8 cells) and transformed using the Gietz and Schiestl library transformation protocol (Schiestl and Gietz, *Current Genetics,* 16(5-6):339-46 (December 1989)). The degenerate oligonucleotide and the pYD41-106.3scFv gapped vector cyclize during transformation due to homologous recombination facilitated by the nucleotide overlap and the mechanism of yeast endogenous gap repair. Libraries were grown at 30° C. for 48-72 hours in selective glucose media and passed again in selective glucose media prior to induction of protein expression for library sorting.

106.3 Mutagenic CDR Libraries 106.3 libraries were sorted based on an off-rate sorting strategy. 106.3 CDR mutagenic libraries were induced in galactose expression media at 20° C. for 18-24 hours. At room temperature, 106.3 mutagenic libraries were washed with PBS/BSA, incubated with biotinylated cyclic BNP (1-32c) (SEQ ID NO:5) and anti-V5 antibody, washed twice and incubated with unlabelled cyclic BNP (1-32c) (SEQ ID NO:5). After three hours, mutagenic libraries were washed twice and incubated on ice with SA-PE (1:200 dilution) and GAM-633 (1:200 dilution) for 30 minutes. Finally, cells were washed, analyzed and sorted on the FACS Aria. Sort gates were set based on unmutated 106.3 binding at 3 hours with a gate set to sort full-length BNP binding clones. Each sort collected the top 0.1-0.5% of the BNP binding population. Sorted cells were grown in selective glucose media and grown 18-24 hours at 30° C. Sort 1 cells were induced and sorting was repeated for one or two additional rounds.

After the last sort, sorted cells were plated onto selective glucose plates and placed at 30° C. for 72 hours. Three libraries showed improvements relative to wt 106.3 scFv: heavy chain library H2 8, light chain library L1 (1-5 pool), and L2 (1-5 pool). Individual yeast colonies from these libraries were inoculated in selective glucose media, cryopreserved and induced in selective galactose media. Individual colonies were then characterized and ranked in an off-rate assay.

Analysis of Selected 106.3 Variants

Selected clones were initially characterized in the off-rate assay described above for wt 106.3 scFv. FIG. 11 shows the off-rate values determined from a first order decay curve for each improved 106.3 scFv variant evaluated. Overall, clones exhibited improvements in off-rate better than 2-fold that of the 106.3 scFv wt clone. The clone with the desired slowest off-rate was 106.3 L1 B24 scFv with an off rate of $6.7 \times 10^{-6}$ sec$^{-1}$.

Selected 106.3 scFv variants were sequenced to determine the amino acid mutations being expressed. Initially, plasmid DNA was isolated from yeast suspension cultures using a yeast mini-prep kit (Cat No. D2001, Zymo Research Orange, Calif.). In order to obtain sequencing grade plasmid DNA, plasmid from the yeast mini-prep kit was transformed into DH5α *E. coli*, and then purified from culture using *E. coli* mini-prep kits (Qiagen). Pure plasmid DNA was then sequenced using pYD41 vector specific primers (pYD41 for—TAGCATGACTGGTGGACAGC (SEQ ID NO:79) and pYD41rev-CGTAGAATCGAGACCGAG (SEQ ID NO:80)). Nucleotide and amino acid sequence data for 106.3 scFv variants is shown in FIGS. 12A-C. Position numbers refers to amino acid position in the respective CDR(H2 Pos 8 is 8th amino acid of CDR H2).

The sequence data for CDR L1 indicated a strong preference at position 4 for tryptophan or other bulky hydrophobic amino acids such as tyrosine or phenylalanine. A bulky amino acid residue at position 4 may be crucial for the substantial improvements in off-rate for the 106.3 scFv. The cyclic BNP (1-32c) peptide (SEQ ID NO:5) may become trapped by this bulky amino acid and thus slowing the off-rate. The L2 mutations both contain a cysteine at position 4.

Cloning and Soluble Expression of 106.3 Chimeric Antibodies in a Transient or Stable Expression System Selected 106.3 variants were converted to chimeric mouse-human IgG$_1$/human kappa antibodies through cloning of the 106.3 variable domains into the transient expression vector system called pBOS (Abbott Bioresearch Center, Worcester, Mass.) More specifically, PCR was used to amplify the variable heavy and variable light chain genes with restriction sites for cloning into separate pBOS vectors (Mizushima and Nagata, *Nucleic Acids Research,* 18:5322, (1990)). The variable heavy and variable light genes were ligated in digested/dephosphorylated vector and transformed into DH5α *E. coli*. Plasmid DNA was purified from *E. coli* and transfected into COS-7 cells and 293H cells using lipofectamine (Invitrogen, Carlsbad, Calif.) or electroporation. Transient antibody was expressed for the following 106.3 variants: wt chimeric, L1 B24 chimeric, L1 16 chimeric, L1 B24/H2 288 chimeric, and L1 16/H2 288 chimeric.

Using the pBOS-106.3 heavy and light vectors, a stable CHO cell line plasmid was created in a two step cloning procedure. First, variable heavy chain and variable light genes were ligated in frame to the human constant genes in pBV and pJV plasmids (Abbott Bioresearch Center, Worcester, Mass.), respectively, using the restriction enzymes SrfI/NotI. Ligation reactions were transformed into DH5α *E. coli* and plasmid DNA was subsequently isolated from individual colonies. The pBV-106.3 mouse variable heavy-human IgG$_1$ and pJV-106.3 mouse variable light-human kappa were sequenced at the cloning sites.

The second cloning step involved combining the heavy chain IgG$_1$ genes and the light chain kappa genes into a single stable cell line vector. The pBV-106.3 and pJV-106.3 vectors were digested with AscI/PacI. The VL-human kappa constant and the VH-human IgG1 constant DNA fragments were gel purified and ligated to produce the stable cell line vector called pBJ-106.3. The pBJ-106.3 heavy/light chimeric plasmid was transformed into CHO cells using calcium phosphate protocol. Stable cell lines were subcloned from initial transformation. A stable CHO cell line has been developed for the clone AM1 (also referred to as "BNP106.3sc128am1CHO1162-236" and "106.3 L1 B24/H2 288 chimeric") and deposited with the A.T.C.C. as described in Example 2 herein.

BIAcore Characterization of Engineered Chimeric 106.3 Variants

A high density Goat Anti-human Fc (GAHFc) antibody (Jackson ImmunoResearch Laboratories, West Grove, Pa.) (an antispecies antibody) surface plasma resonance (SPR) biosensor was prepared by immobilizing GAHFc to a preconditioned BIAcore CM5 chip (Uppsala, Sweden) by amine coupling (amino coupling is well known in the art, for example, see Nordin, H et al., *Analytical Biochemistry*, 340: 359-368 (2005)). The carboxymethyl-dextran biosensor is activated with an 8 minute injection of a 1:1 mixture of 0.4 M EDC and 0.1 NHS at 20 µL/minute. GAHFc in 10 mM sodium acetate (pH 5.0) is coupled to the activated surface with a 10 minute injection. The surface is then deactivated with 1 M ethanolamine pH 8.5 for 8 minutes followed by another 10 minute injection of GAHFc. This is followed with a biosensor conditioning of ten 20 second injection of 100 mM $H_3PO_4$ at a flow rate of 100 µL/min. ~10.5 kRU, resonance units, of GAHFc is coupled to the biosensor in each flow cell.

Purified anti-BNP chimeric antibodies ("cAb"): (1) stable 106.3 AM1 from CHO cells (described above and in Example 2), and (2) transient anti-BNP WT/WT from COS cells are diluted into SPR Running Buffer (BIAcore, Uppsala, Sweden) (degassed/vacuum-filtered HBS-EP (BIAcore, Sweden)) supplemented with 12 mg/mL BSA and 12 mg/mL carboxymethyl dextran sodium salt) to a concentration of 10 µg/mL of purified antibody. A frozen (−80° C.) aliquot of BNP in $dH_2O$ at 100 µM is diluted into SPR Running Buffer to a concentration of 100 µM.

At 25° C., 30 µL of each anti-BNP cAbs are injected at 10 µL/min onto individual SPR flow cells with one flow cell left blank as a reference control. After loading each cAb onto the biosensor, all flow cells are allowed to equilibrate for 45 minutes with SPR running buffer at a flow rate of 100 µL/min before the running buffer bottle is substituted (in between syringe fills) for a sample solution of 100 µM BNP for ~16 hours. The sample solution is then switched back to SPR running buffer for another ~7 hours. The surface is then regenerated with three 33 second pulses of 100 mM phosphoric acid at a flow rate of 100 µL/min. A blank run is performed by running SPR running buffer over an anti-BNP cAb loaded sensor for ~23 hours.

The data was double-referenced corrected (the 100 µM BNP sample data was corrected by subtracting the reference data and then subtracting blank buffer data) and fitted to a 1:1 Langmuir Binding model (See, *BIA Evaluation 3 Software Handbook*, edition November 1999 (version AD) Copyright 1997-1999, Biacore AB) with considerations for mass transport and linear drift with BIAevaluation software (version 3.2).

Using BIAcore SPR, the equilibrium dissociation constant ($K_D$) of the wild-type 106.3 cAb was determined to be $1.9 \times 10^{-11}$ M with an on-rate of $7.8 \times 10^6$ $M^{-1}sec^{-1}$ and an off-rate of $1.5 \times 10^4$ $sec^{-1}$. The equilibrium dissociation constant ($K_D$) of the 106.3 AM1 cAb was determined to be $1.9 \times 10^{-12}$ M with an on-rate of $1.3 \times 10^7$ $M^{-1}sec^{-1}$ and an off-rate of $2.4 \times 10^{-5}$ $sec^{-1}$. Similar $K_D$ values were obtained for both 106.3 and 106.3 AM1, $1.7 \times 10^{-12}$ M and $9.3 \times 10^{-12}$ M respectively, using Sapidyne's KinExA instrument that determines $K_D$ values in a solution phase measurement (Sapidyne, Boise, Id.).

Specificity of Engineered Chimeric 106.3 Variants

Anti-BNP 106.3 AM1 BNP Truncated BNP Peptide Displacement EIA

Figure 18:
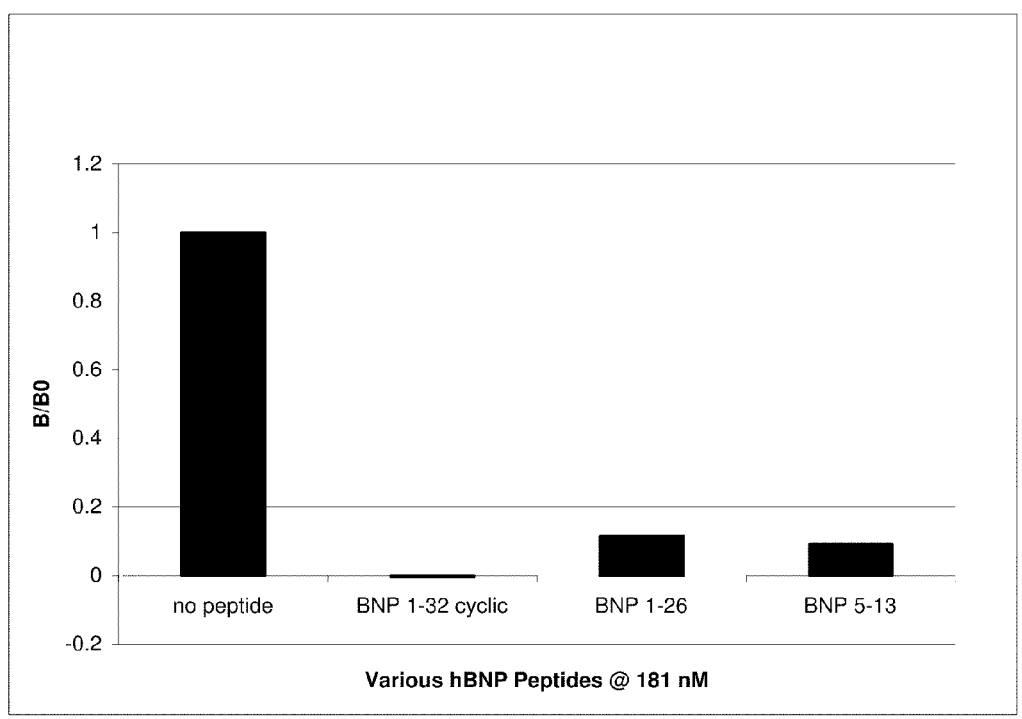
FIG. 18 shows the displacement of antibody AM1 (used at about 0.01 μg/mL) with various hBNP peptides (used at about 181 nM).

The 106.3 AM1 mAb's ability to bind to truncated forms of hBNP, namely hBNP 1-26 and hBNP 5-13, was determined in a displacement microtiter CIA (See, FIG. 18). Blocked antispecies coated plates were incubated with mAb for 1 hour and washed. Serially diluted free, unconjugated hBNP 1-26 (Abbott, Abbott Park, Ill.), hBNP 5-13 (AnaSpec, San Jose, Calif.), hBNP 1-32 (Peptide Institute, Osaka, Japan) peptides or a 0 peptide control were allowed to react with the AM1 mAb for one hour. The plates were washed and an acridinylated hBNP (1-32 cyclic) conjugate (Abbott ADD, Abbott Park, Ill.) was added. The plates were once again incubated and washed. The Relative Luminescence Units (RLUs) were obtained from the chemiluminescence signal generated as the serially-layered pre-trigger/trigger combination (Abbott, Abbott Park, Ill.) on the Microbeta Jet (Perkin-Elmer, Turku, Finland). Anti-BNP 106.3 AM1 mAb was found to be reactive to the free hBNP fragments amino acids 1-26 and amino acids 5-13 as demonstrated by >85% signal displacement in the microtiter assay.

Fine Epitope Mapping of Engineered Chimeric 106.3 Variants

Anti-BNP 106.sc128 L1 B24H2 288 AM1 Alanine Peptide Mapping EIA

The binding site of the 106.3 AM1 mAb was identified using an alanine mutagenesis screening procedure with a cyclic hBNP 1-32 alanine substituted peptide panel. Single amino acids of the hBNP (SEQ ID NO:5) peptide were replaced with an alanine amino acid (except at positions 10 and 26). The 106.3 AM1 mAb was evaluated for its ability to bind the unlabelled alanine substituted peptides versus labeled hBNP 1-32 peptide. The mAb at a constant concentration is incubated on the solid phase coated with an antispecies antibody, then the unbound sample is washed away. The bound antibody is allowed to react with the 2900 nM unlabeled peptides. Following incubation, a wash is used to eliminate any unbound free peptide. Next, the biotinylated hBNP 1-32 cyclic peptide (Abbott GPRD, Abbott Park, Ill.) at 2.9 nM is allowed to react with any unbound sites on the anti-BNP 106.3 AM1 mAb. Unbound peptide is washed away prior to the addition of strepavidin-HRPO (Invitrogen, Carlsbad, Calif.). The OPD substrate system (Abbott, Abbott Park, Ill.) was used for color development and signals read on a Titertek MAP EIA workstation (Titertek Instruments, Huntsville, Ala.).

Figure 19:
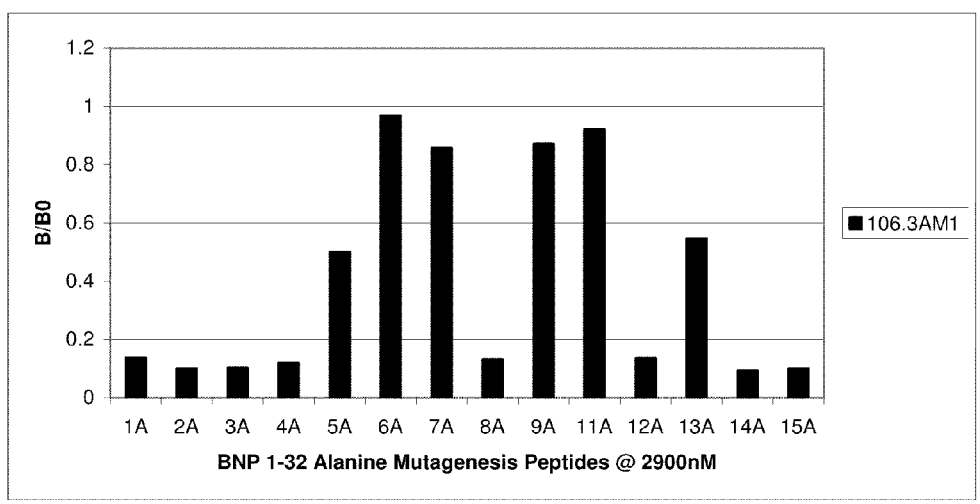
FIG. 19 shows the alanine peptide mapping of antibody AM1 using EIA.

This signal displacement EIA assay was used as a tool to determine the fine epitope mapping profile of the 106.3 AM1 mAb. The free peptide concentration was 2-log over that of the labeled peptide to ensure that inhibition occurs. The bar graph in FIG. 19 shows the bound over unbound (B/B0) ratio of the AM1 antibody binding signal of free peptide versus labeled peptide. If an amino acid residue is critical for AM1 mAb binding to hBNP, partial to no displacement of signal is detected. In this example, if a B/Bo ratio of >0.4 is obtained, the specific amino acid is considered critical for mAb binding. The 106.3AM1 mAb functional epitope is identified as V5, Q6, G7, G9, F11, and R13 in bold in the sequence below.

(SEQ ID NO: 5)
NH2-SPKMVQGSGCFGRKMDRISSSSGLGCKVLRRH-COOH

Anti-BNP 106.sc128 L1 B24H2 288 AM1Alanine Peptide Mapping with BIAcore

A high density Goat Anti-human Fc (GAHFc) antibody (Jackson ImmunoResearch Laboratories, West Grove, Pa.) (an antispecies antibody) surface plasma resonance (SPR) biosensor was prepared by immobilizing GAHFc to a preconditioned BIAcore CM5 chip (Uppsala, Sweden) by amine coupling as described above.

At 25° C., 60 ul of the anti-BNP AM1 cAb are injected at 10 μL/min onto individual SPR flow cells with one flow cell left blank as a reference control. After loading each cAb onto the biosensor, all flow cells are allowed to equilibrate for 10 minutes with SPR running buffer at a flow rate of 100 μL/min. 200 ul of BNP peptide or BNP single alanine substituted peptides (alanine substituted at each position except 10 and 26) at 10 nM was flowed over the AM1 surface at 100 uL/min. Dissociation was allowed to take place and monitored for 1800 seconds. The surface is then regenerated as previously described herein.

Figure 20:
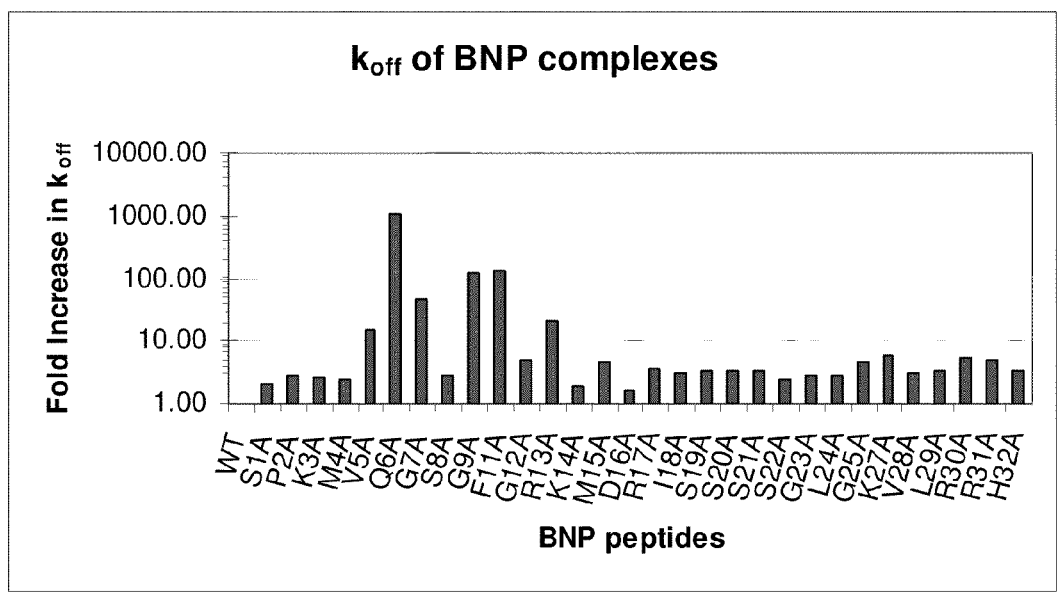
FIG. 20 shows the alanine peptide mapping of antibody AM1 using BIAcore. The fold increase in $k_{off}$ of BNP complexes comprising various BNP peptides are displayed.

The data was double-referenced corrected (the sample data was corrected by subtracting the reference data and then subtracting blank buffer data). Off-rates were determined from the dissociation phase of sensograms. Results indicate that amino acids V5, Q6, G7, G9, F11, and R13 are important for stability of the anti-BNP AM1/WT BNP complex. When these residues are individually mutated into alanine, the off-rate increases by at least one order of magnitude. This suggests that the anti-BNP AM1 cAb binding epitope for BNP contains the following BNP residues V5, Q6, G7, G9, F11, and R13A, in accordance with the EIA findings noted above (See FIG. 20).

EXAMPLE 2

ATCC Deposit Information

Chinese Hamster Ovary cell line for BNP106.3sc128am1CHO1162-236 was deposited with the American Type Culture Collection (hereinafter referred to as "A.T.C.C."), 10801 University Blvd., Manassas, Va. 20110-2209, on Sep. 20, 2005 and assigned A.T.C.C. Accession No. PTA-6987.

EXAMPLE 3

Competitive Immunoassay Using a Single Antibody Format

The antibody produced by CHO cell line AM1 ("antibody AM1") described above in Examples 1 and 2 was purified and tested to determine the antibody's ability to bind human cyclic BNP1-32 in a single antibody format on the ARCHITECT® instrument (Abbott Laboratories, Abbott Park, Ill. This instrument is described in U.S. Pat. No. 5,468,646). This single antibody format encompasses the use of only one analyte specific antibody in the testing reaction.

Paramagnetic microparticles (hereinafter "microparticles", Polymer Labs, Amherst, Mass.) were washed and then reacted with serially diluted Goat anti-human antibody (Jackson ImmunoResearch, West Grove, Pa.). The Goat anti-human antibody was coated onto the paramagnetic microparticles using the techniques described in U.S. Pat. No. 6,162,902. Specifically, EDAC coupling was used (EDAC is generally used as a carboxyl activating agent for amide bonding with primary amines. In addition, it reacts with phosphate groups. It is used in peptide synthesis, crosslinking proteins to nucleic acids and in preparing immunoconjugates. The chemical formula for EDAC is 1-ethyl-3-(3-dimethylaminopropyl)carbodiimide, hydrochloride. EDAC is commercially available from Sigma-Aldrich, St. Louis, Mo.). After incubating, the microparticles were washed and overcoated with BSA. These Goat anti-human coated microparticles were then reacted with serially diluted antibody AM1, incubated and washed.

Figure 15:
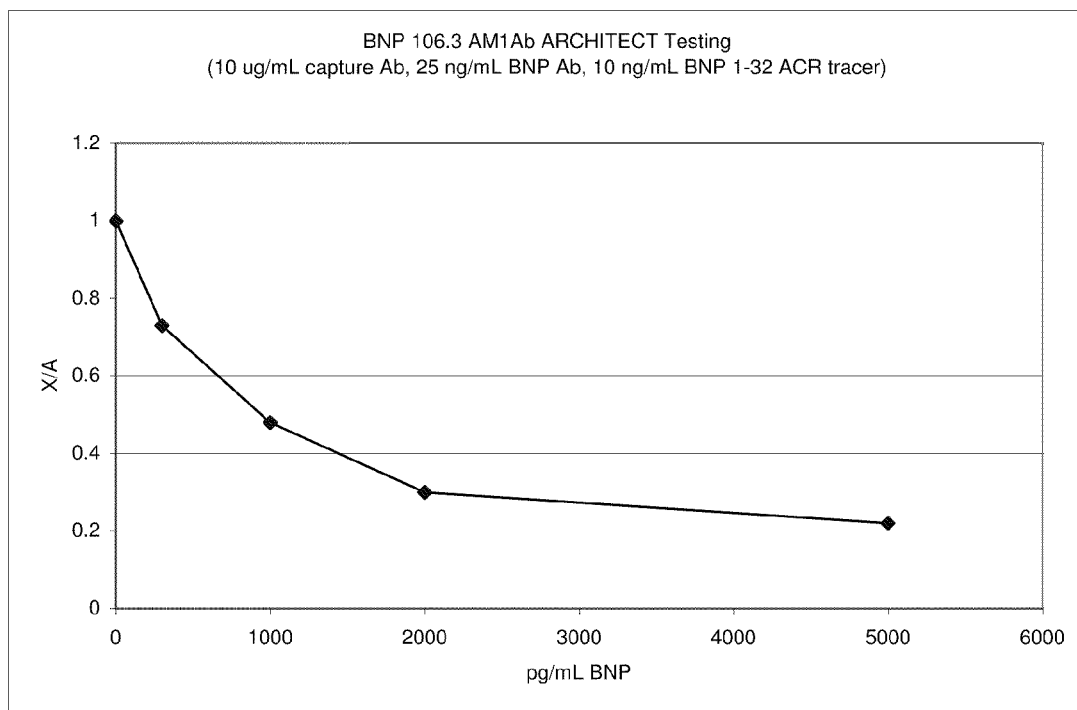
FIG. 15 shows the results of testing to determine antibody AM1's ability to bind to human cyclic BNP 1-32 in a single antibody assay format as described in Example 3 (X=signal generated with given concentration of unlabelled human cyclic BNP 1-32; A=signal generated with no unlabelled human cyclic BNP 1-32; X/A ratio of these two signals).

These coated microparticles were then tested on the ARCHITECT® instrument (Abbott Laboratories, Abbott Park, Ill.) for reactivity to human cyclic BNP 1-32 (SEQ ID NO:5). An aliquot containing human cyclic BNP 1-32 (SEQ ID NO:5) was delivered to the same well of the reaction vessel as the microparticles to form a reaction mixture. The reaction mixture was incubated for approximately 18 minutes. After incubation, the microparticles were washed with the ARCHITECT® Line Diluent to remove any of the human cyclic BNP 1-32 (SEQ ID NO:5) that was not captured. The ARCHITECT® Line Diluent is commercially available from Abbott Laboratories, Abbott Park, Ill. Next, human cyclic BNP 1-32 (SEQ ID NO:5) linked to acridinium (hereinafter "tracer") was dispensed into the reaction vessel and allowed to react with the microparticles for about 4 minutes, after which the microparticles were washed with the ARCHITECT® Line Diluent to remove the unbound materials. The tracer was diluted to about 5-25 ng/mL. A solution of hydrogen peroxide and then sodium hydroxide was added to the reaction vessel and the chemiluminescent signal was measured by the chemiluminescent microparticle immunoassay (CMIA) optical assembly of the ARCHITECT® instrument. As shown in FIG. 15, in this assay format, the antibody AM1 showed reactivity to the unlabelled human cyclic BNP 1-32 (SEQ ID NO:5) in a concentration dependent manner.

EXAMPLE 4

Sandwich Assays Using Antibodies Produced by CHO Cell Line AM1

For the modified ARCHITECT®-hBNP assay (hereinafter referred to as "Arc-BNP") paramagnetic particles were coated with monoclonal antibody ("mAb") 3-631-436. This mAb binds to an amino acid sequence containing amino acids 13-18 on the hBNP (SEQ ID NO:5) peptide. (Monoclonal antibodies produced by hybridoma cell line 3-631-436 are described in U.S. patent application Ser. No. 11/135,050, filed on May 25, 2005, the contents of which are herein incorporated by reference. Monoclonal antibodies produced by hybridoma cell line 3-631-436 are also referred interchangeably herein as "monoclonal antibody 3-631-436" and "Fusion 3". Additionally, murine hybridoma cell line 3-631-436 was deposited with the A.T.C.C. on Dec. 21, 2004 and assigned A.T.C.C. Accession No. PTA-6476). Monoclonal antibody 3-631-436 was coated onto a paramagnetic particle (Polymer Laboratories, Amherst, Mass.) using the techniques described in U.S. Pat. No. 6,162,902. Specifically, EDAC coupling was used (EDAC is generally used as a carboxyl activating agent for amide bonding with primary amines. In addition, it reacts with phosphate groups. It is used in peptide synthesis, crosslinking proteins to nucleic acids and in preparing immunoconjugates. The chemical formula for EDAC is 1-ethyl-3-(3-dimethylaminopropyl)carbodiimide, hydrochloride. EDAC is commercially available from Sigma-Aldrich, St. Louis, Mo.). Particles were washed and overcoated with BSA. These particles were used to capture BNP peptide in the assay during the first ($1^{st}$) incubation with specimens.

Alternatively, monoclonal antibody 3-631-436 was biotinylated using NHS-PEO$_4$-biotin (Pierce Biotechnology, Inc., Rockford, Ill.) and captured on streptavidin-coated superparamagnetic Dynabeads (Dynal Biotech LLC, Brown Deer, Wis.). These particles were also used to capture BNP peptide in the assay during the first ($1^{st}$) incubation with specimens.

Antibody AM1 (See Examples 1 and 2) was conjugated to acridinium (Abbott Laboratories, Abbott Park, Ill.) and is used in the assay during the second ($2^{nd}$) incubation to detect the particle-bound hBNP peptide. The conjugation occurred by reaction of antibody AM1 with an activated acridinium-carboxamide ester.

In a complimentary modified Arc-BNP assay to that described above, capture particles were prepared by coating antibody AM1 onto paramagnetic particles (Polymer Laboratories, Amherst, Mass.) utilizing EDAC chemistry or by biotinylation of antibody AM1 and capture on streptavidin coated superparamagnetic Dynabeads (Invitrogen, Carlsbad, Calif.). The procedures were identical to those described above for preparation of monoclonal antibody 3-631-436 particles. These particles were also used to capture hBNP peptide in the assay during the first ($1^{st}$) incubation with specimens. Monoclonal antibody 3-631-436 was conjugated to acridinium the same way antibody AM1 was conjugated to acridinium and is used in the assay during the 2nd incubation to detect the particle-bound hBNP peptide.

BNP immunoassays were performed on an ARCHITECT® instrument (this instrument is described in U.S. Pat. No. 5,468,646).

An aliquot containing a calibrator solution was delivered to the same well of the reaction vessel as the microparticles to form a reaction mixture. The calibrator solution contained hBNP full-length peptide. The microparticles coated with the capture antibody in a Tris/BSA diluent were pipetted by the sampling probe into the appropriate wells of the reaction vessel in the sampling center. The reaction mixture was incubated for approximately 4 minutes (18 min for streptavidin based particles) at a temperature of about 37° C. After the incubation, the reaction mixture was washed with the ARCHITECT® Line Diluent to remove any of the calibrator that was not captured. The ARCHITECT® Line Diluent is commercially available from Abbott Laboratories, Abbott Park, Ill.

The mAb-Acridinium-conjugates at about 50-100 ng/mL were dispensed into the reaction vessel and incubated for approximately 4 minutes at a temperature of about 37° C. After the incubation, the reaction vessel was washed with the ARCHITECT® Line Diluent to remove the unbound materials.

A solution of hydrogen peroxide and then sodium hydroxide was added to the reaction vessel and the chemiluminescent signal was measured by the chemiluminescent microparticle immunoassay (CMIA) optical assembly of the ARCHITECT® instrument.

Figure 16:
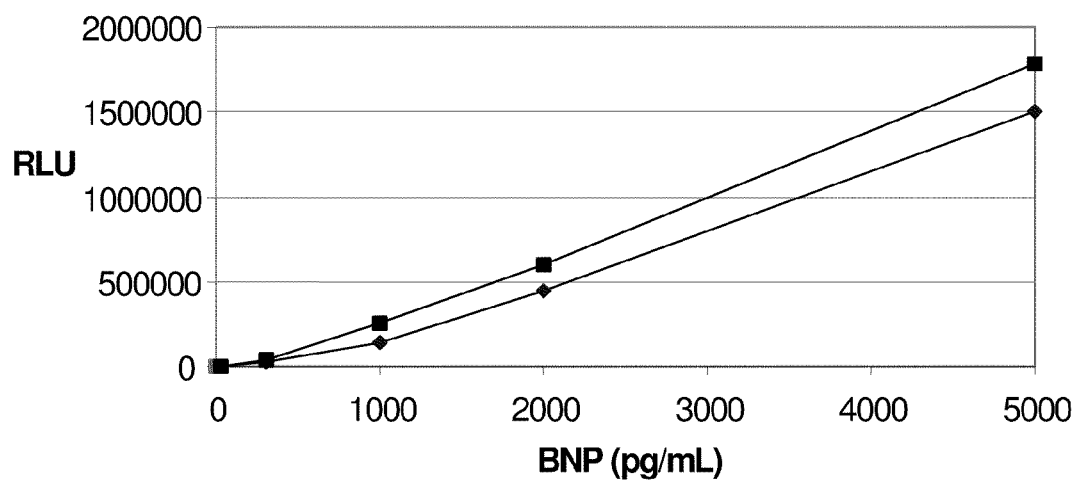
FIG. 16 shows an anti-hBNP antibody pair evaluation using streptavidin microparticles using antibody AM1 and Fusion 3 as described in Example 4. In essence, the following were employed: M280 Streptavidin particles at 0.05% solids, 65 ng/mL conjugates, 100 μL sample volume, and a 2-step (18/4) sandwich format. Symbols & Abbreviations: diamonds, anti-BNP (106.3AM1) SA μP/anti-BNP (Fusion 3) CPSP; squares, anti-BNP (Fusion 3) SA μP/anti-BNP (106.3AM1) CPSP); RLU, Relative Light Units.
Figure 17:
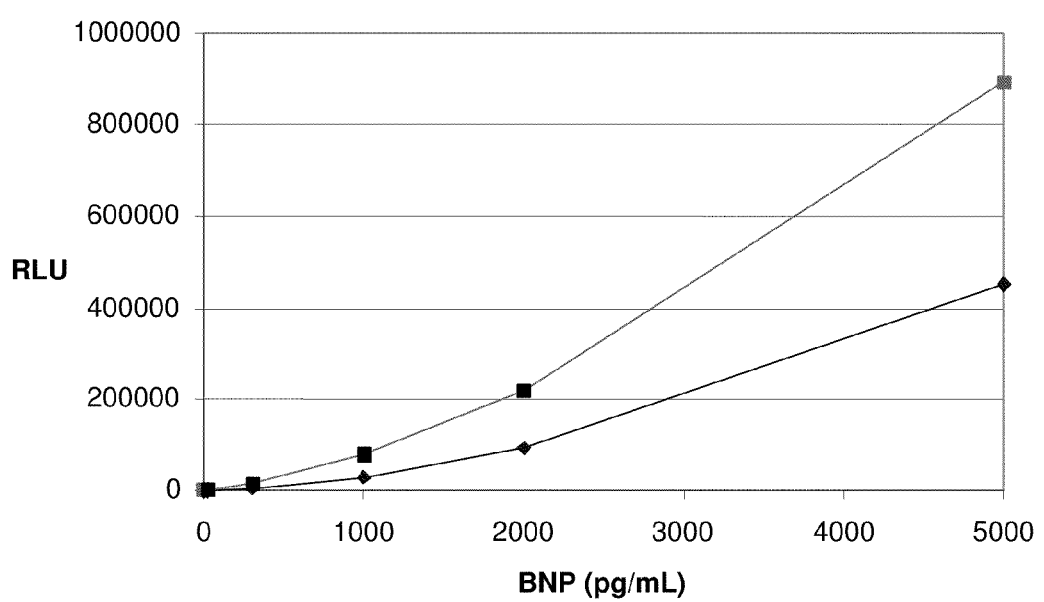
FIG. 17 shows anti-hBNP antibody pair evaluation using paramagnetic microparticles (from Polymer Labs) using antibody AM1 and Fusion 3 as described in Example 4. Symbols & Abbreviations: diamonds, anti-BNP (106.3AM1) SA μP/anti-BNP (Fusion 3) CPSP; squares, anti-BNP (Fusion 3) SA μP/anti-BNP (106.3AM1) CPSP); RLU, Relative Light Units.

The ARCHITECT® system measures the acridinium signals which are typically measured in relative light units (hereinafter "rlu's"). Measurements were made in triplicate. The results shown in Table 1 below and in FIGS. 16 and 17 show the mean of the triplicate values. Specifically, the results in Table B and FIGS. 16 and 17 are shown in pg/mL BNP calibrator.

TABLE 1

| | | uP mAb clone | | | |
|---|---|---|---|---|---|
| | | 106.3AM1 | 3-631-436 | 106.3AM1 | 3-631-436 |
| | | | Conj mAb clone | | |
| BNP (pg/mL) | | 3-631-436 | 106.3AM1 | 3-631-436 | 106.3AM1 |
| | Sample | | | | |
| 0 | Cal A | 1132 | 1275 | 706 | 528 |
| 30 | Cal B | 1784 | 2386 | 671 | 1291 |
| 300 | Cal C | 19819 | 35445 | 3907 | 12618 |
| 1000 | Cal D | 142648 | 250363 | 28612 | 76400 |
| 2000 | Cal E | 446152 | 600661 | 93326 | 216220 |
| 5000 | Cal F | 1502213 | 1780437 | 451856 | 893368 |
| | Ratio | | | | |
| | A/A | 1.0 | 1.0 | 1.0 | 1.0 |
| | B/A | 1.6 | 1.9 | 1.0 | 2.4 |
| | C/A | 17.5 | 27.8 | 5.5 | 23.9 |
| | D/A | 126.0 | 196.4 | 40.5 | 144.6 |
| | E/A | 394.0 | 471.1 | 132.2 | 409.2 |

In addition, the immunoassays can be used to monitor patients receiving therapeutic doses of hBNP or fragments of hBNP and anti-hBNP treatments.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. Chinese hamster ovary ("CHO") cell line AM1 having A.T.C.C. Accession No. PTA-6987.

2. An antibody: which immunospecifically binds hBNP made from DNA extracted from the CHO cell line AM1 having A.T.C.C. Accession No. PTA-6987.

3. A chimeric antibody or a hBNP-epitope binding fragment thereof produced by CHO cell line AM1, wherein said cell line has A.T.C.C. Accession No. PTA-6987.

4. An isolated antibody which immunospecifically binds to hBNP, wherein said antibody has a variable heavy domain and a variable light domain, the variable heavy domain comprising a heavy chain complementarity determining region ("CDR") 1, a heavy chain CDR 2 and a heavy chain CDR 3, the variable light domain comprising a light chain CDR 1, a light chain CDR 2 and a light chain CDR 3, wherein:

(a) Heavy Chain CDR 1 has the amino acid sequence of: Gly-Tyr-Thr-Phe-Thr-His-Tyr-Gly-Ile-Asn (SEQ ID NO:6);

(b) Heavy Chain CDR 2 has the amino acid sequence having a formula of:

Trp-Ile-Asn-Thr-His-Thr-Gly-Glu-$Xaa_1$-$Xaa_2$-Tyr-Ala-Asp-Asp-Phe-Lys-Gly    (SEQ ID NO: 12)

wherein $Xaa_1$ is selected from the group consisting of proline and alanine;

wherein $Xaa_2$ is selected from the group consisting of isoleucine and tyrosine;

(c) Heavy Chain CDR 3 has the amino acid sequence of: Ser-His-Arg-Phe-Gly-Leu-Asp-Tyr (SEQ ID NO:8);

(d) Light Chain CDR 1 has the amino acid sequence having a formula of:

(SEQ ID NO: 13)
Lys-Ala-$Xaa_3$-$Xaa_4$-$Xaa_5$-Val-Asp-Tyr-Asn-Gly-Asp-Ser-Tyr-Leu-Asn wherein Xaa₃ is selected from the group consisting of: serine, alanine, asparagine, glutamine, tyrosine, threonine and arginine;

wherein Xaa₄ is selected from the group consisting of: glutamine, tyrosine, tryptophan, alanine and phenylalanine;

wherein Xaa₅ is selected from the group consisting of: serine, glycine, proline, alanine and aspartic acid;

(e) Light Chain CDR 2 has the amino acid sequence having the formula of:

Ala-Ala-Ser-Xaa₆-Xaa₇-Xaa₈-Ser    (SEQ ID NO: 14)

wherein Xaa₆ is selected from the group consisting of: asparagine and cysteine;

wherein Xaa₇ is selected from the group consisting of: leucine, glycine and alanine;

wherein Xaa₈ is selected from the group consisting of glutamic acid, tryptophan and proline; and (f) Light Chain CDR 3 has the amino acid sequence of: Gln-Gln-Ser-Asn-Glu-Asp-Pro-Phe-Thr (SEQ ID NO:11), wherein the heavy chain CDR 2 has an amino acid sequence other than Trp-Ile-Asn-Thr-His-Thr-Gly-Glu-Pro-Ile-Tyr-Ala-Asp-Asp-Phe-Lys-Gly (SEQ ID NO:7) when the light chain CDR 1 has the amino acid sequence of Lys-Ala-Ser-Gln-Ser-Val-Asp-Tyr-Asn-Gly-Asp-Ser-Tyr-Leu-Asn (SEQ ID NO:9) and the light chain CDR 2 has the amino acid sequence of Ala-Ala-Ser-Asn-Leu-Glu-Ser (SEQ ID NO: 10), the light chain CDR 1 has an amino acid sequence other than Lys-Ala-Ser-Gln-Ser-Val-Asp-Tyr-Asn-Gly-Asp-Ser-Tyr-Leu-Asn (SEQ ID NO:9) when the heavy chain CDR 2 has the amino acid sequence Trp-Ile-Asn-Thr-His-Thr-Gly-Glu-Pro-Ile-Tyr-Ala-Asp-Asp-Phe-Lys-Gly (SEQ ID NO:7) and the light chain CDR 2 has the amino acid sequence Ala-Ala-Ser-Asn-Leu-Glu-Ser (SEQ ID NO: 10), or the light chain CDR 2 has an amino acid sequence other than Ala-Ala-Ser-Asn-Leu-Glu-Ser (SEQ ID NO: 10) when the heavy chain CDR 2 has the amino acid sequence of Trp-Ile-Asn-Thr-His-Thr-Gly-Glu-Pro-Ile-Tyr-Ala-Asp-Asp-Phe-Lys-Gly (SEQ ID NO:7) and the light chain CDR 1 has the amino acid sequence of Lys-Ala-Ser-Gln-Ser-Val-Asp-Tyr-Asn-Gly-Asp-Ser-Tyr-Leu-Asn (SEQ ID NO:9).

5. The antibody of claim 4, wherein:
Xaa₁ is alanine,
Xaa₂ is tyrosine,
Xaa₃ is serine,
Xaa₄ is glutamine,
Xaa₅ is serine,
Xaa₆ is asparagine,
Xaa₇ is leucine,
Xaa₈ is glutamic acid.

6. The antibody of claim 4, wherein:
Xaa₁ is proline,
Xaa₂ is isoleucine,
Xaa₃ is glutamine,
Xaa₄ is phenylalanine,
Xaa₅ is alanine,
Xaa₆ is asparagine,
Xaa₇ is leucine,
Xaa₈ is glutamic acid.

7. The antibody of claim 4, wherein:
Xaa₁ is proline,
Xaa₂ is isoleucine,
Xaa₃ is tyrosine,
Xaa₄ is alanine,
Xaa₅ is serine,
Xaa₆ is asparagine,
Xaa₇ is leucine,
Xaa₈ is glutamic acid.

8. The antibody of claim 4, wherein:
Xaa₁ is proline,
Xaa₂ is isoleucine,
Xaa₃ is glutamine,
Xaa₄ is tryptophan,
Xaa₅ is glycine,
Xaa₆ is asparagine,
Xaa₇ is leucine,
Xaa₈ is glutamic acid.

9. The antibody of claim 4, wherein:
Xaa₁ is proline,
Xaa₂ is isoleucine,
Xaa₃ is threonine,
Xaa₄ is tryptophan,
Xaa₅ is aspartic acid,
Xaa₆ is asparagine,
Xaa₇ is leucine,
Xaa₈ is glutamic acid.

10. The antibody of claim 4, wherein:
Xaa₁ is proline,
Xaa₂ is isoleucine,
Xaa₃ is arginine,
Xaa₄ is tryptophan,
Xaa₅ is proline,
Xaa₆ is asparagine,
Xaa₇ is leucine,
Xaa₈ is glutamic acid.

11. The antibody of claim 4, wherein:
Xaa₁ is proline,
Xaa₂ is isoleucine,
Xaa₃ is alanine,
Xaa₄ is tyrosine,
Xaa₅ is glycine,
Xaa₆ is asparagine,
Xaa₇ is leucine,
Xaa₈ is glutamic acid.

12. The antibody of claim 4, wherein:
Xaa₁ is proline,
Xaa₂ is isoleucine,
Xaa₃ is asparagine,
Xaa₄ is tryptophan,
Xaa₅ is proline,
Xaa₆ is asparagine,
Xaa₇ is leucine,
Xaa₈ is glutamic acid.

13. The antibody of claim 4, wherein:
Xaa₁ is proline,
Xaa₂ is isoleucine,
Xaa₃ is serine,
Xaa₄ is glutamine,
Xaa₅ is serine,
Xaa₆ is cysteine,
Xaa₇ is glycine,
Xaa₈ is tryptophan.

14. The antibody of claim 4, wherein:
Xaa₁ is proline,
Xaa₂ is isoleucine,
Xaa₃ is serine,
Xaa₄ is glutamine,
Xaa₅ is serine,
Xaa₆ is cysteine,
Xaa₇ is alanine,
Xaa₈ is proline.

15. The antibody of claim 4, wherein said antibody is a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof.

16. The antibody of claim 4, wherein said antibody immunospecifically binds to an epitope comprising amino acid residues 5 through 13 of hBNP (SEQ ID NO:5).

17. An immunoassay kit for hBNP or hBNP fragment, wherein said immunoassay kit comprises an antibody of claim 4.

18. The immunoassay kit of claim 4, wherein said immunoassay kit comprises a single antibody that immunospecifically binds to hBNP or hBNP fragment.

19. The immunoassay kit of claim 18, wherein said immunoassay further comprises an additional specific binding partner for hBNP or hBNP fragment.

20. A composition comprising an antibody of claim 4 in a pharmaceutically acceptable carrier.

* * * * *

UNITED STATES PATENT AND TRADEMARK OFFICE
CERTIFICATE OF CORRECTION

PATENT NO. : 7,998,480 B2  
APPLICATION NO. : 12/189232  
DATED : August 16, 2011  
INVENTOR(S) : Susan E. Brophy et al.

Page 1 of 1

It is certified that error appears in the above-identified patent and that said Letters Patent is hereby corrected as shown below:

IN THE CLAIMS:

Claim 18 (column 92, line 1) change "kit of claim 4" to -- kit of claim 17 --.

Claim 19 (column 92, line 4) change "kit of claim 18" to -- kit of claim 17 --.

Claim 19 (column 92, line 5) add -- kit -- after "said immunoassay".

Signed and Sealed this  
Twenty-fifth Day of June, 2013

Teresa Stanek Rea  
*Acting Director of the United States Patent and Trademark Office*